United States Patent
Dahnke et al.

(10) Patent No.: US 7,547,691 B2
(45) Date of Patent: Jun. 16, 2009

(54) [4-(BENZO[B]THIOPHEN-2-YL) PYRIMIDIN-2-YL]-AMINE DERIVATIVES AS IKK-BETA INHIBITORS FOR THE TREATMENT OF CANCER AND INFLAMMATORY DISEASES

(75) Inventors: Karl Robert Dahnke, Carmel, IN (US); Ho-Shen Lin, Indianapolis, IN (US); Michael Enrico Richett, Indianapolis, IN (US); Chuan Shih, Carmel, IN (US); Q May Wang, Indianapolis, IN (US); Bo Zhang, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 12/093,024

(22) PCT Filed: Nov. 15, 2006

(86) PCT No.: PCT/US2006/060911

§ 371 (c)(1), (2), (4) Date: May 8, 2008

(87) PCT Pub. No.: WO2007/092095

PCT Pub. Date: Aug. 16, 2007

(65) Prior Publication Data

US 2008/0306082 A1 Dec. 11, 2008

Related U.S. Application Data

(60) Provisional application No. 60/738,097, filed on Nov. 18, 2005.

(51) Int. Cl.
C07D 409/04 (2006.01)
A61K 31/506 (2006.01)

(52) U.S. Cl. .......... 514/218; 514/252.14; 514/275; 540/575; 544/295; 544/331

(58) Field of Classification Search .......... 540/575; 544/295, 331; 514/218, 252.14, 275
See application file for complete search history.

(56) References Cited

FOREIGN PATENT DOCUMENTS

| WO | WO 2004/089913 | 10/2004 |
|----|----------------|---------|
| WO | WO 2006/066172 | 6/2006 |

OTHER PUBLICATIONS

Meeting Abstracts, Innovative Rheumatology: Gene and Cell Therapies of Arthritis and Related Autoimmune Disorders Second International Meeting, Arthritis Research 3 (Suppl 1):A1-A16, 2001.*
Catley et al., Validation of IKKbeta as therapeutic target in airway inflammatory disease by adenoviral-mediated delivery dominant-negative IKKbeta to pulmonary epithelial cells, British Journal of Pharmacology, vol. 145 (1), pp. 114-122, (2005).*
Greten et al., IKKbeta Links Inflammation and Tumorigenesis in a Mouse Model of Colitis-Associated Cancer, Cell, vol. 118, pp. 285-296, Aug. 6, 2004.*

* cited by examiner

*Primary Examiner*—Deepak Rao
(74) *Attorney, Agent, or Firm*—Tina M. Tucker

(57) ABSTRACT

The present invention provides compounds of Formula I: useful in the treatment of cancer and inflammatory diseases.

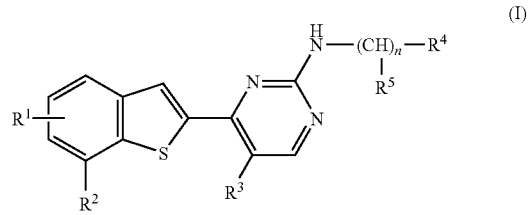

(I)

9 Claims, No Drawings

[4-(BENZO[B]THIOPHEN-2-YL) PYRIMIDIN-2-YL]-AMINE DERIVATIVES AS IKK-BETA INHIBITORS FOR THE TREATMENT OF CANCER AND INFLAMMATORY DISEASES

This application is a 371 of PCT/US06/60911 filed Nov. 15, 2006 which claims benefit of U.S. Provisional Application No. 60/738,097 filed Nov. 18, 2005.

BACKGROUND OF THE INVENTION

Protein kinases modulate a wide variety of biological processes of cells, especially those that carry signals from the cell membrane to intracellular targets and coordinate complex cellular functions. Many extracellular stimuli that induce cellular responses to occur inside the cells act through affecting protein kinases and the pathways regulated by these kinases. Consequently, one or more cellular responses such as cell proliferation, differentiation, migration, activation of transcription factors, control of protein synthesis, regulation of cell cycle, secretion of hormones and cytokines/chemokines, and glycogen metabolism can be regulated by these extracellular stimuli. Examples of such stimuli include various environmental stress signals (e.g. oxidative stress; heat shock, ultraviolet radiation, bacterial endotoxin, $H_2O_2$), inflammatory cytokines (e.g. tumor necrosis factor a (TNF-β) and interleukin-6 (IL-6)), and growth factors (e.g. epidermal growth factor (EGF), and transforming growth factor beta (TGF-β)).

Due to the importance of protein phosphorylation in regulating many aspects of cell life, aberrant protein kinase activity will result in abnormal phosphorylation of key functional proteins and enzymes and therefore is associated with many human diseases, in particular those involved in proliferative and inflammatory responses, such as cancer, rheumatoid arthritis (RA), chronic obstructive pulmonary disease (COPD), inflammatory bowel disease, osteoarthritis, asthma, as well as cardiovascular and neurological disorders. Accordingly, there has been a substantial effort in medicinal chemistry to develop therapeutic agents targeting protein kinases for the treatment of human diseases.

IKKbeta is a key kinase regulating inflammation and stress related pathways and thus has been linked to the development of a variety of human diseases. For example, intra-articular administration of a dominant-negative IKKbeta significantly reduced the severity of the adjuvant-induced arthritis in rats (Tak PP et al, *Arthritis Rheum.* (2001) 44(8)1897-1907). IKKbeta knockout cells have dramatic defects in expressing TNFα-induced cytokines, chemokines, or adhesion molecules that are involved in inflammatory disease such as RA and COPD. Through conditional or tissue-specific knockout of IKKbeta, this kinase is found to be required for survival and proliferation of peripheral B-cells and for prevention of apoptosis mediated by TNFα (Li Z-W, Omori A S, Labuda T, Karin M, Rickert R C, "IKKβ is required for peripheral B cell survival and proliferation" *The J. Immunol.*, (2003), 170: 4630-4637; Maeda S, Chang L, et al. *"IKKbeta is required for prevention of apoptosis mediated by cell-bound but not by circulating TNFα." Immunity*, (2003), 19:725-737). Moreover, deletion of IKKbeta in myeloid cells also reduced the growth of colitis-associated cancer (Greten F R et al, *Cell*, (2004), 118:285-296). Furthermore, several groups have demonstrated that IKKbeta kinase inhibitors can induce cell growth inhibition and/or augment TNFα- or TRAIL-induced cell death in different cancer cell lines (Takaomi et al *Clinical Cancer Res.*, (2005), Vol 11:1974-82; Hideshima et al, *JBC*, (2002) 277:16639-47; Lam et al *Clinical Cancer Res.*, (2005) Vol 11:28-40).

The present invention provides novel pyrimidinyl benzothiophene compounds believed to have clinical use for treatment of cancer and inflammatory diseases through inhibiting IKKbeta.

BRIEF SUMMARY OF THE INVENTION

The present invention provides compounds of Formula I:

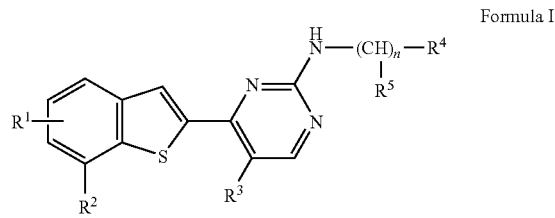

Formula I wherein:

$R^1$ is hydrogen, hydroxy, halo, methylthio, aminosulfonyl, pyrid-2-ylamino, 3-methylaminocarbonylphenyl, —C(O)$NR^8R^9$, —(CH$_2$)$_{0-1}$NHSO$_2R^{12}$, —CH$_2$NHCONHR$^{13}$, —NHC(O)R$^{14}$, or pyrrolidinonyl optionally substituted with ethyloxycarbonyl;

$R^2$ is hydrogen, hydroxy, halo, cyano, ($C_1$-$C_4$)alkyl, or ($C_1$-$C_4$)alkoxy;

$R^3$ is hydrogen, halo, or methyl;

$R^4$ is (a) —NR$^6$R$^7$ or (b) aminomethylcyclohexyl, piperidinyl, 2,2,6,6-tetramethylpiperidin-4-yl, 2,2,6,6-tetramethylpiperidin-4-ylethenyl, 4-($C_1$-$C_4$)alkylpiperidin-4-yl, or pyrrolidinyl;

wherein (b) may be optionally substituted with a substituent selected from the group consisting of ($C_2$-$C_4$)alkenyl, ($C_3$-$C_6$)cycloalkyl, C(O)R$^{10}$, and ($C_1$-$C_4$)alkyl optionally substituted with halo, ($C_1$-$C_4$)alkoxy, or ($C_3$-$C_6$)cycloalkyl;

$R^5$ is hydrogen when n is 1-7 or hydroxy when n is 2-7;

$R^6$ is hydrogen or ($C_1$-$C_4$)alkyl;

$R^7$ is selected from the group consisting of hydrogen, ($C_1$-$C_4$)alkyl, piperidin-4-yl optionally substituted with ($C_1$-$C_4$)alkyl, piperidinylcarbonyl optionally substituted with ($C_1$-$C_4$)alkyl, pyrrolidin-3-yl optionally substituted with ($C_1$-$C_4$)alkyl, and pyrrolidinylcarbonyl optionally substituted with ($C_1$-$C_4$)alkyl;

alternatively $R^6$ and $R^7$ along with the nitrogen to which they are attached form a ring selected from the group consisting of piperazinyl, homopiperazinyl, 4-dimethylaminopiperidin-1-yl, 3-dimethylaminopyrrolidin-1-yl, or hexahydropyrrolo[3,4-c]pyrrolyl;

wherein the ring may be optionally substituted from the group consisting of ($C_2$-$C_4$)alkenyl, ($C_3$-$C_6$)cycloalkyl, C(O)R$^{10}$, and one to three ($C_1$-$C_4$)alkyl substituents optionally substituted with hydroxy;

$R^8$ is hydrogen or ($C_1$-$C_4$)alkyl;

$R^9$ is hydrogen, ($C_1$-$C_4$)alkyl, ($C_1$-$C_4$)alkoxy, ($C_3$-$C_6$)cycloalkyl, thiazolyl, imidazolyl, pyridyl, phenyl optionally substituted with halo, 2-hydroxy-2-phenyl-ethyl, imidazolylethyl, 6-chloropyrid-3-ylmethyl, or furan-2-yl-($C_1$-$C_4$ alkyl);

alternatively $R^8$ and $R^9$ along with the nitrogen to which they are attached form a heterocycle selected from the group consisting of morpholinyl and thiazinyl;

$R^{10}$ is hydrogen, ($C_1$-$C_4$)alkyl, or NHR$^{11}$;

$R^{11}$ is hydrogen or ($C_1$-$C_4$)alkyl;

$R^{12}$ is $(C_1$-$C_4)$alkyl, trifluoro$(C_1$-$C_4)$alkyl, benzyl, or $(C_3$-$C_6)$cycloalkyl;

$R^{13}$ is $(C_1$-$C_4)$alkyl, $(C_3$-$C_6)$cycloalkyl, or benzyl optionally substituted with $(C_1$-$C_4)$alkyl, halo, or $(C_1$-$C_4)$alkoxy;

$R^{14}$ is $(C_3$-$C_6)$cycloalkyl, piperidinyl, indolylmethyl, or benzyl optionally substituted with 3-dimethylamino-2-hydroxypropoxy;

provided that when $R^4$ is piperidinyl, $R^1$ is C(O)NR$^8$R$^9$; and n is 1-7 provided that n is 1 only when $R^4$ is aminomethylcyclohexyl or 2,2,6,6-tetramethylpiperidin-4-ylethenyl; or a pharmaceutically acceptable salt thereof.

The present invention provides a method of treating multiple myeloma in a mammal comprising administering to a mammal in need of such treatment an effective amount of a compound of Formula I or a pharmaceutically acceptable salt thereof.

The present invention also provides a method of treating colon cancer in a mammal comprising administering to a mammal in need of such treatment an effective amount of a compound of Formula I or a pharmaceutically acceptable salt thereof.

The present invention also provides a method of treating large cell lung cancer in a mammal comprising administering to a mammal in need of such treatment an effective amount of a compound of Formula I or a pharmaceutically acceptable salt thereof.

The present invention also provides a method of treating glioblastoma in a mammal comprising administering to a mammal in need of such treatment an effective amount of a compound of Formula I or a pharmaceutically acceptable salt thereof.

The present invention also provides a method of treating ovarian cancer in a mammal comprising administering to a mammal in need of such treatment an effective amount of a compound of Formula I or a pharmaceutically acceptable salt thereof.

The present invention also provides a method of treating rheumatoid arthritis in a mammal comprising administering to a mammal in need of such treatment an effective amount of a compound of Formula I or a pharmaceutically acceptable salt thereof.

The present invention also provides a method of treating chronic obstructive pulmonary disease in a mammal comprising administering to a mammal in need of such treatment an effective amount of a compound of Formula I or a pharmaceutically acceptable salt thereof.

The present invention also provides a pharmaceutical formulation comprising a compound of Formula I or a pharmaceutically acceptable salt thereof, in combination with a pharmaceutically acceptable excipient, carrier, or diluent.

This invention also provides the use of a compound of Formula I or a pharmaceutically acceptable salt thereof for the manufacture of a medicament for the treatment of cancer, in particular multiple myeloma, colon cancer, large cell lung cancer, glioblastoma, and ovarian cancer. Additionally, this invention provides a compound of Formula I or a pharmaceutically acceptable salt thereof for use in the treatment of cancer in mammals, in particular multiple myeloma, colon cancer, large cell lung cancer, glioblastoma, and ovarian cancer. Furthermore, this invention provides a pharmaceutical composition adapted for the treatment of cancer, in particular multiple myeloma, colon cancer, large cell lung cancer, glioblastoma, and ovarian cancer comprising a compound of Formula I or a pharmaceutically acceptable salt thereof in combination with one or more pharmaceutically acceptable excipients, carriers, or diluents.

This invention also provides the use of a compound of Formula I or a pharmaceutically acceptable salt thereof for the manufacture of a medicament for the treatment of inflammatory diseases, in particular rheumatoid arthritis and chronic obstructive pulmonary disease. Additionally, this invention provides a compound of Formula I or a pharmaceutically acceptable salt thereof for use in the treatment of inflammatory diseases, in particular rheumatoid arthritis and chronic obstructive pulmonary disease. Furthermore, this invention provides a pharmaceutical composition adapted for the treatment of inflammatory diseases, in particular rheumatoid arthritis and chronic obstructive pulmonary disease comprising a compound of Formula I or a pharmaceutically acceptable salt thereof in combination with one or more pharmaceutically acceptable excipients, carriers, or diluents.

The invention also provides a compound of Formula II:

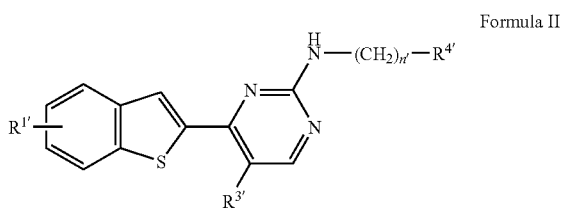

Formula II wherein:

$R^{1'}$ is hydrogen, —C(O)X, hydroxy, $(C_1$-$C_3)$alkyl, $(C_1$-$C_3)$alkoxy, halo, or cyano;

X is amino-, methylamino-, cyclopropylamino-, thiazolylamino-, imidazolylamino-, morpholinyl, or thiazinyl;

$R^{3'}$ is hydrogen, methyl, or halo; and $R^{4'}$ is piperidin-4-yl optionally substituted with $C_1$-$C_4$ alkyl, piperazin-4-yl optionally substituted with one to three $C_1$-$C_4$ alkyl substituents one of which is optionally substituted with hydroxy; 3-dimethylaminopyrrolidin-1-yl; -aminomethylcyclohexyl; homopiperazinyl; hexahydro-pyrolo[3,4-c]pyrrole; or R$^a$R$^b$N—$(C_1$-$C_4)$alkyl;

provided that when $R^{4'}$ is piperidinyl, $R^{1'}$ is —CO(X);

$R^a$ and $R^b$ are independently H or methyl; and

N' is 1-4 provided that n' is 1 only when $R^{4'}$ is aminomethylcyclohexyl; or a pharmaceutically acceptable salt thereof.

DETAILED DESCRIPTION OF THE INVENTION

The general chemical terms used in the formulae above have their usual meanings. For example, the term "$(C_1$-$C_4)$ alkyl" includes straight chain and branched alkyls, e.g., methyl, ethyl, propyl, isopropyl, butyl, isobutyl, sec-butyl, and tert-butyl. The term "$(C_1$-$C_4)$alkoxy" includes methoxy, ethoxy, propoxy, and butoxy. The term "$(C_3$-$C_6)$cycloalkyl" includes cyclopropyl, cyclobutyl, cyclopentyl and cyclohexyl. The term "$(C_2$-$C_4)$alkenyl" includes straight chain and branched alkenyls, e.g., ethenyl, propenyl, isopropenyl, butenyl, isobutenyl, sec-butenyl, and tert-butenyl. The term "halo" includes fluoro, chloro, bromo, and iodo.

The skilled artisan will appreciate that certain compounds of Formula I contain at least one chiral center. The present invention contemplates all individual enantiomers or diastereomers, as well as mixtures of the enantiomers and diastereomers of said compounds including racemates. It is preferred that compounds of Formula I containing at least one chiral center exist as single enantiomers or diastereomers. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques.

It will be understood by the skilled reader that most or all of the compounds of the present invention are capable of forming salts. The compounds of the present invention are amines, and accordingly react with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol 66, No. 1, January 1977. Such salts include salts formed from the following acids: acetic acid, citric acid, esylic acid, fumaric acid, glyolic acid, glucuronic acid, glutaric acid, hydrochloric acid, lactic acid, maleic acid malic-d acid, malic-1 acid, mandelic-d acid, mandelic 1 acid, mesylic acid, napadisylic acid, oxalic acid, phosphoric acid, succinic acid, sulfuric acid, tartaric-d acid, tartaric-1 acid, and tosylic acid.

While all of the compounds of Formula I are useful in the treatment of cancer and inflammatory diseases certain classes of compounds are preferred. The following paragraphs describe such preferred classes:
a) $R^1$ is $C(O)NR^8R^9$;
b) $R^2$ is hydrogen, hydroxy, methoxy;
c) $R^3$ is hydrogen, chloro, or methyl;
d) $R^4$ is —$NR^6R^7$, piperidinyl, or pyrrolidinyl;
e) $R^5$ is hydrogen;
f) $R^6$ and $R^7$ along with the nitrogen to which they are attached form a piperazinyl optionally substituted with one to three $(C_1\text{-}C_4)$alkyl;
g) $R^1$ is —$C(O)NR^8R^9$ and is attached in the 4-position of the benzothiophene, $R^8$ is hydrogen, and $R^9$ is $(C_1\text{-}C_4)$alkyl or $(C_2\text{-}C_6)$cycloalkyl;
h) $R^1$ is —$C(O)NR^8R^9$ and is attached in the 6-position of the benzothiophene, $R^8$ is one to three $(C_1\text{-}C_4)$alkyl substituents, and $R^9$ is $(C_1\text{-}C_4)$alkyl or $(C_2\text{-}C_6)$cycloalkyl;
i) $R^1$ is —$C(O)NR^8R^9$; $R^2$ is hydrogen; $R^3$ is hydrogen, halo, or methyl; $R^4$ is —$NR^6R^7$, piperidinyl, or 4-$(C_1\text{-}C_4)$alkylpiperidin-4-yl; wherein $R^4$ may be optionally substituted with $(C_1\text{-}C_4)$alkyl; $R^5$ is hydrogen; $R^6$ and $R^7$ along with the nitrogen to which they are attached form a piperazinyl optionally substituted with $(C_1\text{-}C_4)$alkyl; $R^8$ is hydrogen or $(C_1\text{-}C_4)$alkyl; $R^9$ $(C_1\text{-}C_4)$alkyl or $(C_3\text{-}C_6)$cycloalkyl; alternatively $R^8$ and $R^9$ along with the nitrogen to which they are attached can form a morpholinyl; and n is 2-3; and j) A compound selected from the group consisting of 2-{5-chloro-2-[3-(4-methylpiperazin-1-yl)-propylamino]-pyrimidin-4-yl}-benzo[b]thiophene-4-carboxylic acid cyclopropylamide tri-hydrochloride and 2-{5-methyl-2-[3-(4-methylpiperazin-1-yl)-propylamino]-pyrimidin-4-yl}-benzo[b]thiophene-4-carboxylic acid cyclopropylamide di-hydrochloride.

The compounds of the present invention can be prepared by a variety of procedures, some of which are illustrated in the schemes below. It will be recognized by one of skill in the art that the individual steps in the following schemes may be varied to provide the compounds of Formula I. The particular order of steps required to produce the compounds of Formula I is dependent upon the particular compound being synthesized, the starting compound, and the relative lability of the substituted moieties. Some substituents have been eliminated in the following schemes for the sake of clarity and are not intended to limit the teaching of the schemes in any way. The products and intermediates are isolated after standard extractive and chromatographic or crystallization techniques. As used herein, the term "suitable protecting group" means a well-known protecting group such as those described in T. W. Greene, "Protecting Groups in Organic Synthesis", John Wiley and Sons, New York, N.Y., 1991. The products and intermediates are isolated after standard extractive and chromatographic or crystallization techniques.

The compounds of Formula I may be prepared as described in the following scheme.

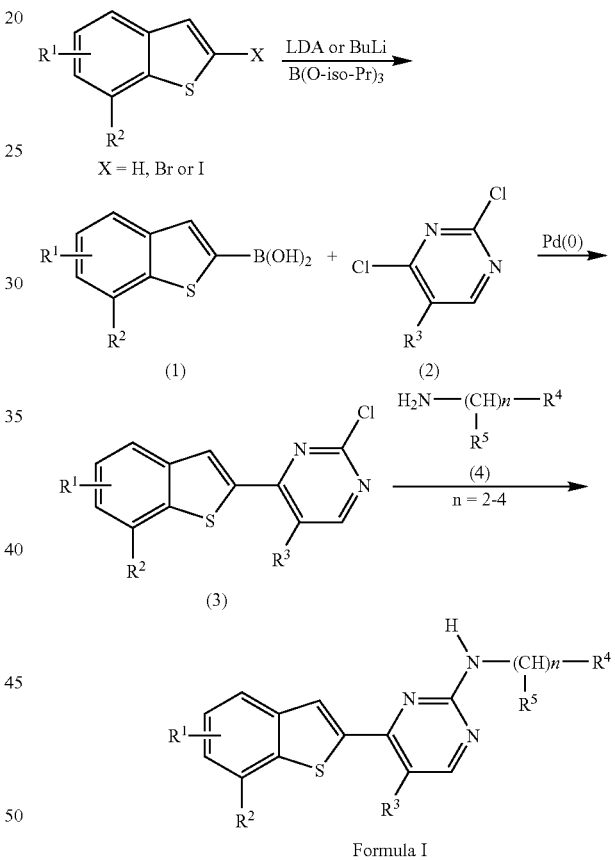

A substituted or unsubstituted benzo[b]thiophene is first metallated with butyl lithium followed by reaction with a lower $(C_1\text{-}C_4)$ trialkylboronate ester, such as triisopropyl borate to produce the boronic acid (1) upon workup. As an alternative to butyl lithium when X is hydrogen, a 2-boronic acid intermediate may be synthesized if $R^1$ is bromo or iodo and metallated at the 2-position with lithium diisopropyl amine in THF followed by the trialkylboronate ester. Compound (1) then undergoes a palladium catalyzed coupling reaction using a reagent such as $PdCl_2(dppb)$ in a polar aprotic solvent such as 1,4-dioxane with a 2,4-dichloropyrimidine (2) at elevated temperature (70-110° C.) to produce the halopyrimidine (3). The halogen at the 2 position of halopyrimidine (3) is then displaced by (4) or an excess of (4), often at elevated temperatures (~95° C.), or in the presence of a base such as sodium hydride or lithium carbonate to produce Formula I.

The primary amines (4) are either commercially available or may be prepared via 1) sodium azide, amine or protected amine displacement reactions on alkylhalide or alkylsulfonate substrates or 2) reductive amination of aldehydes or ketones that are known in the art. It should be clear to one skilled in the art of chemical transformations that the primary amine (4) may contain a second amino group that is either 1) less reactive in the displacement reaction as a secondary amine or 2) protected from displacement by any of a number of protection groups, such as tert-butylcarbamates, phthalimides, or benzylcarbamates which can be subsequently removed by acid hydrolysis, treatment with hydrazine, or hydrogenation, respectively.

If $R^1$ is bromo, then several known functional group transformations may also be performed. For example, palladium catalyzed carbonylation, using a reagent such as $Pd(OAc)_2$/dppf, where R=bromo in methanol provides a methyl ester. This is followed by further known ester transformations, such as hydrolysis to the acid or aminolysis to an amide. A free acid above may also be coupled with amines in the presence of a variety of dehydrating agents known to those skilled in the art to form amides. Similarly, the N-methoxy amide of acid functions are known to those skilled in the art to be suitable substrates for preparing ketones and the like, by reaction with heteroaryllithium reagents.

The skilled artisan will appreciate that not all of the substituents in the compounds of Formula I will tolerate certain reaction conditions employed to synthesize the compounds. These moieties may be introduced at a convenient point in the synthesis, or may be protected and then deprotected as necessary or desired. The skilled artisan will appreciate that the protecting groups may be removed at any convenient point in the synthesis of the compounds of the present invention. Methods for introducing and removing nitrogen and oxygen protecting groups are well known in the art; see, for example, Greene and Wuts, *Protective Groups in Organic Synthesis*, 3$^{rd}$ Ed., John Wiley and Sons, New York, Chapter 7 (1999). Furthermore, the skilled artisan will appreciate that in many circumstances, the order in which moieties are introduced is not critical. The particular order of steps required to produce the compounds of Formula I can be dependent upon the particular compound being synthesized, the starting compound, and the relative lability of the substituted moieties.

PREPARATION 1
[1,4-Bis(diphenylphosphino)butane]dichloropalladium(II) ([dppb]PdCl$_2$)

Bis(benzonitrile)dichloropalladium(II) (20.0 g, 52.1 mmol) is dissolved in trichloromethane (CHCd$_3$) (200 mL), then a solution of 1,4-bis(diphenylphosphino)butane in CHCd$_3$ (200 mL) is added in portions over 20 minutes. After stirring for 40 minutes, the yellow solid is filtered, washed with CHCl$_3$ (200 mL) and dried in vacuum oven overnight to give the title compound (30.6 g, 97% yield).

PREPARATION 2
4-(3-Aminopropyl)-piperazine-1-carboxylic acid tert-butyl ester (A). Preparation of 4-(3-bromopropyl)-piperazine-1-carboxylic acid tert-butyl ester.

1,3-Dibromopropane (6.78 mL, 66.8 mmol) is added to a stirred solution of piperazine-1-carboxylic acid tert-butyl ester (4.15 g, 22.2 mmol) and diisopropylethylamine (7.73 mL, 44.4 mmol) in anhydrous 1,4-dioxane (40 mL). The resultant mixture is heated in an oil bath at 90° C. for 20 hours. At ambient temperature ethyl acetate (160 mL) and half-saturated aqueous sodium bicarbonate (NaHCO$_3$) (120 mL) are added to the mixture. The organic layer is separated, dried over magnesium sulfate, filtered, and concentrated. The crude oil is subjected to chromatography on silica gel and eluted with 2 M NH$_3$/MeOH in dichloromethane 0-3% to provide the title compound as a dark oil (4.80 g, 70% yield).

(B). Preparation of 4-(3-azido-propyl)-piperazine-1-carboxylic acid tert-butyl ester Sodium azide (2.24 g, 34.2 mmol) is added to a stirred solution of 4-(3-bromo-propyl)-piperazine-1-carboxylic acid tert-butyl ester (4.80 g, 15.6 mmol) in anhydrous DMF (DMF) (40 mL). The resultant mixture is heated in an oil bath at 55° C. under nitrogen for 3 days. At ambient temperature, ethyl acetate (160 mL) and half-saturated aqueous sodium chloride (NaCl) (200 mL) are added to the mixture. The organic layer is separated, washed with half-saturated aqueous NaCl (200 mL), dried over magnesium sulfate, filtered, and concentrated to provide the title compound as a dark oil (3.88 g, 92% yield).

(C). Preparation of 4-(3-amino-propyl)-piperazine-1-carboxylic acid tert-butyl ester Triphenylphosphine (2.78 g, 10.6 mmol) is added to a stirred solution of 4-(3-azido-propyl)-piperazine-1-carboxylic acid tert-butyl ester (2.05 g, 7.61 mmol) in a solution of THF (10 mL)/acetonitrile (30 mL)/water (4 mL). The resultant mixture is stirred for 16 hours. After concentration and subsequent chromatography on silica gel, eluting with 2 M NH$_3$/CH$_3$OH in dichloromethane 0-20%, the title compound is obtained as a clear oil (1.76 g, 95% yield).

PREPARATION 3

5-(2-Aminoethyl)-hexahydropyrrolo[3,4-c]pyrrole-2-carboxylic acid tert-butyl ester Using the method of 4-(3-aminopropyl)-piperazine-1-carboxylic acid tert-butyl ester, the title compound is synthesized from hexahydropyrrolo[3,4-c]pyrrole-2-carboxylic acid tert-butyl ester.

PREPARATION 4

3-(4-Isopropylpiperazin-1-yl)-propylamine (A). Preparation of 2-[3-(4-isopropylpiperazin-1-yl)-propyl]-isoindole-1,3-dione N-(3-Bromopropyl)phthalimide (16.7 g, 62.4 mmol) is added to a stirred solution of 1-isopropyl-piperazine (8.00 g, 62.4 mmol) and diisopropylethylamine (8.06 g, 62.4 mmol) in anhydrous 1,4-dioxane (300 mL). The resultant mixture is heated in an oil bath at 90° C. for 20 hours. At ambient temperature, chloroform (300 mL) and half-saturated aqueous NaCl (200 mL) are added to the mixture. The organic layer is separated, dried over magnesium sulfate, filtered, and concentrated. The crude oil is subjected to chromatography on silica gel and eluted with 2 M NH$_3$/CH$_3$OH in dichloromethane 0-5% to provide the title compound as a tan oil (17.4 g, 87% yield).

(B). Preparation of 3-(4-isopropylpiperazin-1-yl)-propylamine

Hydrazine (8.63 g, 270 mmol) is added to a stirred suspension of 2-[3-(4-isopropylpiperazin-1-yl)-propyl]-isoindole-1,3-dione (17.0 g, 53.9 mmol) in anhydrous ethanol (400 mL). The resultant mixture is heated in an oil bath at 75° C. for 16 hours. At ambient temperature, dichloromethane (300 mL) is added to the mixture and the suspension is allowed to stir for 10 minutes. After filtration and concentration, the title compound is obtained as a tan oil (8.12 g, 81% yield).

Using the methods of 3-(4-isopropylpiperazin-1-yl)-propylamine, the following amines are synthesized from an appropriate N-(bromoalkyl)phthalimide and corresponding amines:

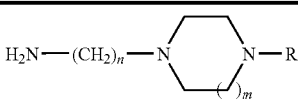

| Preparation No. | n | m | R |
|---|---|---|---|
| 5 | 2 | 1 | Me |
| 6 | 2 | 2 | Me |
| 7 | 3 | 1 | CH$_2$CH$_3$ |
| 8 | 3 | 1 | (CH$_2$)$_2$CH$_3$ |
| 9 | 3 | 1 | (CH$_2$)$_2$—OH |

PREPARATION 10

3-(3,5-cis-Dimethylpiperazin-1-yl)-propylamine

Using the method of 3-(4-isopropylpiperazin-1-yl)-propylamine, the title compound is obtained from N-(3-bromopropyl)phthalimide and 2,6-cis-dimethylpiperazine as a tan oil.

PREPARATION 11

3-(3,5-cis-Dimethyl-4-methylpiperazin-1-yl)-propylamine

Using the method of 3-(4-isopropylpiperazin-1-yl)-propylamine, 2-[3-(3,5-cis-dimethyl-piperazin-1-yl)-propyl]-isoindole-1,3-dione is prepared as a white solid (92% yield). To a stirred solution of this white solid (10.0 g, 33.1 mmol) in acetonitrile (120 mL) at ambient temperature is added formalin (27 mL, 331 mmol), the solution is allowed to stir for 10 minutes. Sodium cyanoborohydride (5.21 g, 82.9 mmol) and acetic acid (3 mL) are sequentially added to the reaction mixture and the resultant mixture is stirred for another 2 hours. After concentration, the crude product is dissolved in dichloromethane (150 mL), washed with saturated aqueous NaHCO$_3$ (60 mL×2), dried and concentrated. After chromatography on silica gel, eluting with 2 M NH$_3$/CH$_3$OH in dichloromethane 0-6%, 2-[3-(3,5-cis-dimethyl-4-methylpiperazin-1-yl)-propyl]-isoindole-1,3-dione is obtained as a tan oil (7.90 g, 75% yield).

To a stirred solution of this tan oil (7.0 g, 22 mmol) in anhydrous methanol (250 mL) is added hydrazine (5.69 g, 177 mmol), the resultant mixture is heated in an oil bath at 65° C. for 16 hours to form a suspension. The suspension is concentrated to 60 mL in volume. After filtration and concentration, the title compound is obtained as a tan oil (4.01 g, 97% yield).

Using the method of 3-(4-isopropylpiperazin-1-yl)-propylamine, the following compounds are prepared from N-(2-bromoethyl)phthalimide and corresponding amines and isolated as tan oils:

| Preparation No. | R |
|---|---|
| 12 |  |
| 13 | 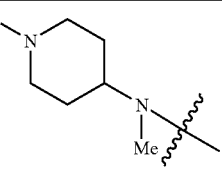 |

PREPARATION 14

4-(3-Aminopropyl)-piperidine-1-carboxylic acid tert-butyl ester (A). Preparation of 4-(3-hydroxypropyl)-piperidine-1-carboxylic acid tert-butyl ester Di-tert-butyl dicarbonate (3.66 g, 16.8 mmol) is added to a stirred solution of 3-piperidin-4-yl-propan-1-ol (1.60 g, 11.2 mmol) in anhydrous dichloromethane (20 mL) at ambient temperature under nitrogen. The resultant mixture is allowed to stir for 2 hours. The mixture is directly subjected to chromatography purification on silica gel and eluted with MeOH in dichloromethane 0-3% to give the title compound as a clear oil (2.40 g, 88% yield).

(B). Preparation of 4-(3-azidopropyl)-piperidine-1-carboxylic acid tert-butyl ester Methanesulfonyl chloride (0.690 mL, 8.92 mmol) is added to a stirred solution of 4-(3-hydroxy-propyl)-piperidine-1-carboxylic acid tert-butyl ester (1.67 g, 6.86 mmol) and collidine (1.27 mL, 9.61 mmol) in anhydrous dichloromethane (20 mL) at 0° C. under nitrogen. The resultant mixture is allowed to stir at 0° C. for 30 minutes, then at ambient temperature for 1.5 hours. The mixture is directly subjected to chromatography purification on silica gel and eluted with MeOH in dichloromethane 0-3%, to give the mesylate product (2.05 g). The mesylated product (0.730 g, 2.27 mmol) is dissolved in anhydrous DMF (8 mL), followed by the addition of NaN$_3$ (0.325 g, 5.00 mmol), and then the mixture is heated at 55° C. for 18 hours. At ambient temperature, the mixture is diluted with dichloromethane (40 mL) then it is washed with water (15 mL×3). The organic layer is dried over sodium carbonate and concentrated to give the title compound (0.566 g, 92% yield).

(C). Preparation of 4-(3-aminopropyl)-piperidine-1-carboxylic acid tert-butyl ester Triphenylphosphine (0.657 g, 2.50 mmol) is added to a stirred solution of 4-(3-azido-propyl)-piperidine-1-carboxylic acid tert-butyl ester (0.560 g, 2.09 mmol) in THF (2 mL)/CH$_3$CN (5 mL)/H$_2$O (1 mL) and the mixture is stirred at ambient temperature for 18 hours. After concentration and subsequent chromatography purification on silica gel, eluting with 2 M $NH_3$/MeOH in dichloromethane 0-15%, the title compound is obtained as a clear oil (0.420 g, 83% yield).

PREPARATION 15

3-(1-Methylpiperidin-4-yl)-propylamine (A). Preparation of 3-(1-methylpiperidin-4-yl)-propan-1-ol.

Formalin (6.33 g, 211 mmol) is added to a stirred solution of 3-(piperidin-4-yl)-propan-1-ol (3.02 g, 21.1 mmol) in acetonitrile (30 mL) at ambient temperature. The solution is allowed to stir for 20 minutes. Sodium cyanoborohydride (3.31 g, 52.7 mmol) and acetic acid (3 mL) are sequentially added to the reaction mixture and the resultant mixture is stirred for another 2 hours. After concentration, the crude product is dissolved in dichloromethane (150 mL), washed with saturated aqueous $NaHCO_3$ (60 mL×2), dried and concentrated. The crude product is subjected to chromatography on silica gel and eluted with 2 M $NH_3$/$CH_3OH$ in dichloromethane 0-15% to give the title compound as an oil (2.70 g).

(B). Preparation of 3-(1-methylpiperidin-4-yl)-propylamine

Using the method of 4-(3-aminopropyl)-piperidine-1-carboxylic acid tert-butyl ester, the title compound is prepared and isolated as an oil.

PREPARATION 16

4-(Benzo[b]thiophen-2-yl)-2-chloropyrimidine

Aqueous $Na_2CO_3$ solution (2 N, 45 mL) is added to a stirred mixture of thianaphtha-2-boronic acid (8.00 g, 44.8 mmol) and 2,4-dichloropyrimidine (6.69 g, 44.8 mmol) in 1,4-dioxane (100 mL) at 60° C. The resultant mixture is allowed to stir under nitrogen for 30 seconds before powdered [dppb]$PdCl_2$ (1.35 g, 2.24 mmol) is added to the mixture. The resultant mixture is immediately heated in an oil bath at 90° C. for 14 hours. At ambient temperature, 600 mL $CHCl_3$ and 400 mL half-saturated aqueous NaCl solution are added to the mixture. The organic layer is separated and the aqueous layer is further extracted with $CHCl_3$ (100 mL). The combined organic layers are dried over sodium sulfate ($Na_2SO_4$), filtered, and concentrated to give a wet solid. Methylene chloride (25 mL) and diethyl ether (10 mL) are added to the mixture and the suspension is sonicated and filtered to give a tan solid. The solid is then dissolved in 80 mL of warm dichloromethane and chromatographed on silica (ISCO Redi Sep column, 120 g) to give the title compound as a white solid (6.78 g, 57% yield).

Using the method of 4-(benzo[b]thiophen-2-yl)-2-chloropyrimidine, the following compounds are synthesized from thianaphtha-2-boronic acid and the corresponding 2,4-dichloropyrimidines:

| Preparation | Name |
| --- | --- |
| 17 | 4-Benzo[b]thiophen-2-yl-2-chloro-5-fluoropyrimidine |
| 18 | 4-Benzo[b]thiophen-2-yl-2-chloro-5-chloropyrimidine |
| 19 | 4-Benzo[b]thiophen-2-yl-2-chloro-5-methylpyrimidine |

PREPARATION 20

4-(Benzo[b]thiophen-2-yl)-5-bromo-2-chloropyrimidine n-Butyl lithium (20.7 mL, 1.6 M in hexane) is added dropwise to a stirred solution of benzo[b]thiophene (4.12 g, 30.1 mmol) in anhydrous THF (50 mL) at −78° C. under nitrogen. The resultant solution is allowed to stir at −78° C. for 15 minutes. The lithiated benzo[b]thiophene is then added via canula over 20 minutes to a stirred solution of 5-bromo-2-chloro-pyrimidine (5.95 g, 30.1 mmol) in anhydrous THF (100 mL) at −30° C. Upon the completion of the addition, the solution is allowed to stir at −30° C. for an additional 30 minutes then at 0° C. for another 30 minutes. The reaction is quenched with acetic acid (1.99 g, 33.1 mmol), then after 5 minutes, it is treated with a solution of DDQ (7.17 g, 31.6 mmol) in anhydrous THF (150 mL) in portions at 10° C. The mixture is stirred for 20 minutes at 10° C. before it is concentrated to give a dark solid. The solid is then suspended in chloroform (500 mL) and the suspension is sonicated and filtered through a pad of silica. Additional 700 mL chloroform is used to wash the solid. The combined filtrates are concentrated to give a solid. The solid is re-suspended in dichloromethane (20 mL)/diethyl ether (20 mL) and the suspension is sonicated and filtered to give the title compound as a yellowish solid (9.62 g, 98% yield).

PREPARATION 21

2-(5-Bromo-2-chloropyrimidin-4-yl)-benzo[b]thiophene-4-carboxylic acid cyclopropylamide (A). Preparation of 2-(5-bromo-2-chloropyrimidin-4-yl)-benzo[b]thiophene-4-carboxylic acid Butyllithium (2.5 M in hexane, 14.1 mL) is added dropwise to a stirred solution of benzo[b]thiophene-4-carboxylic acid (3.00 g, 16.8 mmol) in anhydrous THF (50 mL) at −78° C. under nitrogen. The resultant mixture is allowed to stir for 45 minutes at −78° C. before it is added, via cannula, to a stirred cold solution of 5-bromo-2-chloropyrimidine (3.26 g, 16.8 mmol) in anhydrous THF (50 mL) at −30° C. Upon the completion of the addition, the reaction mixture is stirred for 30 minutes at −30° C., then at ambient temperature for another 1.5 hours. Acetic acid (2.4 mL) is added to the reaction mixture, after 5 minutes, followed by the addition of 2,3-dichloro-5,6-dicyano-1,4-benzoquinone (4.01 g, 17.7 mmol) dissolved in THF (10 mL). The mixture is allowed to stir for 10 minutes before it is treated dropwise with HCl (37%, 30 mL), then the mixture is stirred for another 1 hour. THF is evaporated off and the mixture becomes a suspension. The solid is filtered off, washed with water (100 mL×2), and then dried under vacuum. The dry solid is suspended in dichloromethane (45 mL) and ethanol (5 mL) and stirred for 30 minutes. After filtration, the solid is resuspended in ether (50 mL) and the suspension is stirred for another 30 minutes. After filtration and vacuum drying, the title compound is obtained as a yellow solid. (2.64 g, 42% yield).

(B). Preparation of 2-(5-bromo-2-chloropyrimidin-4-yl)-benzo[b]thiophene-4-carboxylic acid cyclopropylamide Diisopropylethylamine (1.19 mL, 6.82 mmol), 1-[3-(dimethylamino)propyl]-3-ethylcarbodiimide hydrochloride (0.650 g, 3.41 mmol) and 1-hydroxybenzotriazole (0.460 g, 3.41 mmol) are sequentially added to a stirred suspension of 2-(5-bromo-2-chloropyrimidin-4-yl)-benzo[b]thiophene-4-carboxylic acid (1.20 g, 3.25 mmol) in anhydrous dichloromethane (25 mL) at ambient temperature under nitrogen.

The resultant light suspension is treated with cyclopropylamine (0.190 g, 3.41 mmol), then the reaction mixture is allowed to stir for 5 hours. The reaction mixture is diluted with dichloromethane (50 mL) before it is washed with water (100 mL). The aqueous layer is extracted with dichloromethane (100 mL×2) to ensure no precipitation is present in the aqueous layer. The combined organic layers are concentrated and then resuspended in dichloromethane (1 mL)/diethyl ether (9 mL). After sonication and subsequent filtration, the solid is washed with additional dichloromethane (1 mL)/diethyl ether (9 mL) and dried to provide the title compound (1.10 g, 97% yield).

PREPARATION 22

Racemic 3-(3-aminopropyl)-piperidine-1-carboxylic acid tert-butyl ester

Using the method of 4-(3-aminopropyl)-piperidine-1-carboxylic acid tert-butyl ester, the compound is prepared as an oil.

PREPARATION 23

(3-(4-Benzhydryl-2,6-cis-dimethylpiperazin-1-yl)-propylamine

Benzhydryl bromide (4.33 g, 17.5 mmol) is added to s stirred solution of 2,6-cis-dimethylpiperazine (2.00 g, 17.5 mmol) and diisopropylethylamine (2.94 g, 22.8 mmol) in anhydrous dichloromethane (50 mL) at 0° C. The resultant mixture is allowed to stir overnight. After concentration and subsequent chromatography on silica gel, eluting with 2 M $NH_3/CH_3OH$ in dichloromethane: 1-3%, benzhydryl-3,5-cis-dimethyl-piperazine is obtained as a white solid (3.0 g, 61% yield).

N-(3-Bromopropyl)phthalimide (2.50 g, 9.33 mmol) is added to a stirred solution of benzhydryl-3,5-cis-dimethylpiperazine (2.61 g, 9.33 mmol) and diisopropylethylamine (1.81 g, 14.0 mmol) in N,N-dimethylacetamide (25 mL). The resultant mixture is heated at 120° C. for 48 hours. After concentration and subsequent chromatography on silica gel, eluting with 2 M $NH_3/CH_3OH$ in dichloromethane: 0-1%, 2-[3-(4-benzhydryl-2,6-cis-dimethylpiperazin-1-yl)-propyl]-isoindole-1,3-dione is obtained as a brown oil (1.98 g, 45% yield).

Hydrazine (1.10 g, 34.2 mmol) is added to a stirred solution of 2-[3-(4-benzhydryl-2,6-cis-dimethylpiperazin-1-yl)-propyl]-isoindole-1,3-dione (1.98 g, 4.28 mmol) in ethanol (70 mL). The mixture is heated at 70° C. for 12 hours to form a suspension. At room temperature the mixture is filtered and the filtrate is concentrated to give 3-(4-benzhydryl-2,6-cis-dimethyl-piperazin-1-yl)-propylamine (1.02 g, 71% yield) as an oil.

PREPARATION 24

(3-(4-Methyl-[1,4]diazepan-1-yl)-propylamine

Using the method of 3-(4-isopropylpiperazin-1-yl)-propylamine, 3-(4-methyl-[1,4]diazepan-1-yl)-propylamine is synthesized as an oil from 1-methyl-[1,4]diazepane.

PREPARATION 25

2-(2-Chloro-5-fluoropyrimidin-4-yl)-benzo[b]thiophene-4-carboxylic acid cyclopropylamide (A). Preparation of 2-(2-chloro-5-fluoropyrimidin-4-yl)-benzo[b]thiophene-4-carboxylic acid An aqueous 2N $Na_2CO_3$ solution (36 mL) is added dropwise to a stirred solution of (4-carboxybenzo[b]thiophen-2-yl)boronic acid (3.63 g, 18.8 mmol) and 2,4-dichloro-5-fluoropyrimidine (3.00 g, 18.0 mmol) in ethyleneglycol dimethyl ether (50 mL) at room temperature under nitrogen atmosphere. Upon the completion of addition, dichlorobis(triphenylphosphine)palladium(II) (0.22 g, 3% mol) is added in one portion, then the reaction mixture is heated at 100° C. overnight. The mixture is cooled to 10° C., then 37% HCl (10 mL) is added in portions to form a suspension. After filtration and washing with water, the solid is dried under vacuum. The dry solid is suspended in 30 mL of dichloromethane/ethanol (10:1), sonicated, filtered, and dried again to provide 2-(2-chloro-5-fluoropyrimidin-4-yl)-benzo[b]thiophene-4-carboxylic acid (2.95 g, 48% yield).

(B). Preparation of 2-(2-chloro-5-fluoropyrimidin-4-yl)-benzo[b]thiophene-4-carboxylic acid cyclopropylamide Using the method of 2-(2,5-dichloropyrimidin-4-yl)-benzo[b]thiophene-4-carboxylic acid cyclopropylamide, 2-(2-chloro-5-fluoropyrimidin-4-yl)-benzo[b]thiophene-4-carboxylic acid cyclopropylamide is synthesized from 2-(2-chloro-5-fluoropyrimidin-4-yl)-benzo[b]thiophene-4-carboxylic acid and cyclopropylamine as a solid (89% crude yield)

PREPARATION 26

2-(2-Chloro-5-methylpyrimidin-4-yl)-benzo[b]thiophene-4-carboxylic acid cyclopropylamide Using the method of 2-(2-chloro-5-fluoropyrimidin-4-yl)-benzo[b]thiophene-4-carboxylic acid cyclopropylamide, 2-(2-chloro-5-methylpyrimidin-4-yl)-benzo[b]thiophene-4-carboxylic acid cyclopropylamide is prepared and isolated as a tan solid.

PREPARATION 27

2-(2,2,6,6-Tetramethylpiperidin-4-ylidene)-ethylamine

Potassium tert-butoxide (9.40 g, 83.7 mmol) is suspended in THF (175 mL), then cooled to 0° C. Cyanomethyl-phosphonic acid diethyl ester (16.0 g, 90.2 mmol) is added over five minutes. After stirring for 20 minutes, 2,2,6,6-tetramethylpiperidin-4-one (10.0 g, 64.4 mmol) dissolved in THF (50 mL) is added to the reaction mixture at −78° C. After the addition is complete the cold bath is removed. The reaction is stirred overnight, then enough water is added to dissolve any suspended salts. The organic layer is separated and the aqueous layer is extracted with EtOAc. The organic layers are combined, concentrated, then the residue is chromatographed on silica gel, eluting with 0-3% 2M $NH_3/MeOH$ in dichloromethane to give 3.77 g of (2,2,6,6-tetramethylpiperidin-4-ylidene)-acetonitrile (33% yield).

The above product (1.13 g, 6.34 mmol) is dissolved in anhydrous diethyl ether (15 mLl), cooled to 0° C. and 1.0 M lithium aluminum hydride in diethyl ether is slowly added to the reaction mixture. The cold bath is removed and the reaction mixture is stirred for 18 hours. The reaction mixture is quenched with MeOH until gas evolution ceases. Saturated Rochelle's salt (45 mL) is added and the reaction stirred vigorously for 2 hours. 4 equivalents of 5 N NaOH is added and the reaction stirred for an hour. Diethyl ether (45 mL) is added and the two layers are separated. The aqueous layer is extracted with diethyl ether again, then the organic layers are combined, dried over $Na_2SO_4$, filtered, and concentrated to give 785 mg (68% yield) of 2-(2,2,6,6-tetramethylpiperidin-4-ylidene)-ethylamine.

PREPARATION 28

4-(2-Aminoethyl)-4-methylpiperidine-1-carboxylic acid tert-butyl ester (A). Preparation of 4-methyl-piperidine-1,4-dicarboxylic acid 1-tert-butyl ester 4-methyl ester Piperidine-1,4-dicarboxylic acid 1-tert-butyl ester 4-methyl ester (1.00 g, 4.11 mmol) is dissolved in THF (10 mL) and cooled to −78° C. 2.0 M Lithium diisopropyl amide in THF is added dropwise, then stirred for 1 hour. Iodomethane (0.563 mL, 9.04 mmol) is added and the mixture is stirred for 1 hour. The cold bath is removed and the reaction stirred for an additional 0.5 hour. The reaction mixture is quenched with saturated ammonium chloride (3 mL), concentrated, taken up in dichloromethane, and chromatographed on silica gel, eluting with EtOAc in dichloromethane 0-5%, to give the title compound as a slightly yellow oil. (680 mg, 64% yield).

(B). Preparation of 4-hydroxymethyl-4-methylpiperidine-1-carboxylic acid tert-butyl ester 4-Methylpiperidine-1,4-dicarboxylic acid 1-tert-butyl ester 4-methyl ester (1.48 g, 5.73 mmol) is dissolved in THF (15 mL) and cooled to 0° C. 1.0 M lithium aluminum hydride in THF (6.30 mL, 6.30 mmol) is added dropwise. After 1.25 hours the reaction is quenched with MeOH, then stirred with saturated Rochelle's salt until two layers form. The two layers are separated and the aqueous layer is treated with 5 N NaOH and extracted with diethyl ether. The organic layers are combined, concentrated, and chromatographed using silica gel, eluting with EtOAc in hexanes 0-40%, to give the title compound (1.27 g, 97% yield).

(C). Preparation of 4-methanesulfonyloxymethyl-4-methylpiperidine-1-carboxylic acid tert-butyl ester To 4-hydroxymethyl-4-methylpiperidine-1-carboxylic acid tert-butyl ester (1.25 g, 5.45 mmol) and pyridine (0.661 mL, 8.18 mmol) in dichloromethane (10 mL) at 0° C. is added methanesulfonyl chloride (0.593 mL, 7.63 mmol). After 3 hours, one additional equivalent of methanesulfonylchloride and pyridine are added. After 1 hour the reaction mixture is concentrated, then EtOAc and water are added. The organic layer is concentrated and chromatographed on silica gel eluting with MeOH in dichloromethane 0-3% to give the title compound as a yellow oil (1.60 g, 95% yield).

(D). Preparation of 4-cyanomethyl-4-methylpiperidine-1-carboxylic acid tert-butyl ester To 4-methanesulfonyloxymethyl-4-methylpiperidine-1-carboxylic acid tert-butyl ester (0.440 g, 1.43 mmol) dissolved in DMSO (3 mL) is added potassium cyanide (0.373 g, 5.73 mmol). The mixture is heated to 130° C. for 18 hours. The reaction mixture is cooled and diluted with EtOAc and water. The organic layer is concentrated, taken up in MeOH and concentrated again to give the title compound as a brown oil (263 mg, 77% yield).

(E). Preparation of 4-(2-aminoethyl)-4-methylpiperidine-1-carboxylic acid tert-butyl ester To 5% $Rh/Al_2O_3$ (0.600 g) suspended in water (2 mL) is added ethanol (5 mL), 4-cyanomethyl-4-methylpiperidine-1-carboxylic acid tert-butyl ester (0.258 g, 1.083 mmol) dissolved in ethanol (10 mL) and 28% $NH_3$ (aq) (0.25 mL). The reaction mixture is subjected to 50 psi hydrogen gas and stirred at room temperature for 18 hours. The reaction mixture is filtered to remove the catalyst, then the filtrate is concentrated and chromatographed on silica gel, eluting with 0-10% (2 M $NH_3$ in MeOH) in dichloromethane to give the title compound (130 mg, 50% yield).

PREPARATION 29

2-(2,2,6,6-Tetramethyl-piperidin-4-yl)-ethylamine

To 2-(2,2,6,6-tetramethylpiperidin-4-ylidene)-ethylamine (0.480 g, 2.63 mmol) in MeOH (5 mL) is added 10% Pd/C (48 mg) and 5 N HCl (2.63 mL, 13.2 mmol). At 50 psi hydrogen gas at 50° C. the reaction mixture is stirred for 18 hours. The reaction is filtered to remove the catalyst and resubjected to the reaction conditions using $RhClPPh_3$ (0.26 mmol). Due to incomplete reaction the mixture is diluted with water, concentrated to remove any organic solvent, filtered to remove any solids, and then concentrated again. The residue is dissolved in acetic acid and resubjected to the hydrogenation conditions using 100 mg of palladium black and 50 psi hydrogen gas at 50° C. for 18 hours. The mixture of products is not easily purified, so the crude mixture is treated with di-tert-butyl dicarbonate in dichloromethane and then purified by silica gel chromatography using a high enough percentage of 2 M $NH_3$ in MeOH in dichloromethane to isolate 240 mg of [2-(2,2,6,6-tetramethyl-piperidin-4-yl)-ethyl]-carbamic acid tert-butyl ester. [2-(2,2,6,6-Tetramethyl-piperidin-4-yl)-ethyl]-carbamic acid tert-butyl ester (240 mg, 0.844 mmol) is dissolved in 2:1 MeOH:dichloromethane (10.5 mL) and HCl (g) is bubbled for 5 minutes. After 1 hour, the reaction mixture is concentrated to give a foam (219 mg). The foam is dissolved in MeOH and loaded onto an SCX 5 g resin column. The column is washed with MeOH, then the product is released with 7 M $NH_3$ in MeOH. After concentration the title compound is obtained and used without further purification (138 mg).

PREPARATION 30

4-(3-Aminopropyl)-4-methylpiperidine-1-carboxylic acid tert-butyl ester (A). Preparation of 4-(2-cyanoacetyl)-4-methylpiperidine-1-carboxylic acid tert-butyl ester Acetonitrile (3.07 mL, 58.4 mmol) is added to THF (75 mL). At −78° C. 1.6 M BuLi in hexanes is slowly added. After 15 minutes, 4-methylpiperidine-1,4-dicarboxylic acid 1-tert-butyl ester 4-methyl ester (6.83 g, 26.5 mmol) dissolved in THF (75 mL) is added dropwise. After 1 hour 2.2 equivalents of 5N HCl is added at −78° C. The reaction is warmed to room temperature and concentrated to about 50 mL volume. EtOAc (50 mL) and saturated aqueous sodium chloride (25 mL) are added to the mixture. The organic layer is separated, dried over $Na_2SO_4$, concentrated, and chromatographed on silica gel, eluting with 0-20% EtOAc in dichloromethane, to give the title compound (4.80 g, 68% yield).

(B). Preparation of 4-(2-cyano-1-hydroxyethyl)-4-methylpiperidine-1-carboxylic acid tert-butyl ester To 4-(2-cyanoacetyl)-4-methylpiperidine-1-carboxylic acid tert-butyl ester (6.20 g, 23.3 mmol) dissolved in dry MeOH (95 mL) is added sodium borohydride (1.76 g, 46.6 mmol) portion wise over 10 minutes. The ice bath is removed after 1 hour and stirring is continued for 1 hour. The reaction mixture is concentrated, then dissolved in EtOAc (50 mL) and some MeOH. The mixture is washed with 1N HCl (25 mL). Saturated aqueous sodium chloride (25 mL) is added and the organic layer is dried over $Na_2SO_4$, then concentrated. The residue is dissolved in dichloromethane, loaded onto a silica gel column, and chromatographed. After pooling fractions and concentrating, the mixture is dissolved in MeOH and concentrated again to give the title compound as a slightly yellow oil (5.89 g, 95% yield).

(C). Preparation of 4-(2-cyano-1-methanesulfonyloxyethyl)-4-methylpiperidine-1-carboxylic acid tert-butyl ester and 4-(2-cyanovinyl)-4-methylpiperidine-1-carboxylic acid tert-butyl ester To 4-(2-cyano-1-hydroxyethyl)-4-methylpiperidine-1-carboxylic acid tert-butyl ester (4.24 g, 15.8 mmol) and pyridine (3.07 mL, 39.5 mmol) dissolved in dichloromethane (45 mL) at 0° C. is added methanesulfonyl chloride (3.45 mL, 42.6 mmol). After 1 hour, the reaction is not complete and is warmed to room temperature. After 18 hours at room temperature 1 equivalent of pyridine and 1 equivalent of methanesulfonyl chloride is added and stirred for 4 hours. The reaction mixture is diluted with EtOAc and washed several times with saturated $NaHCO_3$. The organic layer is dried over $Na_2SO_4$, filtered and concentrated to give crude 4-(2-cyano-1-methanesulfonyloxy-ethyl)-4-methylpiperidine-1-carboxylic acid tert-butyl ester. Assuming 100% yield, 4-(2-cyano-1-methanesulfonyloxyethyl)-4-methylpiperidine-1-carboxylic acid tert-butyl ester (5.47 g, 15.8 mmol) and triethylamine (11.0 mL, 79 mmol) are dissolved in MeOH (60 mL) and heated at 70° C. for 1 hour and concentrated. The residue is dissolved in EtOAc and washed with water, then concentrated and chromatographed using 100% dichloromethane to give cis/trans-4-(2-cyanovinyl)-4-methylpiperidine-1-carboxylic acid tert-butyl ester (3.93 g, 99% yield) as a clear oil.

(D). Preparation of 4-(3-aminopropyl)-4-methylpiperidine-1-carboxylic acid tert-butyl ester Cis/trans-4-(2-cyanovinyl)-4-methylpiperidine-1-carboxylic acid tert-butyl ester (1.00 g, 4.0 mmol), 5% $Rh/Al_2O_3$ (0.500 g) and 28% aqueous $NH_3$ (1.25 mL) are heated at 35° C. in ethanol (20 mL) and 50 psi hydrogen gas for 18 hours. The reaction mixture is filtered through Celite®, concentrated, and chromatographed with 0-20% (2M $NH_3$ in MeOH) in dichloromethane to give the title compound as a clear oil (0.65 g, 63% yield).

PREPARATION 31

Racemic 4-(3-amino-1-hydroxypropyl)-4-methylpiperidine-1-carboxylic acid tert-butyl ester Using the method of the preparation of 4-(3-aminopropyl)-4-methylpiperidine-1-carboxylic acid tert-butyl ester, 4-(3-amino-1-hydroxypropyl)-4-methylpiperidine-1-carboxylic acid tert-butyl ester is prepared from 4-(2-cyano-1-hydroxyethyl)-4-methyl-piperidine-1-carboxylic acid tert-butyl ester.

PREPARATION 32

2-(2-Chloro-5-methylpyrimidin-4-yl)-benzo[b]thiophene-6-carboxylic acid

A). Preparation of 2,-(2-chloro-5-methylpyrimidine-4-yl)-benzo[b]thiophene-6-carboxylic acid methyl ester Benzo[b]thiophene-6-carboxylic acid methyl ester (7.30 g, 38.0 mmol) is dissolved in THF (100 mL) and cooled to −78° C. Triisopropylborate (9.5 mL) and lithium diisopropylamine solution (23 mL of 2.0 M solution) are added sequentially and the reaction mixture is allowed to slowly warm to room temperature over 3 hours. The reaction is stirred at room temperature for 1 hour at which time 2,4-dichloro-5-methylpyrimidine (6.82 g, 41.8 mmol), 1,1'-bis(diphenylphosphino)ferrocene (1.05 g, 1.90 mmol), palladium (II) acetate (0.44 g, 1.9 mmol), and sodium carbonate (57 mL of 2.0 N solution) are added. The reaction is heated at 70° C. for 20 hours. After the reaction solution cools to room temperature, water (100 mL) and dichloromethane (100 mL) are added. The resulting precipitate is filtered and washed with dichloromethaneto give a tan solid (4.55 g). The combined organic layers are dried over anhydrous sodium sulfate and concentrated. The resulting solid is subjected to chromatography on silica gel, eluting with EtOAc/hexanes 5-50%, to give 1.16 g of additional material of the title compound (5.71 g total, 47% yield). ES+(m/z) 319 [M+H].

(B). Preparation of 2-{5-methyl-2-[3-(4-methylpiperazin-1-yl)-propylamino]-pyrimidin-4-yl}-benzo[b]thiophene-6-carboxylic acid methyl ester A mixture of 2-(2-chloro-5-methylpyrimidin-4-yl)-benzo[b]thiophene-6-carboxylic acid methyl ester (2.08 g, 6.50 mmol) and 1-(3-aminopropyl)-4-methylpiperazine (3.00 g, 19.0 mmol) in 1,4-dioxane (40 mL) is heated at 90° C. for 20 hours. The solvent is evaporated and the resulting residue is subjected to chromatography on silica gel, eluting with 2M $NH_3/CH_3OH$ in dichloromethane 0-8%, to give the title compound (1.30 g, 72% yield). ES+(m/z) 460 [M+H].

(C). Preparation of 2-{5-methyl-2-[3-(4-methyl-piperazin-1-yl)-propylamino]-pyrimidin-4-yl}-benzo[b]thiophene-6-carboxylic acid tri-hydrochloride 2-{5-Methyl-2-[3-(4-methylpiperazin-1-yl)-propylamino]-pyrimidin-4-yl}-benzo[b]thiophene-6-carboxylic acid methyl ester (1.31 g, 2.98 mmol) is dissolved in methanol (30 mL), THF (30 mL) and water (10 mL) and lithium hydroxide solution (4.6 mL of 2.0 M solution) is added. The solution is heated at 70° C. for 4.5 hours and 5 N HCl (9 mL) is added in one portion while still heating the solution. The solution is cooled to room temperature and the resulting solid is filtered and washed with methanol. The solid is dried at 60° C. in a vacuum oven for 4 hours to give the title compound (1.43 g, 97% yield). ES+(m/z) 426 [M+H].

PREPARATION 33

Preparation of 2-(2-chloro-5-methylpyrimidin-4-yl)-benzo[b]thiophene-6-carboxylic acid methylamide Using the method of Preparations (A)-(D) in 2-{5-chloro-2-[3-(4-methylpiperazin-1-yl)-propylamino]-pyrimidin-4-yl}-benzo[b]thiophene-4-carboxylic acid cyclopropylamide tri-hydrochloride, the title compound is synthesized from 6-bromo-benzo[b]thiophene as a tan solid.

PREPARATION 34

2-[5-Chloro-2-(3-piperidin-4-ylpropylamino)-pyrimidin-4-yl]-benzo[b]thiophene-6-carboxylic acid methylamide (A). Preparation of 2-(2,5-dichloropyrimidin-4-yl)-benzo[b]thiophene-6-carboxylic acid methylamide Using the method of 2-(2,5-dichloropyrimidin-4-yl)-benzo[b]thiophene-4-carboxylic acid cyclopropylamide, the title compound is synthesized from 6-bromo-benzo[b]thiophene as a tan solid.

(B). Preparation of 2-[5-chloro-2-(3-piperidin-4-ylpropylamino)-pyrimidin-4-yl]-benzo[b]thiophene-6-carboxylic acid methylamide 4-(3-Aminopropyl)-piperidine-1-carboxylic acid tert-butyl ester (0.72 g, 3.0 mmol) is added to a stirred suspension of 2-(2,5-dichloropyrimidin-4-yl)-benzo[b]thiophene-6-carboxylic acid methylamide (0.40 g, 1.2 mmol) and diisopropylethylamine (0.38 g, 3.0 mmol) in anhydrous 1,4-dioxane (15 mL) at room temperature under nitrogen. The resultant mixture is heated in an oil bath at 90° C. for 12 hours. At room temperature, the mixture is concentrated and the resultant solid is washed with diethyl ether (20 mL) to give a yellow solid. The solid is suspended in dichloromethane (5 mL), followed by the successive addition of triethylsilane (0.7 mL) and TFA (4 mL). The resultant yellow solution is stirred for 2 hours. After concentration to dryness, the crude product is dissolved in MeOH (20 mL)/dichloromethane (10 mL) and the solution is treated in portions with 2N LiOH (4.2 mL) to form a suspension. After concentration and subsequent chromatography on silica gel, eluting with 2.0 M NH$_3$/MeOH in dichloromethane 0-10%, the title compound is obtained as a yellow solid (0.26 g, yield 49%). ES+(m/z) 444 ($^{35}$Cl) and 446 ($^{37}$Cl) [M+H].

PREPARATION 35

[2-(2-Chloro-5-methylpyrimidin-4-yl)-benzo[b]thiophen-6-yl]-morpholin-4-yl-methanone Using the method of 2-(2,5-dichloropyrimidin-4-yl)-benzo[b]thiophene-4-carboxylic acid cyclopropylamide, the title compound is synthesized from 6-bromo-benzo[b]thiophene as a tan solid.

PREPARATION 36

[4-(6-Aminomethyl-benzo[b]thiophen-2-yl)-pyrimidin-2-yl]-[3-(4-methyl-piperazin-1-yl)-propyl]-amine (A). Preparation of C-benzo[b]thiophen-6-ylmethylamine Benzo[b]thiophene-6-carbonitrile (9.70 g, 61.1 mmol) is dissolved in THF (400 mL) and cooled to 0-5° C. Lithium aluminum hydride (183 mL of 1.0 M solution in THF) is added dropwise over 30 minutes and the reaction is stirred for 20 hours while warming to 25° C. The reaction is cooled with an ice bath and water (6.94 mL) is slowly added followed by 15% sodium hydroxide (6.94 mL) and water (20.83 mL). The resulting precipitate is filtered and washed with diethyl ether. The filtrate is concentrated to give the title compound as a colorless oil (8.16 g, 82% yield). ES+(m/z) 164 [M+H].

(B). Preparation of benzo[b]thiophen-6-ylmethylcarbamic acid tert-butyl ester

Benzo[b]thiophen-6-yl-methylamine (7.80 g, 47.8 mmol) is dissolved in THF (400 mL) and di-tert-butyl dicarbonate (13.9 g, 63.5 mmol) is added. After stirring for 20 hours, the solvent is removed. The resulting residue is dissolved in dichloromethane and the solvent is evaporated to give a pale yellow solid (8.0 g, 64% yield).

(C). Preparation of [2-(2-chloropyrimidin-4-yl)-benzo[b]thiophen-6-ylmethyl]-carbamic acid tert-butyl ester Benzo[b]thiophen-6-ylmethyl-carbamic acid tert-butyl ester (3.6 g, 13.8 mmol) is dissolved in THF (100 mL) and cooled to −78° C. Triisopropylborate (8.5 mL) is added, followed by lithium diisopropylamine solution (27 mL of 2.0 M solution), and the reaction is allowed to slowly warm to room temperature over two hours. The reaction is stirred at room temperature for two hours at which time 2,4-dichloropyrimidine (4.59 g, 30.8 mmol), 1,1'-bis(diphenylphosphino)ferrocene (388 mg, 0.700 mmol), palladium (II) acetate (164 mg, 0.730 mmol) and sodium carbonate (28 mL of 2.0 N solution) are added. The reaction is heated for 20 hours at 70° C. After the reaction solution is cooled to 25° C., water (100 mL) is added. The mixture is extracted with dichloromethane and the extracts are evaporated. The resulting solid is subjected to chromatography on silica gel, eluting with EtOAc/hexanes 5-50%, to give the title compound (1.47 g, 28% yield). ES+(m/z) 376 ($^{35}$Cl) and 378 ($^{37}$Cl) [M+H].

(D). Preparation of (2-{2-[3-(4-methylpiperazin-1-yl)-propylamino]-pyrimidin-4-yl}-benzo[b]thiophen-6-ylmethyl)-carbamic acid tert-butyl ester A mixture of [2-(2-chloropyrimidin-4-yl)-benzo[b]thiophen-6-ylmethyl]-carbamic acid tert-butyl ester (1.47 g, 3.90 mmol) and 1-(3-aminopropyl)-4-methylpiperazine (1.36 g, 8.60 mmol) in dioxane (38 mL) is refluxed for 3 hours. The solvent is removed and the residue is subjected to chromatography on silica gel, eluting with 2.0 M NH$_3$/MeOH in CHCl$_3$ 0-10%, to obtain the title compound (1.36 g, 70% yield). ES+(m/z) 497 [M+H].

(E). Preparation of [4-(6-aminomethyl-benzo[b]thiophen-2-yl)-pyrimidin-2-yl]-[3-(4-methyl-piperazin-1-yl)-propyl]-amine (2-{2-[3-(4-Methylpiperazin-1-yl)-propylamino]-pyrimidin-4-yl}-benzo[b]thiophen-6-ylmethyl)-carbamic acid tert-butyl ester (1.36 g, 2.74 mmol) is dissolved in dichloromethane (20 mL) and TFA (3.2 mL) is added. After stirring for 20 hours, methanol is added and the mixture is passed through an SCX column. After eluting with methanol to remove the salts, 20% 2.0 M NH$_3$/MeOH/EtOAC is used to elute the product which is then passed through a 15 g silica gel column using the same solvent system. The title compound is obtained as a yellow solid (0.73 g, 68% yield). ES+(m/z) 397 [M+H].

PREPARATION 37

[4-(6-Aminomethylbenzo[b]thiophen-2-yl)-5-chloropyrimidin-2-yl]-[3-(4-methylpiperazin-1-yl)-propyl]-amine (A). Preparation of 2-(2,5-dichloropyrimidin-4-yl)benzo[b]thiophene-6-carbonitrile To a −70° C. solution of 6-cyanobenzothiophene (7.98 g, 50.1 mmol) and triisopropylborate (10.4 g, 55.1 mmol) in THF (100 mL) is added lithium diisopropylamide (27.6 mL, 2 M solution in heptane/THF/ethylbenzene, 55.1 mmol)

dropwise over 10 minutes. The mixture is stirred for 3 hours and then allowed to slowly warm, over 2 hours, to room temperature. To the mixture is then added 2,4,5-trichloropyrimidine (9.19 g, 50.1 mmol), 2 N Na$_2$CO$_3$ (50 mL, 100 mmol), 1,1'-bis(diphenylphosphino)-ferrocene (1.39 g, 2.51 mmol) and palladium(II) acetate (563 mg, 2.51 mmol) and the resultant mixture is heated to reflux for 18 hours. Upon cooling to room temperature, the mixture is concentrated under reduced pressure, extracted from water (100 mL) with dichloromethane (3×200 mL). The combined organic extracts are concentrated under reduced pressure to yield a beige solid (18.7 g). The crude material is sonicated in diethyl ether (200 mL) and filtered to provide the title compound as a light beige solid (14.8 g, 97% yield).

(B). Preparation of 2-{5-chloro-2-[3-(4-methylpiperazin-1-yl)-propylamino]-pyrimidin-4-yl}-benzo[b]thiophene-6-carbonitrile Using the method of (2-{2-[3-(4-methylpiperazin-1-yl)-propylamino]-pyrimidin-4-yl}-benzo[b]thiophen-6-ylmethyl)-carbamic acid tert-butyl ester, the title compound is synthesized from 2-(2,5-dichloropyrimidin-4-yl)benzo[b]thiophene-6-carbonitrile and 1-(3-aminopropyl)-4-methylpiperazine and isolated as a solid. ES+(m/z) 427 ($^{35}$Cl) and 429 ($^{37}$Cl) [M+H].

(C). Preparation of [4-(6-aminomethyl-benzo[b]thiophen-2-yl)-5-chloropyrimidin-2-yl]-[3-(4-methylpiperazin-1-yl)-propyl]-amine Into a pressure vessel is added 2-(5-chloro-2-(3-(4-methylpiperazin-1-yl)propylamino)pyrimidin-4-yl)benzo[b]thiophene-6-carbonitrile (6.23 g, 14.6 mmol), acetic acid (25 mL), MeOH (500 mL) and Rainey Nickel (2.5 mL). The mixture is hydrogenated at 60 psi for 12 hours, filtered and concentrated under reduced pressure. The resulting gum is dissolved in water (200 mL) and extracted with diethyl ether (200 mL). The aqueous layer is basified to pH=14 with 5 N NaOH and extracted with dichloromethane (2×200 mL). The organic layer is concentrated under reduced pressure and subjected to chromatographic purification on silica gel, eluting with 7:2.5:0.5 EtOAc/MeOH/Et$_3$N in dichloromethane: 0-100%, to give the crude material as a mixture of products (3.53 g). This material is subjected to reverse phase purification, 10-25% 0.1% TFA in CH$_3$CN/0.1% TFA in water on a C18 Symmetry column, to yield a yellow solid (2.55 g). This solid is dissolved in 2.5 N NaOH (100 mL) and extracted with dichloromethane (3×100 mL). The organic layers are concentrated to afford the title compound as a yellow solid (808 mg, 13% yield). ES+(m/z) 431 ($^{35}$Cl) and 433 ($^{37}$Cl) [M+H].

PREPARATION 38

4-(6-Bromobenzo[b]thiophen-2-yl)-2,5-dichloropyrimidine

A solution of 6-bromobenzo[b]thiophene (5.00 g, 23.5 mmol) in THF (50 mL) is cooled to −70° C. Lithium diisopropylamide (12.9 mL, 2M solution in heptane/THF/ethylbenzene, 25.8 mmol) is added dropwise over 7 minutes and the mixture is allowed to warm to room temperature overnight. To the mixture is added 2,4,5-trichloropyrimidine (4.31 g, 23.5 mmol), 2 N Na$_2$CO$_3$ (23.6 mL, 47.2 mmol), 1,1'-bis(diphenylphosphino)ferrocene (651 mg, 1.17 mmol) and palladium(II) acetate (263 mg, 1.17 mmol) and the mixture is heated to reflux for 21 hours. Upon cooling to room temperature, the mixture is concentrated under reduced pressure, extracted from water (100 mL) with dichloromethane (3×150 mL) and 10% MeOH/dichloromethane (2×150 mL). The combined organic extracts are concentrated under reduced pressure to yield a brown solid (9.15 g). The crude material is sonicated in diethyl ether (200 mL) and filtered to provide the title compound as a light brown solid (6.66 g, 79% yield).

PREPARATION 39

[4-(6-Bromobenzo[b]thiophen-2-yl)-pyrimidin-2-yl]-[3-(4-methylpiperazin-1-yl)-propyl]-amine Using the method of 4-(6-bromobenzo[b]thiophen-2-yl)-2,5-dichloropyrimidine, the title compound is synthesized from 6-bromobenzo[b]thiophene and isolated as a solid.

PREPARATION 40

[4-(6-Aminobenzo[b]thiophen-2-yl)-5-methylpyrimidin-2-yl]-[3-(4-methylpiperazin-1-yl)-propyl]-amine (A). Preparation of benzo[b]thiophen-6-ylamine A mixture of 6-bromobenzo[b]thiophene (16.0 g, 76.0 mmol), benzophenone imine (16.6 g, 91.5 mmol), tris(dibenzylidineacetone)palladium(0) (0.72 g, 0.80 mmol), 1,1'-bis(diphenylphosphino)ferrocene (1.3 g, 2.3 mmol) and sodium tert-butoxide (10.8 g, 112 mmol) in toluene is refluxed for 20 hours. The solvent is evaporated and the residue is chromatographed on silica, eluting with dichloromethane) to give the title compound (1.52 g, 11% yield).

(B). Preparation of benzo[b]thiophen-6-ylcarbamic acid tert-butyl ester

A mixture of benzo[b]thiophen-6-ylamine (1.33 g, 8.93 mmol), di-tert-butyldicarbonate (2.65 g, 12.1 mmol) and dimethylaminopyridine (0.35 g, 2.8 mmol) in THF (80 mL) is stirred for 20 hours. Solvent is evaporated and the residue is chromatographed on silica gel, eluting with EtOAc in hexanes 0-40%, to give the title compound as a brown oil (1.51 g, 68% yield).

(C). Preparation of [2-(2-chloro-5-methylpyrimidin-4-yl)-benzo[b]thiophen-6-yl]-carbamic acid tert-butyl ester Benzo[b]thiophen-6-yl-carbamic acid tert-butyl ester (1.06 g, 4.30 mmol) is dissolved in THF (40 mL) and cooled to −78° C. Lithium diisopropylamine solution (8.5 mL of 2.0 M solution) and triisopropylborate (6.0 mL, 26 mmol) are added. The reaction is stirred at −78° C. for 90 minutes before the cooling bath is removed. After stirring for three hours, 2,4-dichloro-5-methylpyrimidine (0.74 g, 4.5 mmol), 1,1'-bis (diphenylphosphino) ferrocene (120 mg, 0.220 mmol), palladium (II) acetate (50.4 mg, 0.220 mmol), and sodium carbonate (9.5 mL of 2.0 N solution) are added. The reaction is heated at 70° C. for 20 hours. After the reaction solution is cooled to 25° C., water (100 mL) is added. The mixture is extracted with dichloromethane and the extracts are evaporated. The resulting solid is chromatographed on silica gel, eluting with EtOAc in hexanes 5-50%, to give the title compound as a yellow solid (0.32 g, 20% yield).

(D). Preparation of (2-{5-methyl-2-[3-(4-methylpiperazin-1-yl)-propylamino]-pyrimidin-4-yl}-benzo[b]thiophen-6-yl)-carbamic acid tert-butyl ester A mixture of [2-(2-chloro-5-methylpyrimidin-4-yl)-benzo[b]thiophen-6-yl]-carbamic acid tert-butyl ester (0.32 g, 0.85 mmol) and 1-(3-aminopropyl)-4-methylpiperazine (0.41 g, 2.6 mmol) in 1,4-dioxane (15 mL) is refluxed for 48 hours. Solvent is removed and the residue is chromatographed on silica gel, eluting with 2.0 M NH$_3$/MeOH in dichloromethane 0-10%, to obtain the title compound as a yellow solid (0.33 g, 78% yield). ES+(m/z) 497 [M+H].

(E). Preparation of [4-(6-aminobenzo[b]thiophen-2-yl)-5-methylpyrimidin-2-yl]-[3-(4-methylpiperazin-1-yl)-propyl]-amine (2-{5-Methyl-2-[3-(4-methylpiperazin-1-yl)-propylamino]-pyrimidin-4-yl}-benzo[b]thiophen-6-yl)-carbamic acid tert-butyl ester (0.33 g, 0.66 mmol) is dissolved in dichloromethane (6 mL) and TFA (0.78 mL) is added. The solution is stirred for 20 hours before adding methanol. The mixture is passed through an SCX column. After eluting with methanol, 20% of 2.0 M $NH_3$/MeOH in EtOAc is used to elute the product which is then chromatographed on silica gel, eluting with 2.0 M $NH_3$/MeOH in dichloromethane 0-15%, to give the title compound as a yellow oil. (166 mg, 64% yield). ES+(m/z) 397 [M+H].

PREPARATION 41

Piperidine-4-carboxylic acid {3-[5-chloro-4-(4-cyclopropylcarbamoyl-benzo[b]thiophen-2-yl)-pyrimidin-2-ylamino]-propyl}-amide (A). Preparation of 2-(2,5-dichloropyrimidin-4-yl)-benzo[b]thiophene-4-carboxylic acid cyclopropylamide A suspension of 2-(2,5-dichloropyrimidin-4-yl)-benzo[b]thiophene-4-carboxylic acid (5.00 g, 15.4 mmol) in dichloromethane (100 mL) is treated at room temperature with cyclopropylamine (1.20 mL, 17.3 mmol) in the presence of N,N-diisopropylethylamine (3.00 mL, 17.2 mmol), 1-(3-diethylaminopropyl)-3-ethylcarbodiimide hydrochloride (3.34 g, 17.4 mmol), and 1-hydroxybenzotriazole (2.33 g, 17.2 mmol) for 20 hours. Water (20 mL) is then added, and after stirring for 20 minutes, the mixture is filtered, and dried. The obtained solid is suspended in dichloromethane (50 mL), stirred for 2 hours, filtered, and dried to provide the title compound (5.60 g, 99%).

(B). Preparation of 2-[2-(3-aminopropylamino)-5-chloropyrimidin-4-yl]-benzo[b]thiophene-4-carboxylic acid cyclopropylamide A stirred suspension of 2-(2,5-dichloropyrimidin-4-yl)-benzo[b]thiophene-4-carboxylic acid cyclopropylamide (5.59 g, 15.3 mmol) in 1.4-dioxane (60 mL), (3-amino-propyl)-carbamic acid tert-butyl ester (2.70 mL, 2.69 mg, 15.5 mmol) in N,N-diisopropylethylamine (5.20 mL, 3.86 g, 29.9 mmol) is heated at 97° C. for 120 hours. The mixture is then cooled to room temperature, diluted with dichloromethane (120 mL), filtered, washed with dichloromethane (2×25 mL), and dried to provide {3-[5-chloro-4-(4-cyclopropylcarbamoyl-benzo[b]thiophen-2-yl)-pyrimidin-2-ylamino]-propyl}-carbamic acid tert-butyl ester (5.00 g, 65%). This intermediate (4.99 g, 9.94 mmol) is suspended in methanol (120 mL) and treated with 10% aqueous HCl (10 mL) and the mixture is heated at 100° C. for 24 hours. The mixture is then cooled to room temperature, quenched with 2 N NaOH (20 mL), filtered, washed with $H_2O$ (60 mL), dichloromethane (60 mL), and diethyl ether (60 mL), and dried to provide the title compound (3.99 g, 99%).

(C). Preparation of piperidine-4-carboxylic acid {3-[5-chloro-4-(4-cyclopropylcarbamoyl-benzo[b]thiophen-2-yl)-pyrimidin-2-ylamino]-propyl}-amide A suspension of 2-[2-(3-aminopropylamino)-5-chloropyrimidin-4-yl]-benzo[b]thiophene-4-carboxylic acid cyclopropylamide (500 mg, 1.24 mmol) in dichloromethane (30 mL) is treated at room temperature with piperidine-1,4-dicarboxylic acid mono-tert-butyl ester (340 mg, 1.48 mmol) in the presence of N,N-diisopropylethylamine (0.220 mL, 163 mg, 1.26 mmol), 1-(3-diethylaminopropyl)-3-ethylcarbodiimide hydrochloride (240 mg, 1.25 mmol), and 1-hydroxybenzotriazole (171 mg, 1.21 mmol) for 24 hours. The mixture is then diluted with dichloromethane (30 mL), filtered, washed with $H_2O$ (30 mL), and diethyl ether (30 mL), and dried to provide 4-{3-[5-chloro-4-(4-cyclopropylcarbamoyl-benzo[b]thiophen-2-yl)-pyrimidin-2-ylamino]-propylcarbamoyl}-piperidine-1-carboxylic acid tert-butyl ester (700 mg, 92%). A stirred mixture of this intermediate (695 mg, 1.13 mmol) in dichloromethane (25 mL) is treated at room temperature with TFA (2.5 mL) for 72 hours. The mixture is then concentrated under reduced pressure, and subjected to chromatographic purification on silica gel, eluting with 2 M $NH_3$/MeOH in dichloromethane: 16-40%, to provide the title compound (492 mg, 85% yield).

PREPARATION 42

2-(2,5-Dichloropyrimidin-4-yl)-7-methoxybenzo[b]thiophene-4-carboxylic acid cyclopropylamide (A). Preparation of 7-methoxybenzo[b]thiophene To a solution of 7-bromobenzo[b]thiophene (10.0 g, 46.9 mmol) in dry DMF (234 mL) is added copper iodide (8.90 g, 46.9 mmol), followed by the addition of sodium methoxide (30% in MeOH, 176 mL, 938 mmol) at room temperature under nitrogen atmosphere. The mixture is heated at 100° C. for 2 hours and cooled to room temperature. Water (400 mL) is added and the mixture is extracted with diethyl ether (4×200 mL). Organic layers are washed with cooled water (3×75 mL), saturated aqueous sodium chloride (100 mL), dried (MgSO4), and concentrated to give the title compound as yellow oil (7.58 g, 98% yield).

(B). Preparation of 7-methoxybenzo[b]thiophene-4-carboxylic acid

Phosphorous oxychloride (7.1 mL, 76.7 mmol) is added dropwise to a cooled dry DMF (13.2 mL, 170.4 mmol) at such rate that the temperature does not exceed 5° C. After 30 minutes at this temperature, a solution of 7-methoxybenzo[b]thiophene (7.00 g, 42.6 mmol) in dry DMF (2 mL) is added dropwise. The stirring continues at 5° C. for 30 minutes and at room temperature for 45 minutes. Afterward, the mixture is heated to 117° C. and then at 90° C. for 2 hours, cooled to 0° C., and neutralized with a solution of sodium acetate (62 g) in water (300 mL). The resulting mixture is extracted with diethyl ether (5×150 mL) and the organic layers are washed with cooled water (5×100 mL), saturated aqueous sodium chloride (100 mL), dried (MgSO4) and concentrated. The crude material is purified on slica gel (hexanes/EtOAc 9:1) to give 7-methoxybenzo[b]thiophene-4-carbaldehyde as a yellow solid (5.5 g, 68% yield). To a stirred solution of the intermediate (14.9 g, 77.5 mmol) in acetone (300 mL) is slowly added a solution of potassium permanganate (14.9 g, 94.3 mmol) in water (525 mL) at 0° C. and the mixture is stirred for 75 minutes. Then, isopropanol (100 mL) is added and the mixture is divided in two portions. Each portion is treated with HCl (100 mL, 12%), diluted with water (300 mL) and extracted with EtOAc (3×300 mL). Organic layers are washed with water (300 mL), saturated aqueous sodium chloride (300 mL), dried (MgSO4), and concentrated. Residue is collected and diluted with EtOAc (600 mL) and the suspension is warmed to 70° C. and filtered to give the title compound as a white solid (10.3 g, 63% yield). At temperature, the filtrate forms a suspension. After filtration, an additional 3.2 g is obtained. ES+(m/z) 207 [M–H].

(C). Preparation of 2-(2,5-dichloropyrimidin-4-yl)-7-methoxybenzo[b]thiophene-4-carboxylic acid To a –78° C. solution of diisopropylamine (2.9 mL, 20.9 mmol) in dry THF (28 mL) is added a solution of n-butyllithium (13.1 mL, 20.9 mmol, 1.6 M in hexane) under nitrogen atmosphere and the mixture is stirred for 30 minutes. The mixture is added to a suspension of 2-(2,5-dichloropyrimidin-4-yl)-7-methoxybenzo[b]thiophene-4-carboxylic acid (1.36 g, 6.53 mmol) in dry THF (40 mL) at –78° C. The resultant mixture is warmed to 0° C. and the stirring continues for 2 hours. The mixture is cooled to –40° C. and triisopropylborate (5.4 mL, 23.5 mmol) is added dropwise. The mixture is warmed to room temperature where the stirring continues for another 2 hours. A solution of HCl (12%, 40 mL) is added at 0° C. and the mixture is stirred at room temperature for 30 minutes. Water (40 mL) is added and the suspension is filtered off. The solid is washed with water to give 2-(2,5-dichloropyrimidin-4-yl)-7-methoxybenzo[b]thiophene-4-carboxylic acid-2-boronic acid as a white solid (1.56 g, 95% yield).

To a solution of 2,4,5-trichloropyrimidine (1.24 g, 6.76 mmol) in dry dimethoxyethane (6 mL) are successively added dichlorobis(triphenylphosphine) palladium (II) (146 mg, 0.21 mmol), sodium carbonate (2 N in water, 12.2 mL, 24.6 mmol) at room temperature under nitrogen atmosphere. The mixture is heated to 45° C. for 10 minutes and a suspension of 2-(2,5-dichloropyrimidin-4-yl)-7-methoxybenzo[b]thiophene-4-carboxylic acid-2-boronic acid (1.55 g, 6.15 mmol) in dimethoxyethane (24 mL) is added over 1 hour period. The mixture is stirred at 45° C. for 1.5 hours then cooled to room temperature. The mixture is acidified to pH 2 with a solution of HCl (12%) and diluted with water (50 mL). The mixture is filtered off and the solid is washed with water and diethyl ether to provide the title compound as a yellow solid (2.5 g) which is used in the next step without further purification.

(D). Preparation of 2-(2,5-dichloropyrimidin-4-yl)-7-methoxybenzo[b]thiophene-4-carboxylic acid cyclopropylamide To a stirred suspension of 2-(2,5-dichloropyrimidin-4-yl)-7-methoxybenzo[b]thiophene-4-carboxylic acid (2.50 g, 3.07 mmol) is added diisopropylethylamine (1.12 mL, 6.44 mmol), N-(3-dimethylaminopropyl)-N'-ethylcarbodiimide hydrochloride (617 mg, 3.22 mmol) and 1-hydroxybenzotriazole (435 mg, 3.22 mmol) at room temperature under nitrogen atmosphere. The mixture is treated with cyclopropylamine (184 mg, 3.22 mmol) and stirred at room temperature for 1 day. The mixture is diluted with dichloromethane (60 mL) and washed with water (3×30 mL). The organic phase suspension is filtered off to give a yellow solid which is washed with dichloromethane and water to give the title compound as a yellow solid (880 mg, 72% yield).

PREPARATION 43

[5-Chloro-4-(6-triisopropylsilanylstlfanyl-benzo[b]thiophen-2-yl)-pyrimidin-2-yl]-[3-(4-methylpiperazin-1-yl)-propyl]-amine To a solution of [4-(6-bromobenzo[b]thiophen-2-yl)-5-chloropyrimidin-2-yl]-[3-(4-methylpiperazin-1-yl)-propyl]-amine (600 mg, 1.24 mmol) in toluene (3 mL) is added tetrakis(triphenylphosphine)palladium(0) (100 mg, 0.0870 mmol) and triisopropylsilanethiol potassium salt (previously prepared from triisopropylsilanethiol using essentially the method described in Tetrahedron Lett., 35, (20), 3221-3224, (1994)) (285 mg, 1.24 mmol) at room temperature under a nitrogen atmosphere. The mixture is heated to 100° C. for 2 hours then cooled to room temperature. Water (50 mL) is added and the mixture is extracted with EtOAc (3×20 mL). The organic layers are dried (MgSO$_4$) and concentrated to give the title compound as a sticky red solid (660 mg).

PREPARATION 44

2-{5-Methyl-2-[3-(4-methylpiperazin-1-yl)-propylamino]-pyrimidin-4-yl}-benzo[b]thiophene-6-sulfonic acid benzhydryl-amide (A). Preparation of benzo[b]thiophene-6-sulfonic acid benzhydrylamide To a suspension of magnesium (1.14 g, 46.9 mmol) in dry THF (50 mL) is added iodine (100 mg) followed by slow addition of 6-bromobenzo[b]thiophene (5.00 g, 23.5 mmol) in dry THF (100 mL) at 64° C. (internal temperature) under a nitrogen atmosphere. During the addition, dry toluene (20 mL) is added to the mixture. When addition is completed, the mixture is heated at 68° C. (internal temperature) for 3 hours then cooled to –60° C. where a stream of sulfur dioxide is passed through the solution for 10 minutes. The mixture is allowed to warm to room temperature, the sulfur dioxide bubbling continues for an additional 5 minutes, and the mixture is stirred for 45 minutes. After filtration and concentration, a reddish solid is obtained (8.0 g), which is diluted with dichloromethane (235 mL), treated with N-chlorosuccinimide (3.45 g, 25.8 mmol) at room temperature, and stirred for 2 hours. After filtration and concentration, a reddish solid is obtained (5.8 g), which is diluted with dichloromethane (234 mL), treated with aminodiphenylmethane (20.2 mL, 117 mmol) at 0° C. and the mixture is stirred for 1 hour. Water (200 mL) is added and the mixture is extracted with dichloromethane (3×200 mL). The organic layers are dried (MgSO4) and concentrated. The crude product is suspended in dichloromethane/hexane before it is filtered to give the title compound as a white solid. The filtrate is concentrated and the residue is chromatographed on silica gel (dichloromethane) to give a second crop of title compound (total 2.52 g). ES+ (m/z) 378 [M–H].

(B). Preparation of 2-(2-chloro-5-methylpyrimidin-4-yl)-benzo[b]thiophene-6-sulfonic acid benzhydrylamide To a solution of diisopropylamine (2.09 mL, 14.87 mmol) in dry THF (10 mL) is added a solution of n-butyllithium (1.6 M in hexane, 9.14 mL, 14.62 mmol) at –78° C. under a nitrogen atmosphere, the mixture is stirred for 30 minutes. A solution of benzo[b]thiophene-6-sulfonic acid benzhydrylamide (925 mg, 2.44 mmol) and triisopropylborate (2.87 mL, 12.43 mmol) in dry THF (10 mL) is added. The mixture is slowly warmed to 10° C. over 1 hour and stirred at room temperature for 30 minutes. A solution of sodium carbonate (2 M in water, 3.78 mL) is added followed by the addition of 2,4 dichloro5-methylpyrimidine (517 mg, 3.17 mmol) and (1,1'-bis(diphenylphosphino)ferrocene)palladium (II) chloride (99.6 mg, 0.122 mmol). The mixture is heated at 60° C. for 1.5 hours then cooled to room temperature. Water (40 mL) is added and the mixture is extracted with EtOAc (3×40 mL). The organic layers are dried (MgSO4) and concentrated. The residue is chromatographed on silica gel, eluting with hexanes/EtOAc 90:10 to 40:60, to give the title compound as a yellow solid (457 mg, 37% yield).

(C). Preparation of 2-{5-methyl-2-[3-(4-methylpiperazin-1-yl)-propylamino]-pyrimidin-4-yl}-benzo[b]thiophene-6-sulfonic acid benzhydryl-amide To a stirred suspension of 2-(2-chloro-5-methylpyrimidin-4-yl)-benzo[b]thiophene-6-sulfonic acid benzhydrylamide (457 mg, 0.903 mmol) in dry 1,4-dioxane (4.5 mL) is added diisopropylethylamine (0.315 mL, 1.81 mmol) and 1-(3-aminopropyl)-4-methylpiperazine (213 mg, 1.35 mmol). The mixture is heated at 97° C. for 1 day. After concentration and subsequent chromatographic purification on silica gel, eluting with 2 M $NH_3$/MeOH in dichloromethane: 0-10%, the title compound is obtained as a yellow solid (317 mg, 57% yield). ES+(m/z) 627 [M+H].

PREPARATION 45

2,5-Dichloro-4-(6-methylsulfanylbenzo[b]thiophen-2-yl)-pyrimidine (A). Preparation of 6-methylsulfanylbenzo[b]thiophene A mixture of 6-bromobenzo[b]thiophene (2.0 g, 9.4 mmol) and sodium thiomethoxide (1.30 g, 18.8 mmol) in DMF (15 mL) is stirred at 90° C. under nitrogen for 6 hours. The reaction is cooled to room temperature, extracted with ethyl acetate and saturated aqueous sodium chloride, washed with 2 N aqueous NaOH solution, saturated aqueous sodium chloride, dried over $Na_2SO_4$, filtered, and evaporated. The residue is purified by chromatography on silica gel, eluting with ethyl acetate:hexanes 3:7, to give the title product as a red liquid (1.41 g) which is used for next reaction without further purification.

(B). Preparation of 2,5-dichloro-4-(6-methylsulfanylbenzo[b]thiophen-2-yl)-pyrimidine To a stirred solution of 6-methylsulfanylbenzo[b]thiophene (1.41 g, 7.82 mmol) and triisopropylborate (1.80 mL, 7.82 mmol) in THF (20 mL) at −78° C. under nitrogen is added lithium diisopropylamine (4.3 mL, 2 M solution). The reaction is allowed to slowly warm to room temperature. An aqueous solution of $Na_2CO_3$ (2.50 g, 23.5 mmol, in 11 mL of water) is added, followed by the addition of 2,4,5-trichloropyrimidine (1.58 g, 8.60 mmol) and [1,1-bis(diphenylphospheno)ferrocene]palladium (II) chloride (0.32 g, 0.39 mmol). The reaction mixture is heated at 60° C. under nitrogen for 1 hour. After being cooled to room temperature, the suspension is filtered and the solid is washed with water and ethyl acetate then dried under vacuum. The crude product is purified by chromatography on silica gel, eluting with dichloromethane:hexanes 2:8 to 3:7, to give the title product as a light yellow solid (0.19 g).

PREPARATION 46

2-(2,5-Dichloropyrimidin-4-yl)-benzo[b]thiophene-4-carboxylic acid amide

Diisopropylethylamine (0.574 mL) is added to a stirred suspension of 2-(2,5-dichloropyrimidin-4-yl)-benzo[b]thiophene-4-carboxylic acid (1.02 g, 3.14 mmol) in anhydrous dichloromethane (20 mL) at 0° C. under nitrogen to form a clear solution. The solution is treated dropwise with 7M $NH_3$/MeOH (0.493 mL, 3.45 mmol) to form a suspension. Powdered 1H-benzotriazol-1-yloxytris(dimethylamino)phosphonium hexafluorophosphate (1.46 g, 3.30 mmol) is added to the mixture and the resultant mixture is allowed to stir at 0° C. for 2 hours and at room temperature for 5 hours. Diethyl ether (15 mL) is added in small portions to the mixture. The mixture is stirred for another 20 minutes before filtration. After drying, the title compound is obtained as a tan solid and is used without further purification (0.994 g).

PREPARATION 47

(2-(5-Bromo-2-chloropyrimidin-4-yl)-benzo[b]thiophene-4-carboxylic acid [bis-(4-methoxyphenyl)-methyl]-amide Using the method of 2-(2-chloro-5-methylpyrimidin-4-yl)-benzo[b]thiophene-4-carboxylic acid [bis-(4-methoxyphenyl)-methyl]-amide, the title compound is synthesized from 2-(5-bromo-2-chloropyrimidin-4-yl)-benzo[b]thiophene-4-carboxylic acid as a tan solid.

PREPARATION 48

(R)-4-(3-Aminopropyl)-3-methylpiperazine-1-carboxylic acid tert-butyl ester

N-(3-Bromopropyl)phthalimide (6.50 g, 24.2 mmol) is added to a stirred solution of (R)-3-methyl-piperazine-1-carboxylic acid tert-butyl ester (4.85 g, 24.2 mmol) and diisopropylethylamine (4.70 g, 36.4 mmol) in anhydrous 1,4-dioxane (50 mL). The resultant mixture is heated in an oil bath at 90° C. for 20 hours. After concentration, the mixture is subject to chromatography on silica gel, eluting with 2 M $NH_3$/$CH_3OH$ in dichloromethane 1-3%, to provide the intermediate product (7.5 g, 79% yield).

The intermediate product (7.54 g, 19.5 mmol) is dissolved in anhydrous ethanol (250 mL) then treated with hydrazine (3.75 g, 117 mmol). The stirring mixture is heated in an oil bath at 70° C. for 16 hours to form a white suspension. At room temperature the mixture is filtered and the filtrate is concentrated to give a mixture of solid and oil. The mixture is suspended in ethanol (10 mL) and diethyl ether (50 mL). After filtration and concentration, the title compound is obtained as a tan oil (4.72 g, 93% yield).

Using the method of (R)-4-(3-aminopropyl)-3-methylpiperazine-1-carboxylic acid tert-butyl ester, the following compounds are synthesized from the corresponding methylpiperazine-1-carboxylic acid tert-butyl ester

| Preparation | Compound |
| --- | --- |
| Preparation 49 | (R)-4-(2-Aminoethyl)-3-methylpiperazine-1-carboxylic acid tert-butyl ester |
| Preparation 50 | (S)-4-(3-Aminopropyl)-3-methylpiperazine-1-carboxylic acid tert-butyl ester |
| Preparation 51 | (S)-4-(3-Aminopropyl)-2-methylpiperazine-1-carboxylic acid tert-butyl ester |

PREPARATION 52

4-(3-Aminopropyl)-4-ethylpiperidine-1-carboxylic acid tert-butyl ester (A). Preparation of 4-ethylpiperidine-1,4-dicarboxylic acid 1-tert-butyl ester 4-methyl ester Using the method of 4-methylpiperidine-1,4-dicarboxylic acid 1-tert-butyl ester 4-methyl ester, the title compound is synthesized from piperidine-1,4-dicarboxylic acid 1-tert-butyl ester 4-methyl ester and isolated as a tan oil.

(B). Preparation of 4-(3-aminopropyl)-4-ethylpiperidine-1-carboxylic acid tert-butyl ester Using the method of 4-(3-aminopropyl)-4-methylpiperidine-1-carboxylic acid tert-butyl ester, the title compound is synthesized from 4-ethylpiperidine-1,4-dicarboxylic acid 1-tert-butyl ester 4-methyl ester and isolated as a clear oil.

PREPARATION 53

Racemic 3-(3-aminopropyl)-piperidine-1-carboxylic acid tert-butyl ester (A). Preparation of racemic 3-(3-methanesulfonyloxypropyl)-piperidine-1-carboxylic acid tert-butyl ester Using the method of 4-(3-azidopropyl)-piperidine-1-carboxylic acid tert-butyl ester, the title compound is synthesized from racemic 3-piperidin-3-ylpropan-1-ol and isolated as an oil.

(B). Preparation of racemic 3-(3-aminopropyl)-piperidine-1-carboxylic acid tert-butyl ester Potassium phthalimide (7.79 g, 42.1 mmol) is added to a stirred solution of racemic 3-(3-methanesulfonyloxypropyl)-piperidine-1-carboxylic acid tert-butyl ester (9.00 g, 28.0 mmol) in DMF (60 mL). The mixture is allowed to stir at 55° C. for 16 hours. At room temperature, the mixture is concentrated, the oil is diluted in ethyl acetate (50 mL), and the solution is washed with water (50 mL). The organic layer is concentrated and the crude product is chromatographed on silica gel, eluting with ethyl acetate in hexane 0-25%, to give 3-[3-(1,3-dioxo-1,3-dihydroisoindol-2-yl)-propyl]-piperidine-1-carboxylic acid tert-butyl ester (9.84 g, 94% yield). A stirred solution of this intermediate (9.00 g, 24.2 mmol) in ethanol (400 mL) is treated with hydrazine (4.65 g, 145 mmol). The mixture is heated at 50° C. for 16 hours to form a white suspension. At room temperature the suspension is quickly filtered and the filtrate is concentrated to give the oil containing a small amount of white solid. This mixture is diluted in ethanol (10 mL and diethyl ether (50 mL), filtered, and concentrated to provide the title compound as an oil (5.0 g, 85% yield).

PREPARATION 54

Racemic 4-(3-aminopropyl)-3-isopropylpiperazine-1-carboxylic acid tert-butyl ester (A). Preparation of racemic 3-isopropylpiperazine-1-carboxylic acid tert-butyl ester Di-tert-butyl dicarbonate (7.37 g, 33.8 mmol) is added to a stirred solution of racemic 2-isopropylpiperazine (4.80 g, 37.5 mmol) in anhydrous dichloromethane (50 mL) at 0° C., then the mixture is stirred at room temperature for 16 hours. After concentration and subsequent chromatographic purification on silica gel, eluting with 2 M $NH_3$/MeOH in dichloromethane 1-3%, the title compound is isolated as oil (5.3 g, 62% yield).

(B). Preparation of racemic 4-(3-aminopropyl)-3-isopropylpiperazine-1-carboxylic acid tert-butyl ester Using the method of 3-(4-isopropylpiperazin-1-yl)-propylamine, the title compound is synthesized from racemic 3-iso propyl-piperazine-1-carboxylic acid tert-butyl ester and isolated as a tan oil.

PREPARATION 55

(A). Preparation of 2-(2,5-dichloropyrimidin-4-yl)-benzo[b]thiophene-4-carboxylic acid methyl ester Using the method of 2-(2-chloropyrimidin-4-yl)-benzo[b]thiophene-4-carboxylic acid methyl ester, the title compound is synthesized from benzo[b]thiophene-4-carboxylic acid methyl ester and 2,4,5-trichloropyrimidine and isolated as a solid.

(B). Preparation of 2-{5-chloro-2-[3-(4-methylpiperazin-1-yl)-propylamino]-pyrimidin-4-yl}-benzo[b]thiophene-4-carboxylic acid methyl ester A stirred suspension of 2-(2,5-dichloropyrimidin-4-yl)-benzo[b]thiophene-4-carboxylic acid methyl ester (440 mg, 1.30 mmol) in 1,4-dioxane (10 mL) is treated with 3-(4-methyl-piperazin-1-yl)- propylamine (610 mg, 3.90 mmol) and diisopropylethylamine (500 mg, 3.90 mmol), the resultant mixture is heated at 90° C. under nitrogen for 16 hours. After concentration and subsequent chromatographic purification on silica gel, eluting with 2 M $NH_3$/MeOH in dichloromethane 1-10%, the title compound is isolated as a solid (310 mg, 51% yield).

(C). Preparation of 2-{5-chloro-2-[3-(4-methylpiperazin-1-yl)-propylamino]-pyrimidin-4-yl}-benzo[b]thiophene-4-carboxylic acid tri-hydrochloride Aqueous 2 N LiOH (1.1 mL, 2.2 mmol) is added to a stirred solution of 2-{5-chloro-2-[3-(4-methylpiperazin-1-yl)-propylamino]-pyrimidin-4-yl}-benzo[b]thiophene-4-carboxylic acid methyl ester (280 mg, 0.610 mmol) in water (3 mL), MeOH (6 mL) and THF (12 mL). The mixture is heat at 70° C. for 2 hours. While at 70° C., 5 N HCl (1 mL) is added to the solution, then the solution is allowed to cool to room temperature. After concentration, the yellow solid is suspended in THF (20 mL), sonicated, filtered, and dried to give the title compound as a solid (320 mg, 94% yield).

PREPARATION 56

2-[5-Methyl-2-(2-piperidin-4-ylethylamino)-pyrimidin-4-yl]-benzo[b]thiophene-6-carboxylic acid dimethylamide A stirred mixture of 2-(2-chloro-5-methylpyrimidin-4-yl)-benzo[b]thiophene-6-carboxylic acid dimethylamide (473 mg, 1.43 mmol), 4-(2-aminoethyl)-piperidine-1-carboxylic acid tert-butyl ester (814 mg, 3.56 mmol) and diisopropylethylamine (0.747 mL, 4.29 mmol) in 1,4-dioxane (5 mL) is heated at 97° C. under nitrogen for 2 days. At room temperature the mixture is concentrated and the crude product is chromatographed on silica gel, eluting with MeOH in dichloromethane 0-2%, to give 4-{2-[4-(6-dimethylcarbamoyl-benzo[b]thiophen-2-yl)-5-methylpyrimidin-2-ylamino]-ethyl}-piperidine-1-carboxylic acid tert-butyl ester. The intermediate is then subject to deprotection by dissolving in dichloromethane (20 mL) and treating with triethylsilane (0.9 mL) and TFA (4 mL). The resultant yellow solution is stirred at room temperature for 1 hour. After concentration and subsequent chromatography on silica gel, eluting with 2.0 M $NH_3$/MeOH in dichloromethane 3-12%, the fractions containing the desired product are collected and concentrated to give yellow foam. This foam is dissolved in MeOH (20 mL), treated with 0.5 N LiOH (20 mL) then concentrated to give the crude product of the title compound as yellow foam. It is used for next reductive methylation without further purification.

EXAMPLE 1

[4-(Benzo[b]thiophen-2-yl)-pyrimidin-2-yl]-[3-(4-methylpiperazin-1-yl)-propyl]-amine tri-hydrochloride

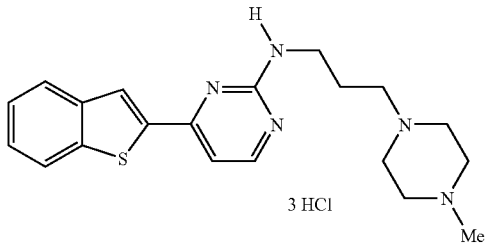

1-(3-Aminopropyl)-4-methylpiperazine (3.02 g, 19.2 mmol) is added to a stirred suspension of 4-(benzo[b]thiophen-2-yl)-2-chloro-pyrimidine (2.06 g, 8.34 mmol) in anhydrous 1,4-dioxane (25 mL) at ambient temperature under nitrogen. The resultant mixture is heated in an oil bath at 95° C. for 28 hours. At ambient temperature the mixture is concentrated and subject to chromatographic purification on silica gel, eluting with 2 M $NH_3/CH_3OH$ in dichloromethane 0-6%, to give the free base of the title compound as a white solid (2.83 g, 92% yield).

The above free base (1.42 g, 3.86 mmol) is dissolved in methanol (10 mL)/dichloromethane (15 mL). A small stream of anhydrous HCl gas is slowly bubbled through the stirred solution for 2 minutes, then the resulting yellow solution is concentrated to give a yellow solid. The yellow solid is resuspended in methanol (5 mL), while being sonicated, it is diluted with diethyl ether (25 mL). After filtration and drying, the title compound is obtained as a yellow solid (1.85 g, 100% yield). ES+(m/z) 368 [M+H].

Using methods similar to [4-(benzo[b]thiophen-2-yl)-pyrimidin-2-yl]-[3-(4-methylpiperazin-1-yl)-propyl]-amine tri-hydrochloride, the following compounds are synthesized and isolated as free base or HCl salt:

| Ex. | Compound | MS (ES+) m/z [M + H] |
|---|---|---|
| 2 | [4-(Benzo[b]thiophen-2-yl)-pyrimidin-2-yl]-[3-(4-isopropylpiperazin-1-yl)-propyl]-amine | 396 |
| 3 | [4-(Benzo[b]thiophen-2-yl)-5-chloropyrimidin-2-yl]-[3-(3,5-dimethyl-piperazin-1-yl)-propyl]-amine | 415 ($^{35}Cl$), 417 ($^{37}Cl$) |
| 4 | [4-(Benzo[b]thiophen-2-yl)-5-chloropyrimidin-2-yl]-[3-(4-methyl-piperazin-1-yl)-propyl]-amine | 402 ($^{35}Cl$), 404 ($^{37}Cl$) |
| 5 | [4-(Benzo[b]thiophen-2-yl)-5-chloropyrimidin-2-yl]-[3-(3,5-dimethylpiperazin-1-yl)-propyl]-amine tri-hydrochloride | 429 ($^{35}Cl$), 431 ($^{37}Cl$) |
| 6 | [4-(Benzo[b]thiophen-2-yl)-5-bromopyrimidin-2-yl]-[3-(3,5-dimethylpiperazin-1-yl)-propyl]-amine tri-hydrochloride | 460 ($^{79}Br$), 462 ($^{81}Br$) |
| 7 | [4-(Benzo[b]thiophen-2-yl)-5-bromopyrimidin-2-yl]-[3-(4-methyl-piperazin-1-yl)-propyl]-amine | 446 ($^{79}Br$), 448 ($^{81}Br$) |
| 8 | [4-(Benzo[b]thiophen-2-yl)-5-bromopyrimidin-2-yl]-[3-(4-ethylpiperazin-1-yl)-propyl]-amine | 460 ($^{79}Br$), 462 ($^{81}Br$) |
| 9 | [4-(Benzo[b]thiophen-2-yl)-5-bromopyrimidin-2-yl]-{3-[4-(2-hydroxyethyl)-piperazin-1-yl]-propyl}-amine | 476 ($^{79}Br$), 478 ($^{81}Br$) |
| 10 | [4-(Benzo[b]thiophen-2-yl)-5-methylpyrimidin-2-yl]-[3-(3,5-dimethylpiperazin-1-yl)-propyl]-amine tri-hydrochloride | 396 |
| 11 | [4-(Benzo[b]thiophen-2-yl)-5-methylpyrimidin-2-yl]-[3-(4-methylpiperazin-1-yl)-propyl]-amine | 382 |
| 12 | [4-(Benzo[b]thiophen-2-yl)-5-methylpyrimidin-2-yl]-[3-(4-ethylpiperazin-1-yl)-propyl]-amine | 396 |
| 13 | [4-(Benzo[b]thiophen-2-yl)-5-methylpyrimidin-2-yl]-[3-(4-n-propylpiperazin-1-yl)-propyl]-amine | 410 |
| 14 | [4-(Benzo[b]thiophen-2-yl)-5-methylpyrimidin-2-yl]-[3-(4-isopropylpiperazin-1-yl)-propyl]-amine | 410 |
| 15 | [4-(Benzo[b]thiophen-2-yl)-pyrimidin-2-yl]-(3-piperazin-1-yl-propyl)-amine tri-hydrochloride | 354 |
| 16 | [4-(Benzo[b]thiophen-2-yl)-5-bromopyrimidin-2-yl]-[3-(piperazin-1-yl)-propyl]-amine tri-hydrochloride | 432 ($^{79}Br$), 434 ($^{81}Br$) |

EXAMPLE 17

[4-(Benzo[b]thiophen-2-yl)-5-methyl-pyrimidin-2-yl]-[3-(piperazin-1-yl)-propyl]-amine 4-(3-Aminopropyl)-piperazine-1-carboxylic acid tert-butyl ester (261 mg, 1.07 mmol) is added to a stirred suspension of 4-(benzo[b]thiophen-2-yl)-2-chloro-5-methyl-pyrimidine (140 mg, 0.537 mmol) and diisopropylethylamine (140 µL, 0.805 mmol) in anhydrous 1,4-dioxane (3.5 mL) at ambient temperature under nitrogen. The resultant mixture is heated in an oil bath at 95° C. for 36 hours. At ambient temperature the mixture is concentrated and chromatographed on silica gel, eluting with 2 M $NH_3/CH_3OH$ in dichloromethane 0-6%, to give 4-{3-[4-(benzo[b]thiophen-2-yl)-5-methyl-pyrimidin-2-yl]-amino-propyl}-piperazine-1-carboxylic acid tert-butyl ester as a white solid (178 mg, 70% yield).

TFA (1 mL) is added to a stirred solution of the above product (168 mg, 0.359 mmol) and triethylsilane (0.172 mL, 1.08 mmol) in anhydrous 1,2-dichloroethane (3 mL) at ambient temperature under nitrogen. The resultant solution is allowed to stir for 8 hours. After concentration, the crude product is suspended in $CH_3OH$ (5 mL)/dichloromethane (3 mL) then treated with 2.5 N lithium hydroxide (LiOH) (0.43 mL) before it is chromatographed on silica gel, eluting with 2 M $NH_3/CH_3OH$ in dichloromethane 5-20%, to give the title compound as a yellowish solid (132 mg, 100% yield). ES+ (m/z) 368 [M+H].

EXAMPLE 18

[4-(Benzo[b]thiophen-2-yl)-5-bromopyrimidin-2-yl]-(2-piperazin-1-yl-ethyl)-amine tri-hydrochloride Using the method of [4-(benzo[b]thiophen-2-yl)-5-methylpyrimidin-2-yl]-[3-(piperazin-1-yl)-propyl]-amine, the free base of the title compound is synthesized from 4-(benzo[b]thiophen-2-yl)-5-bromo-2-chloro-pyrimidine as a white solid. It is readily converted to the tri-hydrochloride salt. ES+(m/z) 418 ($^{79}$Br) and 420 ($^{81}$Br) [M+H].

EXAMPLE 19

2-[2-(3-piperazin-1-ylpropylamino)-pyrimidin-4-yl]-benzo[b]thiophene-4-carboxylic acid cyclopropylamide tri-hydrochloride (A). Preparation of benzo[b]thiophene-4-carboxylic acid methyl ester A mixture of 4-bromobenzo[b]thiophene (20.0 g, 93.8 mmol), Pd(OAc)$_2$ (4.26 g, 19.0 mmol), 1,1'-bis(diphenylphosphino)ferrocene (15.4 g, 27.8 mmol) and triethylamine (72.0 mL, 520 mmol) in MeOH (422 mL)/dimethylsulfoxide (DMSO) (638 mL) is introduced to a 1 i high pressure reaction vessel. The vessel is pressurized with 100 psi carbon monoxide (CO) gas, then the mixture is heated at 80° C. for 24 hours. The dark reaction mixture is concentrated to evaporate off MeOH before it is poured onto 2.4 L ice water with stirring to form a suspension. After filtration, the solid is taken up in dichloromethane and the filtrate is extracted with dichloromethane. The combined dichloromethane solution is concentrated to give a dark gum, it is dissolved in dichloromethane (50 mL) and subjected to chromatography on silica gel, eluting with dichloromethane in hexanes 50-100%, to give the title compound as a tan oil (15.2 g, 84% yield).

(B). Preparation of 2-(2-chloropyrimidin-4-yl)-benzo[b]thiophene-4-carboxylic acid methyl ester Lithium diisopropylamide (5.70 mL, 2 M in THF) is added dropwise to a stirred solution of benzo[b]thiophene-4-carboxylic acid methyl ester (2.00 g, 10.4 mmol) and triisopropyl borate (2.63 mL, 11.4 mmol) in anhydrous THF (20 mL) at −78° C. under nitrogen. Upon the completion of the addition, the mixture is allowed to warm slowly over 1 hour to ambient temperature where it is stirred for another 1 hour. Aqueous $Na_2CO_3$ solution (2 M, 15.6 mL) is added to the mixture, followed by the addition of 1,1'-bis(diphenylphosphino)ferrocene (318 mg, 0.570 mmol), palladium(II) acetate (129 mg, 0.570 mmol) and 2,4-dichloropyrimidine (1.46 g, 10.4 mmol). The reaction mixture is heated to reflux for 16 hours. At ambient temperature THF is evaporated off, the aqueous layer is extracted with CHCl$_3$ (100 mL×2) and the combined layers are concentrated to give a dark solid. The solid is dissolved in dichloromethane and purified by chromatography on silica gel, eluting with dichloromethane in hexanes 50-100%, to give the title compound as a yellowish solid (1.60 g, 51% yield).

(C). Preparation of 4-{3-[4-(4-methoxycarbonyl-benzo[b]thiophen-2-yl)-pyrimidin-2-ylamino]-propyl}-piperazine-1-carboxylic acid tert-butyl ester Using the method of [4-(benzo[b]thiophen-2-yl)-pyrimidin-2-yl]-[3-(4-methylpiperazin-1-yl)-propyl]-amine tri-hydrochloride, the title compound is synthesized from 2-(2-chloro-pyrimidin-4-yl)-benzo[b]thiophene-4-carboxylic acid methyl ester as a solid (74% yield).

(D). Preparation of 4-{3-[4-(4-carboxy-benzo[b]thiophen-2-yl)-pyrimidin-2-ylamino]-propyl}-piperazine-1-carboxylic acid tert-butyl ester di-hydrochloride Aqueous LiOH solution (2.5 N, 2.0 mL) is added to a stirred solution of 4-{3-[4-(4-methoxycarbonyl-benzo[b]thiophen-2-yl)-pyrimidin-2-ylamino]-propyl}-piperazine-1-carboxylic acid tert-butyl ester (700 mg, 1.49 mmol) in THF (7 mL)/MeOH (4 mL), the resultant mixture is stirred at 40° C. for 4 hours. At 40° C., 5 N HCl (2.1 mL) is added in one shot to the reaction mixture. Within 2 minutes the mixture becomes a suspension. After filtration and drying, the title compound is obtained as a yellow solid (950 mg, 99% yield).

(E). Preparation of 2-[2-(3-piperazin-1-yl-propylamino)-pyrimidin-4-yl]-benzo[b]thiophene-4-carboxylic acid, cyclopropylamide tri-hydrochloride Diisopropylethylamine (0.578 mL, 3.33 mmol) and cyclopropylamine (0.231 mL, 3.33 mmol) are added sequentially to a stirred suspension of 4-{3-[4-(4-carboxy-benzo[b]thiophen-2-yl)-pyrimidin-2-ylamino]-propyl}-piperazine-1-carboxylic acid tert-butyl ester dihydrocholric acid (950 mg, 1.66 mmol) in anhydrous DMF (10 mL). Powdered 1H-benzotriazol-1-yloxytris(dimethylamino)phosphonium hexafluorophosphate (884 mg, 2.00 mmol) is added to the mixture, the resultant mixture is allowed to stir at 50° C. for 14 hours. The mixture is concentrated and chromatographed on silica gel, eluting with 2 M $NH_3/CH_3OH$ in dichloromethane 1-5%, to give the N-cyclopropylcarboxamide as a yellowish solid.

The above N-cyclopropylcarboxamide is dissolved in MeOH (40 mL)/dichloromethane (20 mL) and a small stream of anhydrous HCl gas is bubbled through the stirred solution for 3 minutes. The warm solution is capped with a glass stopper and stirred at ambient temperature overnight to form a yellow suspension. After filtration and drying, the title compound is obtained as a yellow solid (480 mg, 53% yield). ES+(m/z) 437 [M+H].

EXAMPLE 20

2-{5-Chloro-2-[3-(4-methylpiperazin-1-yl)-propylamino]-pyrimidin-4-yl}-benzo[b]thiophene-4-carboxylic acid cyclopropylamide tri-hydrochloride (A). Preparation of benzo[b]thiophene-4-carboxylic acid A few crystals of iodine are added to a stirred suspension of magnesium (Mg) (4.79 g, 197 mmol) in anhydrous THF (100 mL) under nitrogen atmosphere, then a solution of 4-bromo-benzo-thiophene (40.0 g, 188 mmol) in anhydrous THF (150 mL) is added dropwise. Initially only 5% of the total amount is added (ca. 1 mL) to start the reaction, after that the rest of the amount is added at the rate to keep the reaction temperature around 50-55° C. This takes around 30 minutes and finally the reaction is heated at 50° C. for 1 hour. When most of the Mg is consumed, the reaction is cooled to 23° C. and $CO_2$ gas (generated from dry ice in a flask) is bubbled into the solution. This reaction is exothermic and the temperature of the solution is kept around 23° C. by means of an ice bath. The bubbling continues for 15-20 minutes until a copious precipitate appears. The reaction is carefully quenched with aqueous 10% HCl at 0° C. Aqueous sodium chloride is added and the mixture is extracted with EtOAc. The organic phase is extracted with aqueous 2 M sodium hydroxide (NaOH) and the aqueous phase is then acidified with aqueous 37% HCl to pH 1 to form a suspension. After filtration and drying, the title compound is obtained as a white solid (24.9 g, 74% yield).

(B). Preparation of (4-carboxybenzo[b]thiophen-2-yl)boronic acid n-Butyllithium (2.5 M, 94 mL) is added dropwise to a stirred solution of diisopropylamine (33.0 mL, 235 mmol) in anhydrous THF (300 mL) at −78° C. under nitrogen atmosphere. After 30 minutes, a solution of benzo[b]thiophene-4-carboxylic acid (20.0 g, 112 mmol) in anhydrous THF (300 mL) is added. Upon the completion of addition, the reaction mixture is allowed to warm up to 0° C. where it is stirred for another 2 hours. The reaction mixture is cooled to −30° C. before it is treated with triisopropyl borate (65.0 mL, 282 mmol). The cooling bath is then removed and the reaction is allowed to reach ambient temperature where it is carefully quenched with concentrated HCl (200 mL). After evaporation of THF a suspension is formed, the solid is collected by filtration, washed twice with water (150 mL×2) and dried to provide the title compound as a white solid (20.0 g, 80% yield).

(C). Preparation of 2-(2,5-dichloropyrimidin-4-yl)-benzo[b]thiophene-4-carboxylic acid An aqueous $Na_2CO_3$ solution (2 M, 500 mL) is added dropwise to a stirred solution of (4-carboxy-benzo[b]thiophen-2-yl)boronic acid (56 g, 0.25 mol) and 2,4,6-trichloro-pyrimidine (42.1 g, 0.230 mol) in ethyleneglycol dimethyl ether (620 mL) at room temperature under nitrogen atmosphere. Upon the completion of addition, $PdCl_2(PPh_3)_2$ (5.31 g, 3% mol) is added in one portion, then the reaction mixture is heated at 100° C. overnight. The mixture is cooled to 10° C., then 37% HCl (150 mL) is added in portions to form a suspension. After filtration and washing with water (300 mL×3) the solid is dried under vacuum. Then the solid is suspended in 1 L of dichloromethane/ethanol (10:1) and stirred overnight. After another round of filtration and drying, the first crop of title compound (28.0 g, 38% yield) is obtained. Mother liquor is concentrated and the residue is suspended in acetone (1 mL) and stirred overnight. After filtration, the solid is re-suspended in 200 mL of dichloromethane/ethanol (ethanol) (3:1) and stirred for 2 hours. Additional 5 g of the title compound is obtained after filtration and drying. Overall yield is 44%.

(D). Preparation of 2-(2,5-dichloropyrimidin-4-yl)-benzo[b]thiophene-4-carboxylic acid, cyclopropylamide Diisopropylethylamine (1.42 mL) is added to a stirred suspension of 2-(2,5-dichloro-pyrimidin-4-yl)-benzo[b]thiophene-4-carboxylic acid (2.55 g, 7.84 mmol) in anhydrous dichloromethane (40 mL) at 0° C. under nitrogen to form a solution, followed by sequentially addition of cyclopropylamine (0.570 mL, 8.23 mmol) and powdered 1H-benzotriazol-1-yloxytris(dimethylamino)phosphonium hexafluorophosphate (3.64 g, 8.23 mmol). The resultant mixture is allowed to stir at 0° C. for 2 hours, then at ambient temperature for 3 hours. Diethyl ether (35 mL) is added in small portions to the mixture, the mixture is stirred for another 20 minutes before filtration. After drying, the crude title compound (2.45 g) is obtained as a tan solid. It is used without further purification.

(E). 2-{5-Chloro-2-[3-(4-methyl-piperazin-1-yl)-propylamino]-pyrimidin-4-yl}-benzo[b]thiophene-4-carboxylic acid, cyclopropylamide tri-hydrochloride 1-(3-Aminopropyl)-4-methylpiperazine (2.27 g, 14.4 mmol) is added to a stirred suspension of crude 2-(2,5-dichloro-pyrimidin-4-yl)-benzo[b]thiophene-4-carboxylic acid, cyclopropylamide (2.10 g, 5.77 mmol) in anhydrous 1,4-dioxane (40 mL) at ambient temperature under nitrogen. The resultant mixture is heated at 95° C. for 6 hours. After concentration, the solid residue is re-suspended in dichloromethane (40 mL)/$CH_3OH$ (16 mL) before it is treated with 2N LiOH (2.89 mL). The mixture is sonicated then subject to separation on silica gel, eluting with 2M $NH_3$/$CH_3OH$ in dichloromethane 0-8%. The fractions containing desired product are collected and slowly concentrated in vacuo until it becomes a 10 mL suspension. Diethyl ether (40 mL) is added in small portions to the suspension under sonication. After filtration and drying, a light yellow solid (1.89 g, 68% yield) is obtained.

The above free base is dissolved in dichloromethane (80 mL)/MeOH (80 mL), then bubbled with a small stream of anhydrous HCl gas for 3 minutes. The yellow solution is slowly concentrated until it becomes a 15 mL suspension. Diethyl ether (70 mL) is added in small portions to the suspension under sonication. After filtration and drying, the title compound is obtained as a yellow solid (2.17 g, 94% yield). ES+(m/z) 485 ($^{35}$Cl) and 487 ($^{37}$Cl) [M+H].

Using the method of 2-{5-chloro-2-[3-(4-methylpiperazin-1-yl)-propylamino]-pyrimidin-4-yl}-benzo[b]thiophene-4-carboxylic acid cyclopropylamide tri-hydrochloride, the following compounds may be prepared and isolated as the free base or the hydrochloride salt:

| Ex. | Compound | MS (ES+) m/z [M + H] |
|---|---|---|
| 21 | 2-{5-Chloro-2-[2-(4-methylpiperazin-1-yl)-ethylamino]-pyrimidin-4-yl}-benzo[b]thiophene-4-carboxylic acid cyclopropylamide tri-hydrochloride | 471 ($^{35}$Cl), 473 ($^{37}$Cl) |
| 22 | 2-{5-Chloro-2-[3-(4-ethylpiperazin-1-yl)-propylamino]-pyrimidin-4-yl}-benzo[b]thiophene-4-carboxylic acid cyclopropylamide tri-hydrochloride | 499 ($^{35}$Cl), 451 ($^{37}$Cl) |
| 23 | 2-{5-Chloro-2-[3-(4-n-propylpiperazin-1-yl)-propylamino]-pyrimidin-4-yl}-benzo[b]thiophene-4-carboxylic acid, cyclopropylamide | 513 ($^{35}$Cl), 515 ($^{37}$Cl) |
| 24 | 2-{5-Chloro-2-[3-(4-isopropylpiperazin-1-yl)-propylamino]-pyrimidin-4-yl}-benzo[b]thiophene-4-carboxylic acid cyclopropylamide | 513 ($^{35}$Cl), 515 ($^{37}$Cl) |
| 25 | 2-{5-Methyl-2-[3-(4-methylpiperazin-1-yl)-propylamino]-pyrimidin-4-yl}-benzo[b]thiophene-4-carboxylic acid cyclopropylamide tri-hydrochloride | 465 |
| 26 | 2-{5-Methyl-2-[3-(4-ethylpiperazin-1-yl)-propylamino]-pyrimidin-4-yl}-benzo[b]thiophene-4-carboxylic acid cyclopropylamide | 479 |
| 27 | 2-{2-[3-(4-Allylpiperazin-1-yl)-propylamino]-5-chloropyrimidin-4-yl}-benzo[b]thiophene-4-carboxylic acid cyclopropylamide tri-hydrochloride | 511 ($^{35}$Cl), 513 ($^{37}$Cl) |
| 28 | 2-{5-Chloro-2-[3-(4-cyclopentylpiperazin-1-yl)-propylamino]-pyrimidin-4-yl}-benzo[b]thiophene-4-carboxylic acid cyclopropylamide tri-hydrochloride | 539 ($^{35}$Cl), 541 ($^{37}$Cl) |
| 29 | 2-(5-Chloro-2-{3-[4-(2-hydroxyethyl)-piperazin-1-yl]-propylamino}-pyrimidin-4-yl)-benzo[b]thiophene-4-carboxylic acid cyclopropylamide tri-hydrochloride | 515 ($^{35}$Cl), 517 ($^{37}$Cl) |
| 30 | 2-{5-Chloro-2-[3-(4-methyl[1,4]diazepan-1-yl)-propylamino]-pyrimidin-4-yl}-benzo[b]thiophene-4-carboxylic acid cyclopropylamide tri-hydrochloride | 499 ($^{35}$Cl), 501 ($^{37}$Cl) |
| 31 | 2-{5-Chloro-2-[4-(4-methylpiperazin-1-yl)-butylamino]-pyrimidin-4-yl}-benzo[b]thiophene-4-carboxylic acid cyclopropylamide tri-hydrochloride | 499 ($^{35}$Cl), 501 ($^{37}$Cl) |
| 32 | 2-(5-Chloro-2-{2-[methyl-(1-methylpiperidin-4-yl)-amino]-ethylamino}-pyrimidin-4-yl)-benzo[b]thiophene-4-carboxylic acid cyclopropylamide tri-hydrochloride | 499 ($^{35}$Cl), 501 ($^{37}$Cl) |
| 33 | 2-(5-Chloro-2-{2-[methyl-((RS)-1-methylpyrrolidin-3-yl)-amino]-ethylamino}-pyrimidin-4-yl)-benzo[b]thiophene-4-carboxylic acid cyclopropylamide | 485 ($^{35}$Cl), 487 ($^{37}$Cl) |
| 34 | 4-{3-[5-Chloro-4-(4-cyclopropylcarbamoyl-benzo[b]thiophen-2-yl)-pyrimidin-2-ylamino]-propyl}-piperazine-1-carboxylic acid amide di-hydrochloride | 514 ($^{35}$Cl), 516 ($^{37}$Cl) |
| 35 | 2-{2-[3-(4-Acetylpiperazin-1-yl)-propylamino]-5-chloropyrimidin-4-yl}-benzo[b]thiophene-4-carboxylic acid cyclopropylamide di-hydrochloride | 513 ($^{35}$Cl), 515 ($^{37}$Cl) |
| 36 | 2-{5-Chloro-2-[3-(4-isobutylpiperazin-1-yl)-propylamino]-pyrimidin-4-yl}-benzo[b]thiophene-4-carboxylic acid cyclopropylamide tri-hydrochloride | 527 ($^{35}$Cl), 529 ($^{37}$Cl) |
| 37 | 2-{5-Chloro-2-[2-(4-dimethylaminopiperidin-1-yl)-ethylamino]-pyrimidin-4-yl}-benzo[b]thiophene-4-carboxylic acid cyclopropylamide tri-hydrochloride | 498 ($^{35}$Cl), 500 ($^{37}$Cl) |
| 38 | 2-{5-Chloro-2-[3-(4-dimethylamino-piperidin-1-yl)-propylamino]-pyrimidin-4-yl}-benzo[b]thiophene-4-carboxylic acid cyclopropylamide tri-hydrochloride | 512 ($^{35}$Cl), 514 ($^{37}$Cl) |
| 39 | 2-{5-Chloro-2-[3-((R)-3-dimethylamino-pyrrolidin-1-yl)-propylamino]-pyrimidin-4-yl}-benzo[b]thiophene-4-carboxylic acid cyclopropylamide tri-hydrochloride | 499 ($^{35}$Cl), 501 ($^{37}$Cl) |
| 40 | 2-{5-Chloro-2-[3-((S)-3-dimethylamino-pyrrolidin-1-yl)-propylamino]-pyrimidin-4-yl}-benzo[b]thiophene-4-carboxylic acid cyclopropylamide tri-hydrochloride | 499 ($^{35}$Cl), 501 ($^{37}$Cl) |

EXAMPLE 41

2-{5-Methyl-2-[3-(4-methylpiperazin-1-yl)-propylamino]-pyrimidin-4-yl}-benzo[b]thiophene-4-carboxylic acid cyclopropylamide di-hydrochloride Hydrochloric acid (1.0 M, 0.306 mL) is added to a stirred suspension of 2-{5-methyl-2-[3-(4-methylpiperazin-1-yl)-propylamino]-pyrimidin-4-yl}-benzo[b]thiophene-4-carboxylic acid cyclopropylamide (71.2 mg, 0.153 mmol) in MeOH (5 mL). The resulting solution is concentrated on the rotorvap at 45° C. to give a solid. After vacuum drying at 45° C. for about 2 hours the title compound is obtained as a solid (80.0 mg; 97% yield). ES+(m/z) 465 [M+H].

EXAMPLE 42

2-{5-Chloro-2-[3-(4-methylpiperazin-1-yl)-propylamino]-pyrimidin-4-yl}-benzo[b]thiophene-4-carboxylic acid cyclopropylamide di-hydrochloride Using the method of 2-{5-methyl-2-[3-(4-methylpiperazin-1-yl)-propylamino]-pyrimidin-4-yl}-benzo[b]thiophene-4-carboxylic acid cyclopropylamide di-hydrochloride, the title compound is synthesized from 2-{5-chloro-2-[3-(4-methylpiperazin-1-yl)-propylamino]-pyrimidin-4-yl}-benzo[b]thiophene-4-carboxylic acid cyclopropylamide and obtained as a solid. ES+(m/z) 485 ($^{35}$Cl) and 487 ($^{37}$Cl) [M+H].

EXAMPLE 43

2-[5-Chloro-2-(3-piperazin-1-ylpropylamino)-pyrimidin-4-yl]-benzo[b]thiophene-4-carboxylic acid cyclopropylamide tri-hydrochloride Using the method of [4-(benzo[b]thiophen-2-yl)-pyrimidin-2-yl]-[3-(4-methylpiperazin-1-yl)-propyl]-amine tri-hydrochloride, the title compound is synthesized from 2-(2,5-dichloropyrimidin-4-yl)-benzo[b]thiophene-4-carboxylic acid cyclopropylamide and 4-(3-aminopropyl)-piperazine-1-carboxylic acid tert-butyl ester and isolated as a yellow solid (43% yield). ES+(m/z) 471 ($^{35}$Cl) and 473 ($^{37}$Cl) [M+H].

EXAMPLE 44

2-[5-Methyl-2-(3-piperazin-1-yl-propylamino)-pyrimidin-4-yl]-benzo[b]thiophene-4-carboxylic acid, cyclopropylamide tri-hydrochloride Using the method of 2-[5-chloro-2-(3-piperazin-1-ylpropylamino)-pyrimidin-4-yl]-benzo[b]thiophene-4-carboxylic acid cyclopropylamide tri-hydrochloride, the title compound is synthesized as a yellow solid. ES+(m/z) 451 [M+H].

Using the method of 2-{5-chloro-2-[3-(4-methylpiperazin-1-yl)-propylamino]-pyrimidin-4-yl}-benzo[b]thiophene-4-carboxylic acid cyclopropylamide tri-hydrochloride, the following compounds are synthesized and isolated as a free base or as the hydrochloride salt:

| Ex. | Compound | MS (ES+) m/z [M + H] |
|---|---|---|
| 45 | 2-{5-Chloro-2-[2-(hexahydro-4-methyl-(1H)-1,4-diazepin-1-yl)-ethylamino]-pyrimidin-4-yl}-benzo[b]thiophene-4-carboxylic acid cyclopropylamide | 485 ($^{35}$Cl), 487 ($^{37}$Cl) |
| 46 | 2-{5-Chloro-2-[3-(3,4,5-trimethylpiperazin-1-yl)-n-propylamino]-pyrimidin-4-yl}-benzo[b]thiophene-4-carboxylic acid cyclopropylamide | 513 ($^{35}$Cl), 515 ($^{37}$Cl) |
| 47 | 2-{5-Chloro-2-[3-(3,5-dimethylpiperazin-1-yl)-n-propylamino]-pyrimidin-4-yl}-benzo[b]thiophene-4-carboxylic acid cyclopropylamide trihydrochloride | 499 ($^{35}$Cl), 501 ($^{37}$Cl) |
| 48 | 2-{5-Chloro-2-[5-(dimethylamino)-n-pentylamino]-pyrimidin-4-yl}-benzo[b]thiophene-4-carboxylic acid cyclopropylamide | 458 ($^{35}$Cl), 460 ($^{37}$Cl) |
| 49 | 2-{5-Chloro-2-[6-(dimethylamino)-n-hexylamino]-pyrimidin-4-yl}-benzo[b]thiophene-4-carboxylic acid cyclopropylamide | 472 ($^{35}$Cl), 474 ($^{37}$Cl) |

EXAMPLE 50

2-{5-Chloro-2-[2-(hexahydropyrrolo[3,4-c]pyrrol-2-yl)-ethylamino]-pyrimidin-4-yl}-benzo[b]thiophene-4-carboxylic acid cyclopropylamide tri-hydrochloride

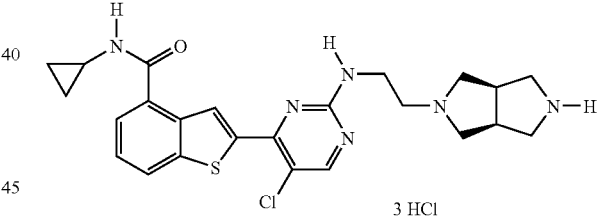

Using the synthetic method of 2-[5-chloro-2-(3-piperazin-1-ylpropylamino)-pyrimidin-4-yl]-benzo[b]thiophene-4-carboxylic acid cyclopropylamide tri-hydrochloride, the title compound is synthesized from 2-(2,5-dichloropyrimidin-4-yl)-benzo[b]thiophene-4-carboxylic acid cyclopropylamide and 5-(2-aminoethyl)-hexahydropyrrolo[3,4-c]pyrrole-2-carboxylic acid tert-butyl ester and isolated as a yellow solid. ES+(m/z) 483 ($^{35}$Cl) and 485 ($^{37}$Cl) [M+H].

EXAMPLE 51

2-{5-Chloro-2-[3-(4-methylpiperazin-1-yl)-propylamino]-pyrimidin-4-yl}-benzo[b]thiophene-4-carboxylic acid amide tri-hydrochloride (A). Preparation of 2-(2,5-dichloro-pyrimidin-4-yl)-benzo[b]thiophene-4-carboxylic acid [bis-(4-methoxy-phenyl)-methyl]-amide Using the method of Preparation D of 2-{5-chloro-2-[3-(4-methylpiperazin-1-yl)-propylamino]-pyrimidin-4-yl}-benzo

[b]thiophene-4-carboxylic acid cyclopropylamide tri-hydrochloride, the title compound is prepared from 2-(2,5-dichloropyrimidin-4-yl)-benzo[b]thiophene-4-carboxylic acid and bis-(4-methoxyphenyl)-methylamine as a tan solid.

(B). Preparation of 2-{5-chloro-2-[3-(4-methyl-piperazin-1-yl)-propylamino]-pyrimidin-4-yl}-benzo[b]thiophene-4-carboxylic acid [bis-(4-methoxy-phenyl)-methyl]-amide Using the method of Preparation E of 2-{5-chloro-2-[3-(4-methylpiperazin-1-yl)-propylamino]-pyrimidin-4-yl}-benzo[b]thiophene-4-carboxylic acid cyclopropylamide tri-hydrochloride, the title compound is prepared from 2-(2,5-dichloropyrimidin-4-yl)-benzo[b]thiophene-4-carboxylic acid [bis-(4-methoxy-phenyl)-methyl]-amide and 1-(3-aminopropyl)-4-methylpiperazine as a white solid (65% yield).

(C). Preparation of 2-{5-chloro-2-[3-(4-methylpiperazin-1-yl)-propylamino]-pyrimidin-4-yl}-benzo[b]thiophene-4-carboxylic acid amide tri-hydrochloride TFA (3 mL) is added to a stirred solution of the above product (634 mg, 0.946 mmol) and triethylsilane (0.755 mL, 4.73 mmol) in anhydrous dichloromethane (10 mL) at ambient temperature under nitrogen. The resultant solution is allowed to stir for 4 hours. After concentration, the crude product is suspended in dichloromethane/MeOH (2:1) then treated with 2.5 N LiOH (1.42 mL) before it is chromatographed on silica gel, eluting with 2 M $NH_3$/MeOH in dichloromethane 0-6%, to give the free base of the title compound as a white solid (420 mg).

The above free base is dissolved in MeOH (35 mL)/dichloromethane (35 mL) and a small stream of anhydrous HCl gas is bubbled through the stirred solution for 2 minutes. The yellow solution is concentrated into a 5 mL suspension then it is treated in small portion with $EtO_2$ (20 mL). After filtration and drying, the title compound is obtained as a yellow solid (510 mg, 97% yield). ES+(m/z) 445 ($^{35}$Cl) and 447 ($^{37}$Cl) [M+H].

EXAMPLE 52

2-{5-Chloro-2-[3-(4-methylpiperazin-1-yl)-propylamino]-pyrimidin-4-yl}-benzo[b]thiophene-4-carboxylic acid, methylamide tri-hydrochloride Using the method of 2-{5-chloro-2-[3-(4-methylpiperazin-1-yl)-propylamino]-pyrimidin-4-yl}-benzo[b]thiophene-4-carboxylic acid cyclopropylamide tri-hydrochloride, the title compound is synthesized and isolated as a yellow solid. ES+(m/z) 459 ($^{35}$Cl) and 461 ($^{37}$Cl) [M+H].

Using the method of Preparation (E) of 2-{5-chloro-2-[3-(4-methylpiperazin-1-yl)-propylamino]-pyrimidin-4-yl}-benzo[b]thiophene-4-carboxylic acid cyclopropylamide tri-hydrochloride, the following compounds are synthesized from 2-(5-bromo-2-chloropyrimidin-4-yl)-benzo[b]thiophene-4-carboxylic acid cyclopropylamide and the corresponding 3-(piperazin-1-yl)-propylamines and isolated as a yellow hydrochloride salt:

| Ex. | Compound | MS (ES+) m/z [M + H] |
|---|---|---|
| 53 | 2-{5-Bromo-2-[3-(4-methylpiperazin-1-yl)-propylamino]-pyrimidin-4-yl}-benzo[b]thiophene-4-carboxylic acid cyclopropylamide tri-hydrochloride | 529 ($^{79}$Br), 531 ($^{81}$Br) |
| 54 | 2-{5-Bromo-2-[3-(4-ethylpiperazin-1-yl)-propylamino]-pyrimidin-4-yl}-benzo[b]thiophene-4-carboxylic acid cyclopropylamide tri-hydrochloride | 543 ($^{79}$Br), 545 ($^{81}$Br) |

Using the methods of 2-{5-chloro-2-[3-(4-methylpiperazin-1-yl)-propylamino]-pyrimidin-4-yl}-benzo[b]thiophene-4-carboxylic acid cyclopropylamide tri-hydrochloride and 2-[5-chloro-2-(3-piperazin-1-ylpropylamino)-pyrimidin-4-yl]-benzo[b]thiophene-4-carboxylic acid cyclopropylamide tri-hydrochloride, the following compounds are synthesized as the di-hydrochloride salt from the 2-(2-chloropyrimidin-4-yl)-benzo[b]thiophene-4-carboxylic acid cyclopropylamides and the corresponding 3-piperidin-4-yl-propylamines:

| Ex. | Compound | MS (ES+) m/z [M + H] |
|---|---|---|
| 55 | 2-{2-[3-(Piperidin-4-yl)-propylamino]-pyrimidin-4-yl}-benzo[b]thiophene-4-carboxylic acid cyclopropylamide di-hydrochloride | 436 |
| 56 | 2-{5-Chloro-2-[3-(piperidin-4-yl)-propylamino]-pyrimidin-4-yl}-benzo[b]thiophene-4-carboxylic acid cyclopropylamide di-hydrochloride | 470 ($^{35}$Cl), 472 ($^{37}$Cl) |
| 57 | 2-{5-Chloro-2-[3-(1-methylpiperidin-4-yl)-propylamino]-pyrimidin-4-yl}-benzo[b]thiophene-4-carboxylic acid cyclopropylamide di-hydrochloride | 484 ($^{35}$Cl), 486 ($^{37}$Cl) |

EXAMPLE 58

2-{5-Chloro-2-[2-(3(S)-dimethylamino-pyrrolidin-1-yl)-ethylamino]-pyrimidin-4-yl}-benzo[b]thiophene-4-carboxylic acid cyclopropylamide Using the method of 2-{5-chloro-2-[3-(4-methylpiperazin-1-yl)-propylamino]-pyrimidin-4-yl}-benzo[b]thiophene-4-carboxylic acid cyclopropylamide tri-hydrochloride, the title compound is synthesized and isolated as a white solid. ES+(m/z) 485 ($^{35}$Cl) and 487 ($^{37}$Cl) [M+H].

EXAMPLE 59

2-{5-Chloro-2-[3-(4-methylpiperazin-1-yl)-propylamino]-pyrimidin-4-yl}-benzo[b]thiophene-6-carboxylic acid cyclopropylamide tri-hydrochloride (A). Preparation of 2-(2,5-dichloro-pyrimidin-4-yl)-benzo[b]thiophene-6-carboxylic acid methyl ester Using the methods of Preparations A and B in 2-[2-(3-piperazin-1-ylpropylamino)-pyrimidin-4-yl]-benzo[b]thiophene-4-carboxylic acid cyclopropylamide tri-hydrochloride, the title compound is synthesized in two steps from 6-bromo-benzo[b]thiophene and 2,4,5-trichloropyrimidine, and it is isolated as a white solid.

(B). Preparation of 2-{5-chloro-2-[3-(4-methyl-piperazin-1-yl)-propylamino]-pyrimidin-4-yl}-benzo[b]thiophene-6-carboxylic acid methyl ester Using the method of Preparation E in 2-{5-chloro-2-[3-(4-methylpiperazin-1-yl)-propylamino]-pyrimidin-4-yl}-benzo[b]thiophene-4-carboxylic acid cyclopropylamide tri-hydrochloride, the title compound is synthesized from 2-(2,5-dichloro-pyrimidin-4-yl)-benzo[b]thiophene-6-carboxylic acid methyl ester and isolated as a white solid.

(C). Preparation of 2-{5-chloro-2-[3-(4-methylpiperazin-1-yl)-propylamino]-pyrimidin-4-yl}-benzo[b]thiophene-6-carboxylic acid tri-hydrochloride.

Aqueous LiOH solution (2.0 M, 2.8 mL) is added to a stirred suspension of 2-{5-chloro-2-[3-(4-methylpiperazin-1-yl)-propylamino]-pyrimidin-4-yl}-benzo[b]thiophene-6-carboxylic acid methyl ester (0.840 g, 1.80 mmol) in MeOH (20 mL)/THF (20 mL)/H$_2$O (6 mL), the resultant mixture is heated at 70° C. for 4.5 hours. While heating the solution, 5.0 N HCl (3.4 mL) is added in one portion then the solution is allowed to cool to ambient temperature to from a suspension. After filtration, the solid is dried in a vacuum oven at 60° C. for 4 hours to give the title compound (0.64 g, 67% yield). ES+(m/z) 446 ($^{35}$Cl) and 448 ($^{37}$Cl) [M+H].

(D). Preparation of 2-{5-chloro-2-[3-(4-methylpiperazin-1-yl)-propylamino]-pyrimidin-4-yl}-benzo[b]thiophene-6-carboxylic acid cyclopropylamide tri-hydrochloride Diisopropylethylamine (0.210 mL, 1.20 mmol), cyclopropylamine (0.090 mL, 1.3 mmol) and (benzotriazol-1-yloxy)tris(dimethylamino)phosphonium hexafluorophosphate (205 mg, 0.460 mmol) are added successively to a stirred suspension of 2-{5-chloro-2-[3-(4-methyl-piperazin-1-yl)-propylamino]-pyrimidin-4-yl}-benzo[b]thiophene-6-carboxylic acid tri-hydrochloride. (195 mg, 0.400 mmol) and LiCl (187 mg, 4.40 mmol) in DMF (4 mL) at ambient temperature under nitrogen, the resultant mixture is heated at 50° C. for 20 hours. After cooling to ambient temperature, the solvent is removed and the residue is subject to chromatography on silica gel, eluting with 2 M NH$_3$/MeOH in dichloromethane 0-8%, to give the free base of the title compound (97 mg). ES+(m/z) 485 ($^{35}$Cl) and 487 ($^{37}$Cl) [M+H]. Using the method of Preparation (E) in 2-{5-chloro-2-[3-(4-methylpiperazin-1-yl)-propylamino]-pyrimidin-4-yl}-benzo[b]thiophene-4-carboxylic acid cyclopropylamide tri-hydrochloride, the free base is converted to the tri-hydrochloride salt as a yellow solid.

Using the method of 2-{5-chloro-2-[3-(4-methylpiperazin-1-yl)-propylamino]-pyrimidin-4-yl}-benzo[b]thiophene-6-carboxylic acid cyclopropylamide tri-hydrochloride, the following compounds are synthesized from 2-{5-chloro-2-[3-(4-methyl-piperazin-1-yl)-propylamino]-pyrimidin-4-yl}-benzo[b]thiophene-6-carboxylic acid tri-hydrochloride and amines and isolated as yellow tri-hydrochloride solids.

| Ex. | Compound | MS (ES+) m/z [M + H] |
|---|---|---|
| 60 | (2-{5-Chloro-2-[3-(4-methylpiperazin-1-yl)-propylamino]-pyrimidin-4-yl}-benzo[b]thiophen-6-yl)-morpholin-4-yl-methanone tri-hydrochloride | 515 ($^{35}$Cl), 517 ($^{37}$Cl) |
| 61 | (2-{5-Chloro-2-[3-(4-methylpiperazin-1-yl)-propylamino]-pyrimidin-4-yl}-benzo[b]thiophen-6-yl)-thiomorpholin-4-ylmethanone tri-hydrochloride | 531 ($^{35}$Cl), 533 ($^{37}$Cl) |

EXAMPLE 62

2-{5-Chloro-2-[3-(4-methyl-piperazin-1-yl)-propylamino]-pyrimidin-4-yl}-benzo[b]thiophene-6-carboxylic acid amide tri-hydrochloride (A). Preparation of 2-{5-chloro-2-[3-(4-methyl-piperazin-1-yl)-propylamino]-pyrimidin-4-yl}-benzo[b]thiophene-6-carboxylic acid [bis-(4-methoxy-phenyl)-methyl]-amide Using the method of Preparation D in 2-{5-chloro-2-[3-(4-methylpiperazin-1-yl)-propylamino]-pyrimidin-4-yl}-benzo[b]thiophene-6-carboxylic acid cyclopropylamide tri-hydrochloride, the title compound is synthesized from 2-{5-chloro-2-[3-(4-methyl-piperazin-1-yl)-propylamino]-pyrimidin-4-yl}-benzo[b]thiophene-6-carboxylic acid tri-hydrochloride. and bis-(4-methoxy-phenyl)-methylamine and isolated as a solid (78% yield).

(B). Preparation of 2-{5-chloro-2-[3-(4-methylpiperazin-1-yl)-propylamino]-pyrimidin-4-yl}-benzo[b]thiophene-6-carboxylic acid amide tri-hydrochloride Using the method of Preparation C in 2-{5-chloro-2-[3-(4-methylpiperazin-1-yl)-propylamino]-pyrimidin-4-yl}-benzo[b]thiophene-4-carboxylic acid amide tri-hydrochloride, the title compound is synthesized from 2-{5-chloro-2-[3-(4-methyl-piperazin-1-yl)-propylamino]-pyrimidin-4-yl}-benzo[b]thiophene-6-carboxylic acid [bis-(4-methoxyphenyl)-methyl]-amide and isolated as a yellow solid. ES+(m/z) 445 ($^{35}$Cl) and 447 ($^{37}$Cl) [M+H].

EXAMPLE 63

2-{5-Methyl-2-[3-(4-methyl-piperazin-1-yl)-propylamino]-pyrimidin-4-yl}-benzo[b]thiophene-6-carboxylic acid amide tri-hydrochloride (A). Preparation of 2-{5-methyl-2-[3-(4-methyl-piperazin-1-yl)-propylamino]-pyrimidin-4-yl}-benzo[b]thiophene-6-carboxylic acid tri-hydrochloride Using the methods of 2-{5-chloro-2-[3-(4-methylpiperazin-1-yl)-propylamino]-pyrimidin-4-yl}-benzo[b]thiophene-6-carboxylic acid cyclopropylamide tri-hydrochloride, the title compound is synthesized from benzo[b]thiophene-6-carboxylic acid methyl ester and isolated as a solid. ES+(m/z) 426 [M+H].

(B). Preparation of 2-{5-methyl-2-[3-(4-methylpiperazin-1-yl)-propylamino]-pyrimidin-4-yl}-benzo[b]thiophene-6-carboxylic acid amide tri-hydrochloride Using the method of Preparation C in 2-{5-chloro-2-[3-(4-methylpiperazin-1-yl)-propylamino]-pyrimidin-4-yl}-benzo[b]thiophene-4-carboxylic acid amide tri-hydrochloride, the title compound is synthesized from 2-{5-methyl-2-[3-(4-methylpiperazin-1-yl)-propylamino]-pyrimidin-4-yl}-benzo[b]thiophene-6-carboxylic acid tri-hydrochloride and isolated as a yellow solid. ES+(m/z) 425 [M+H].

Using the method of 2-{5-methyl-2-[3-(4-methylpiperazin-1-yl)-propylamino]-pyrimidin-4-yl}-benzo[b]thiophene-6-carboxylic acid amide tri-hydrochloride, the following compounds are synthesized from 2-{5-methyl-2-[3-(4-methyl-piperazin-1-yl)-propylamino]-pyrimidin-4-yl}-benzo[b]thiophene-6-carboxylic acid tri-hydrochloride and 2-amino-heterocycles and isolated as yellow tri-hydrochloride solids.

| Ex. | Compound | MS (ES+) m/z [M + H] |
|---|---|---|
| 64 | 2-{5-Methyl-2-[3-(4-methylpiperazin-1-yl)-propylamino]-pyrimidin-4-yl}-benzo[b]thiophene-6-carboxylic acid thiazol-2-ylamide tri-hydrochloride | 508 |
| 65 | 2-{5-Methyl-2-[3-(4-methylpiperazin-1-yl)-propylamino]-pyrimidin-4-yl}-benzo[b]thiophene-6-carboxylic acid (2,3-dihydro-1H-imidazol-2-yl)-amide tri-hydrochloride | 491 |

EXAMPLE 66

{2-[5-Chloro-2-(3-piperazin-1-yl-propylamino)-pyrimidin-4-yl]-benzo[b]thiophen-6-yl}-morpholin-4-yl-methanone tri-hydrochloride (A). Preparation of [2-(2,5-dichloropyrimidin-4-yl)-benzo[b]thiophen-6-yl]-morpholin-4-ylmethanone Using the methods of Preparations A-D in 2-{5-chloro-2-[3-(4-methylpiperazin-1-yl)-propylamino]-pyrimidin-4-yl}-benzo[b]thiophene-4-carboxylic acid cyclopropylamide tri-hydrochloride, the title compound is synthesized from 6-bromo-benzo[b]thiophene and isolated as a solid.

(B). Preparation of {2-[5-chloro-2-(3-piperazin-1-ylpropylamino)-pyrimidin-4-yl]-benzo[b]thiophen-6-yl}-morpholin-4-ylmethanone tri-hydrochloride Using the method of 2-[5-chloro-2-(3-piperazin-1-ylpropylamino)-pyrimidin-4-yl]-benzo[b]thiophene-4-carboxylic acid cyclopropylamide tri-hydrochloride, the title compound is synthesized from [2-(2,5-dichloropyrimidin-4-yl)-benzo[b]thiophen-6-yl]-morpholin-4-yl-methanone and 4-(3-aminopropyl)-piperazine-1-carboxylic acid tert-butyl ester and isolated as a yellow solid. ES+(m/z) 501 ($^{35}$Cl) and 503 ($^{37}$Cl) [M+H].

Using the method of {2-[5-chloro-2-(3-piperazin-1-ylpropylamino)-pyrimidin-4-yl]-benzo[b]thiophen-6-yl}-morpholin-4-ylmethanone tri-hydrochloride, the following compounds are synthesized from 6-bromo-benzo[b]thiophene and isolated as yellow tri-hydrochloride salts.

EXAMPLE 72

N$^1$-[4-(Benzo[b]thiophen-2-yl)-pyrimidin-2-yl]-heptane-1,7-diamine

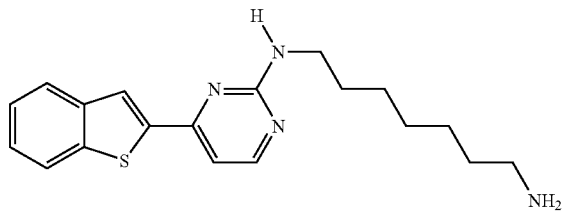

Heptane-1,7-diamine-1-carboxylic acid tert-butyl ester (800 mg, 2.99 mmol) is added to a stirred suspension of 4-benzo[b]thiophen-2-yl-2-chloro-pyrimidine (738 mg, 2.99 mmol) and diisopropylethylamine (0.620 mL, 4.45 mmol) in isopropanol (12 mL) at ambient temperature under nitrogen. The resultant mixture is heated at 110° C. for 20 hours. At ambient temperature, 10% HCl (6 mL) is then added, and the mixture is heated at 110° C. for 15 hours. At ambient temperature the mixture is diluted with dichloromethane (30 mL), washed with 1 N NaOH (10 mL), and dried (MgSO$_4$). After concentration and subsequent chromatographic purification on silica gel, eluting with 2 M NH$_3$/MeOH in dichloromethane 0-20%, the title compound is obtained (385 mg, 95% yield). ESI+(m/z) 341 [M+H]).

EXAMPLE 73

[4(cis)-Aminomethylcyclohexylmethyl]-(4-benzo[b]thiophen-2-ylpyrimidin-2-yl)-amine

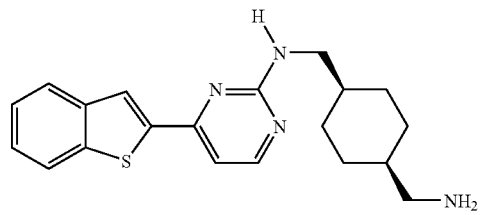

4-Aminomethyl-cyclohexylmethyl-amine (cis/trans-mixture, ca. 2:1) (1.28 g, 9.00 mmol) is added to a stirred suspension of 4-benzo[b]thiophen-2-yl-2-chloro-pyrimidine (986 mg, 4.00 mmol) in isopropanol (13 mL) at ambient tempera-

| Ex. | Compound | MS (ES+) m/z [M + H] |
|---|---|---|
| 67 | {2-[5-Chloro-2-(3-(4-ethylpiperazin-1-yl)-propylamino)-pyrimidin-4-yl]-benzo[b]thiophen-6-yl}-morpholin-4-yl-methanone tri-hydrochloride | 529 ($^{35}$Cl), 531 ($^{37}$Cl) |
| 68 | {2-[5-Methyl-2-(3-piperazin-1-ylpropylamino)-pyrimidin-4-yl]-benzo[b]thiophen-6-yl}-morpholin-4-yl-methanone tri-hydrochloride | 481 |
| 69 | {2-[5-Methyl-2-(3-(4-methylpiperazin-1-yl)-propylamino)-pyrimidin-4-yl]-benzo[b]thiophen-6-yl}-morpholin-4-yl-methanone tri-hydrochloride | 495 |
| 70 | {2-[5-Methyl-2-(3-(4-ethylpiperazin-1-yl)-propylamino)-pyrimidin-4-yl]-benzo[b]thiophen-6-yl}-morpholin-4-yl-methanone tri-hydrochloride | 509 |
| 71 | {2-[5-Chloro-2-(3-(4-ethylpiperazin-1-yl)-propylamino)-pyrimidin-4-yl]-benzo[b]thiophen-6-yl}-thiomorpholin-4-yl-methanone tri-hydrochloride | 545 ($^{35}$Cl), 547 ($^{37}$Cl) | ture under nitrogen. The resultant mixture is heated at 110° C. for 20 hours. At ambient temperature the mixture is diluted with dichloromethane (40 mL), washed with 1N NaOH (13 mL), and dried (MgSO$_4$). After concentration and subsequent chromatographic purification on silica gel, eluting with 2 M NH$_3$/MeOH in dichloromethane 0-20%, the title compound is obtained as a 2:1 cis/trans-mixture (1.24 g, 88% yield). ES+(m/z) 353 [M+H].

A suspension of a 2:1 cis/trans-mixture of (4-aminomethyl-cyclohexylmethyl)-(4-benzo[b]thiophen-2-yl-pyrimidin-2-yl)-amine (1.20 g, 3.40 mmol) in dichloromethane/CH$_3$CN (2:1, 60 mL) is treated with di-tert-butyl dicarbonate (980 mg, 4.49 mmol) in the presence of triethylamine (1.25 mL, 8.97 mmol) at ambient temperature for 48 hours. After concentration and subsequent chromatography on silica gel, eluting with hexanes/ethyl acetate 3:1 to 1:1 to 1:3, a 2:1 cis/trans-mixture of {4-[(4-benzo[b]thiophen-2-yl-pyrimidin-2-ylamino)-methyl]-cyclohexylmethyl}-carbamic acid tert-butyl ester is obtained (1.11 g, 72% yield). ESI+(m/z) 453 [M+H]. 150 mg are purified on Chiralpak AD (250*50 mm) using hexanes-TFA (0.05%)/ethanol 85:15 as eluent (Flow rate: 100 mL/min), to yield 30 mg of cis-4-[(4-benzo[b]thiophen-2-yl-pyrimidin-2-ylamino)-methyl]-cyclohexylmethyl-carbamic acid tert-butyl ester.

A solution of cis-{4-[(4-benzo[b]thiophen-2-yl-pyrimidin-2-ylamino)-methyl]-cyclohexylmethyl}-carbamic acid tert-butyl ester (20 mg, 0.044 mmol) in MeOH (2 mL) is treated at ambient temperature with 10% HCl (2 mL), and the mixture is heated at 110° C. for 15 hours. At ambient temperature the mixture is diluted with dichloromethane (10 mL), washed with 1N NaOH (2 mL), and dried (MgSO$_4$). After concentration in vacuo, the title compound is obtained (15.6 mg, 90% yield). ES+(m/z) 353 [M+H].

EXAMPLE 74

[5-Chloro-4-(7-methoxy-benzo[b]thiophen-2-yl)-pyrimidin-2-yl]-[3-(4-methyl-piperazin-1-yl)-propyl]-amine (A). Preparation of 2,5-dichloro-4-(7-methoxybenzo[b]thiophen-2-yl)-pyrimidine n-Butyl lithium (4.19 mL, 1.6 M in hexane) is added dropwise over 1 hour to a stirred solution of 7-methoxy-benzo[b]thiophene (1.00 g, 6.09 mmol) and triisopropyl borate (1.26 g, 6.70 mmol) in anhydrous THF (10 mL) at −78° C. under nitrogen. The resultant mixture is allowed to stir at −78° C. for 30 minutes, then at −20° C. for another 30 minutes. Aqueous Na$_2$CO$_3$ solution (2 M, 6.09 mL) is added to the mixture, followed by the addition of 1,1'-bis(diphenylphosphino)ferrocene (169 mg, 0.304 mmol), palladium(II) acetate (68.3 mg, 0.304 mmol) and 2,4,5-trichloropyrimidine (1.12 g, 6.09 mmol). Then the reaction mixture is heated to reflux for 18 hours. At ambient temperature CH$_3$OH (10 mL) and CHCl$_3$ (90 mL) are added to the mixture. The organic layer is separated, dried over MgSO$_4$, filtered, and concentrated. After chromatographic purification on silica gel eluting with CH$_3$OH in dichloromethane 0-1%, the title compound is obtained as a yellowish solid (40 mg) and 872 mg starting 7-methoxy-benzo[b]thiophene is recovered.

(B). Preparation of [5-chloro-4-(7-methoxybenzo[b]thiophen-2-yl)-pyrimidin-2-yl]-[3-(4-methyl-piperazin-1-yl)-propyl]-amine Using the method of [4-(benzo[b]thiophen-2-yl)-pyrimidin-2-yl]-[3-(4-methylpiperazin-1-yl)-propyl]-amine tri-hydrochloride, the title compound is prepared from 2,5-dichloro-4-(7-methoxybenzo[b]thiophen-2-yl)-pyrimidine and 1-(3-aminopropyl)-4-methylpiperazine and isolated as a yellowish solid. ES+(m/z) 432($^{35}$Cl) and 434($^{37}$Cl) [M+H].

Using the method of [5-chloro-4-(7-methoxybenzo[b]thiophen-2-yl)-pyrimidin-2-yl]-[3-(4-methylpiperazin-1-yl)-propyl]-amine, the following compounds are synthesized from 7-methoxy-benzo[b]thiophene and isolated as solids.

| Ex. | Compound | MS (ES+) m/z [M + H] |
|---|---|---|
| 75 | [4-(7-Methoxybenzo[b]thiophen-2-yl)-pyrimidin-2-yl]-[3-(4-methyl-piperazin-1-yl)-propyl]-amine | 398 |
| 76 | [5-Methyl-4-(7-methoxybenzo[b]thiophen-2-yl)-pyrimidin-2-yl]-[3-(4-methyl-piperazin-1-yl)-propyl]-amine | 412 |

EXAMPLE 77

[5-Bromo-4-(7-methoxy-benzo[b]thiophen-2-yl)-pyrimidin-2-yl]-[3-(4-methyl-piperazin-1-yl)-propyl]-amine tri-hydrochloride (A). Preparation of 5-bromo-2-chloro-4-(7-methoxybenzo[b]thiophen-2-yl)-pyrimidine.

Using the method of 4-(benzo[b]thiophen-2-yl)-2,5-dichloropyrimidine, the title compound is synthesized from 7-methoxybenzo[b]thiophene and isolated as a solid.

(B). Preparation of [5-bromo-4-(7-methoxy-benzo[b]thiophen-2-yl)-pyrimidin-2-yl]-[3-(4-methyl-piperazin-1-yl)-propyl]-amine tri-hydrochloride Using the method of [4-(benzo[b]thiophen-2-yl)-pyrimidin-2-yl]-[3-(4-methylpiperazin-1-yl)-propyl]-amine tri-hydrochloride, the title compound is prepared from 5-bromo-2-chloro-4-(7-methoxy-benzo[b]thiophen-2-yl)-pyrimidine and 1-(3-aminopropyl)-4-methylpiperazine and isolated as a yellow solid. ES+(m/z) 476 ($^{79}$Br) and 478 ($^{81}$Cl) [M+H].

EXAMPLE 78

2-{2-[3-(4-Methylpiperazin-1-yl)-propylamino]-pyrimidin-4-yl}-benzo[b]thiophen-7-ol

[4-(7-Methoxy-benzo[b]thiophen-2-yl)-pyrimidin-2-yl]-[3-(4-methyl-piperazin-1-yl)-propyl]-amine (150 mg, 0.380 mmol) is dissolved in dry dichloromethane (10 mL) and the solution is cooled to −70° C. To the solution, boron bromide (BBr$_3$) (1.0 M in dichloromethane, 2.64 mL) is added dropwise. The reaction is stirred at −70° C. for 15 minutes, then the cool bath is removed and the reaction is allowed to warm to ambient temperature overnight. After 16 hours, the reaction is again cooled to 70° C. Methanol (5 mL) is added to the reaction mixture then the mixture is allowed to warm to ambient temperature where it is concentrated in vacuo to an orange solid. The crude product is dissolved in THF (minimal) and purified by silica gel chromatography, eluting with MeOH/dichloromethane 0-40%, to yield the title compound as a solid (92.0 mg, 63% yield). ES+(m/z) 384 [M+H].

EXAMPLE 79

2-{5-Methyl-2-[3-(4-methylpiperazin-1-yl)-propylamino]-pyrimidin-4-yl}-benzo[b]thiophen-4-ol (A). Preparation of 4-hydroxybenzo[b]thiophene Into a solution of 6,7-dihydrobenzo[b]thiophen-4(5H)-one (15.3 g, 100 mmol) in ether (600 mL) at −10° C. is added $Br_2$ (16.0 g, 100 mmol) in carbon tetrachloride ($CCl_4$) (100 mL) dropwise over 50 minutes. After an additional 15 minutes at −10° C., the cold bath is removed and the mixture is allowed to warm to ambient temperature. After 1 hour, the mixture is diluted with hexane (300 mL) and washed with water (2×500 mL), aqueous sodium chloride (150 mL) and concentrated under reduced pressure to yield the crude 5-bromo-6,7-dihydrobenzo[b]thiophen-4(5H)-one (22.7 g, 98%) to which is added DMF (~200 mL), $Li_2CO_3$ (14.8 g, 200 mmol) and LiBr (17.4 g, 200 mmol). The mixture is heated for 5 hours at 90° C. and cooled. The crude mixture is poured into water, filtered and the filtrate extracted with EtOAc (600 mL), acidified to pH=1 with concentrated HCl and extracted with EtOAc (600 mL). The combined organic layers are concentrated under reduced pressure to yield a dark oil. The crude material is subjected to chromatography on silica gel, eluting with dichloromethane in hexanes 30-100%, to provide the title compound as an off-white solid (7.62 g, 51% yield).

(B). Preparation of (benzo[b]thiophen-4-yloxy)(tert-butyl)dimethylsilane.

Into a solution of 4-hydroxybenzo[b]thiophene (7.60 g, 50.6 mmol) and tert-butyldimethylsilyl chloride (8.39 g, 55.7 mmol) in dichloromethane (300 mL) is added imidazole (3.79 g, 55.7 mmol) and the mixture is stirred overnight at ambient temperature. The mixture is diluted with hexane (500 mL), filtered and concentrated to a pink oil. The crude material is subjected to chromatography on silica (in hexane) to provide the title compound as a colorless oil (12.9 g, 96% yield).

(C). Preparation of 2-(2-chloro-5-methylpyrimidin-4-yl)benzo[b]thiophen-4-ol

To a −65° C. solution of (benzo[b]thiophen-4-yloxy)(tert-butyl)dimethylsilane (6.25 g, 23.6 mmol) and triisopropylborate (4.89 g, 26.0 mmol) in THF (60 mL) is added lithium diisopropylamide (13.0 mL of a 2 M solution in heptane/THF/ethylbenzene, 26.0 mmol) dropwise over 5 minutes. The mixture is stirred for 2 hours at −70° C., whereupon the cold bath is removed and the mixture is allowed to warm to room temperature. After 2 hours, to the mixture is then added 2,4-dichloro-5-methylpyrimidine (3.85 g, 23.6 mmol), 2M $Na_2CO_3$ (23.6 mL, 47.2 mmol), 1,1'-bis(diphenylphosphino)ferrocene (655 mg, 1.18 mmol) and palladium(II) acetate (265 mg, 1.18 mmol) and the mixture is heated to reflux for 18 hours. Upon cooling to room temperature, the mixture is concentrated under reduced pressure, extracted from water (100 mL) with dichloromethane (3×150 mL) and the organic extracts are concentrated under reduced pressure. The crude material is subjected to chromatography on silica gel, eluting with dichloromethane in hexanes 50-100%, followed by $CHCl_3$ in MeOH 0-100%, to obtain a dark solid. The crude material is extracted from 1 N NaOH (125 mL) with dichloromethane (3×100 mL). The aqueous layer is acidified with 5 N HCl, exhaustively extracted with 10% $CHCl_3$/MeOH followed by 1:1 THF/dichloromethane and concentrated to yield a dark solid. Sonication of the solid in dichloromethane and filtration yielded the title compound as a brown solid (1.10 g, 12% yield).

(D). Preparation of 2-{5-methyl-2-[3-(4-methyl-piperazin-1-yl)-propylamino]-pyrimidin-4-yl}-benzo[b]thiophen-4-ol.

Using the method of [4-(benzo[b]thiophen-2-yl)-pyrimidin-2-yl]-[3-(4-methylpiperazin-1-yl)-propyl]-amine tri-hydrochloride, the title compound is prepared from 2-(2-chloro-5-methylpyrimidin-4-yl)benzo[b]thiophen-4-ol and 1-(3-aminopropyl)-4-methylpiperazine and isolated as a solid. ES+(m/z) 398 [M+H].

EXAMPLE 80

[4-(7-Chloro-benzo[b]thiophen-2-yl)-pyrimidin-2-yl]-[3-(4-methyl-piperazin-1-yl)-propyl]-amine (A). Preparation of 7-chloro-benzo[b]thiophene Into a 2 L round bottomed flask is added 2-chlorobenzenethiol (50.0 g, 346 mmol), potassium carbonate (52.7 g, 381 mmol) and acetone (1 L). 2-Bromo-1,1-diethoxyethane (71.5 g, 363 mmol) is added and the mixture is heated to reflux for 24 hours. The cooled mixture is filtered and concentrated under reduced pressure to yield crude 2-chlorophenyl-(2,2-diethoxyethyl)sulfane as a pale pink oil (101.8 g, quantitative). A 2 L, 3-necked round-bottomed flask, fitted with a mechanical stirrer, condenser and addition funnel is charged with chlorobenzene (1 L) and polyphosphoric acid (200 g) and the mixture is heated to reflux. At reflux the crude (2-chlorophenyl)(2,2-diethoxyethyl)sulfane is added dropwise over 1.5 hours and the mixture is refluxed for a further 24 hours. The cooled organic layer is decanted and concentrated under reduced pressure. The crude material is subjected to chromatography on silica (hexane) to provide the title compound as a brown oil (54.4 g, 93% yield).

(B). Preparation of 2-chloro-4-(7-chlorobenzo[b]thiophen-2-yl)pyrimidine.

A solution of 7-chlorobenzo[b]thiophene (10.0 g, 59.3 mmol) in THF (100 mL) is cooled to −70° C. and triisopropyl borate (12.3 g, 65.2 mmol) is added. n-Butyl lithium (n-BuLi) (40.8 mL, 40.8 mmol, 1.6 M in hexane) is added dropwise via syringe over 40 minutes. After stirring 10 minutes at −75° C., the cold bath is removed and the mixture is allowed to warm to room temperature over 30 minutes. After 3 hours, to the mixture is added 2,4-dichloropyrimidine (8.83 g, 59.3 mmol), 2M $Na_2CO_3$ (60 mL, 120 mmol), 1,1'-bis(diphenylphosphino)ferrocene (1.64 g, 2.96 mmol) and palladium acetate (666 mg, 2.96 mmol) and the mixture is heated to reflux for 18 hours. The cooled mixture is concentrated under reduced pressure, extracted from water with 10% MeOH/$CHCl_3$ (2×200 mL) and concentrated under reduced pressure. The crude material is subjected to chromatography on silica gel eluting with dichloromethane in hexanes 0-100%, to provide the title compound as a light yellow solid (6.95 g, 42% yield).

(C). Preparation of [4-(7-chlorobenzo[b]thiophen-2-yl)-pyrimidin-2-yl]-[3-(4-methylpiperazin-1-yl)-propyl]-amine Using the method of [4-(benzo[b]thiophen-2-yl)-pyrimidin-2-yl]-[3-(4-methylpiperazin-1-yl)-propyl]-amine tri-hydrochloride, the title compound is prepared from 2-chloro-4-(7-chlorobenzo[b]thiophen-2-yl)pyrimidine and 1-(3-aminopropyl)-4-methylpiperazine and isolated as a solid. ES+(m/z) 402 ($^{35}$Cl) and 404 ($^{37}$Cl) [M+H].

Using the methods of Preparations B. and C. in [4-(7-chloro-benzo[b]thiophen-2-yl)-pyrimidin-2-yl]-[3-(4-methylpiperazin-1-yl)-propyl]-amine, the following compounds are synthesized from 7-substituted-benzo[b]thiophene and isolated as solids:

| Ex. | Compound | MS (ES+) m/z [M + H] |
|---|---|---|
| 81 | [4-(7-Methylbenzo[b]thiophen-2-yl)-pyrimidin-2-yl]-[3-(4-methyl-piperazin-1-yl)-propyl]-amine | 382 |
| 82 | [4-(7-Cyanobenzo[b]thiophen-2-yl)-pyrimidin-2-yl]-[3-(4-methyl-piperazin-1-yl)-propyl]-amine | 393 |

EXAMPLE 83

[5-Bromo-4-(7-chlorobenzo[b]thiophen-2-yl)-pyrimidin-2-yl]-[3-(4-methyl-piperazin-1-yl)-propyl]-amine Using the methods of [5-bromo-4-(7-methoxybenzo[b]thiophen-2-yl)-pyrimidin-2-yl]-[3-(4-methylpiperazin-1-yl)-propyl]-amine tri-hydrochloride, the title compound is synthesized from 7-chloro-benzo[b]thiophene and isolated as a solid. ES+(m/z) 480 ($^{35}$Cl, $^{79}$Br), 482 ($^{37}$Cl, $^{79}$Br or $^{35}$Cl, $^{81}$Br) and 484 ($^{37}$Cl, $^{81}$Br) [M+H].

EXAMPLE 84

[4-(6-Bromobenzo[b]thiophen-2-yl)-5-methylpyrimidin-2-yl]-[3-(4-methylpiperazin-1-yl)-propyl]-amine tri-hydrochloride (A). Preparation of 2-chloro-5-methylpyrimidine Into a 3-necked, 500 mL round bottomed flask is added 2,4-dichloro-5-methylpyrimidine (25.0 g, 153 mmol), THF (125 mL) and zinc powder (30.1 g, 460 mmol). The mixture is heated to reflux and acetic acid (HOAc) (9.21 g, 153 mmol) in THF (20 mL) is dropwise added over 1 hour. After 1.5 hours at reflux, additional HOAc (3.93 g, 65.5 mmol) in THF (12.5 mL) is added over 10 minutes, and the mixture is refluxed for an additional 1 hour. The mixture is filtered over celite, rinsed with THF (150 mL) and the organic layers are concentrated under reduced pressure. The crude mixture is partitioned in EtOAc/dichloromethane/1 N NaOH and filtered. The organic layer is concentrated under reduced pressure to yield a peach colored solid. The crude material is subjected to chromatography on silica (in hexane) to provide the title compound as a white solid (13.5 g, 69% yield).

(B). Preparation of 4-(6-bromobenzo[b]thiophen-2-yl)-2-chloro-5-methylpyrimidine A solution of 6-bromobenzo[b]thiophene (5.00 g, 23.5 mmol) in THF (50 mL) is cooled to −70° C. Lithium diisopropylamide (12.9 mL of a 2 M solution in heptane/THF/ethylbenzene, 25.8 mmol) is added dropwise over 5 minutes. After stirring for 40 minutes at −75° C., the mixture is removed from the cold bath and allowed to warm to 0° C. over 15 minutes and then recooled to −35° C. 2-Chloro-5-methylpyrimidine (3.02 g, 23.5 mmol) is added to the mixture as a solid in one portion and the resultant mixture is allowed to stir for 30 minutes at −35° C. Acetic acid (1.55 g, 25.8 mmol) and 2,3-dichloro-5,6-dicyano-1,4-benzoquinone (5.60 g, 24.7 mmol) are added in one portion to the mixture before it is allowed to stir at room temperature for 16 hours. Then the mixture is concentrated under reduced pressure, suspended in warm dichloromethane, eluted through a pad of silica in dichloromethane (1 L) and concentrated under reduced pressure. The crude material is subjected to chromatography on silica gel, eluting with dichloromethane in hexanes 50-100%. The resulting material is sonicated in ether (100 mL) and filtered to provide the title compound as an orange solid (3.08 g, 39% yield).

(C). Preparation of [4-(6-bromo-benzo[b]thiophen-2-yl)-5-methyl-pyrimidin-2-yl]-[3-(4-methyl-piperazin-1-yl)-propyl]-amine tri-hydrochloride Using the method of [4-(benzo[b]thiophen-2-yl)-pyrimidin-2-yl]-[3-(4-methylpiperazin-1-yl)-propyl]-amine tri-hydrochloride, the title compound is prepared from 4-(6-bromobenzo[b]thiophen-2-yl)-2-chloro-5-methylpyrimidine and 1-(3-aminopropyl)-4-methylpiperazine and isolated as a solid. ES+(m/z) 460 ($^{79}$Br) and 462 ($^{81}$Br) [M+H].

EXAMPLE 85

[4-(7-Bromobenzo[b]thiophen-2-yl)-5-methylpyrimidin-2-yl]-[3-(4-methylpiperazin-1-yl)-propyl]-amine Using the method of [4-(6-bromobenzo[b]thiophen-2-yl)-5-methylpyrimidin-2-yl]-[3-(4-methylpiperazin-1-yl)-propyl]-amine tri-hydrochloride, the title compound is prepared from 7-bromobenzo[b]thiophene and isolated as a solid. ES+(m/z) 460 ($^{79}$Br) and 462 ($^{81}$Br) [M+H].

EXAMPLE 86

2-[5-Chloro-2-(2-piperazin-1-ylethylamino)-pyrimidin-4-yl]-benzo[b]thiophene-4-carboxylic acid cyclopropylamide tri-hydrochloride Using the method of [4-(benzo[b]thiophen-2-yl)-pyrimidin-2-yl]-[3-(4-methylpiperazin-1-yl)-propyl]-amine tri-hydrochloride, the title compound is synthesized from 2-(2,5-dichloro-pyrimidin-4-yl)-benzo[b]thiophene-4-carboxylic acid cyclopropylamide and 4-(2-amino-ethyl)-piperazine-1-carboxylic acid tert-butyl ester and isolated as a yellow solid (80% yield). ES+(m/z) 457 ($^{35}$Cl) and 459 ($^{37}$Cl) [M(free base)+H].

EXAMPLE 87

2-[5-Chloro-2-(2-piperidin-4-yl-ethylamino)-pyrimidin-4-yl]-benzo[b]thiophene-4-carboxylic acid cyclopropylamide di-hydrochloride 4-(2-aminoethyl)-piperidine-1-carboxylic acid tert-butyl ester (0.390 g, 1.72 mmol) is added to a stirred suspension of 2-(2,5-dichloro-pyrimidin-4-yl)-benzo[b]thiophene-4-carboxylic acid cyclopropylamide (0.250 g, 0.686 mmol) and diisopropylethylamine (0.300 mL, 1.72 mmol) in anhydrous 1,4-dioxane (4 mL) at room temperature under nitrogen. The resultant mixture is heated at 95° C. for 12 hours then cooled to room temperature and purified (silica gel chromatography, eluting with 2 M NH$_3$/CH$_3$OH in dichloromethane: 0 to 7%) to give 4-{2-[5-chloro-4-(4-cyclopropylcarbamoyl-benzo[b]thiophen-2-yl)-pyrimidin-2-ylamino]-ethyl}-piperidine-1-carboxylic acid tert-butyl ester as a solid.

The above product is dissolved in CH$_3$OH (20 mL)/dichloromethane (20 mL) and a small stream of anhydrous HCl gas is bubbled through the stirred solution for 3 minutes. The warm solution is capped with a glass stopper and stirred at room temperature overnight. After concentration, the title compound is obtained as a yellow solid (0.270 g, 62% yield). ES+(m/z) 456 ($^{35}$Cl) and 458 ($^{37}$Cl) [M(free base)+H].

EXAMPLE 88

2-{5-Chloro-2-[2-(1-methylpiperidin-4-yl)-ethylamino]-pyrimidin-4-yl}-benzo[b]thiophene-4-carboxylic acid cyclopropylamide di-hydrochloride Aqueous formaldehyde (37%, 0.534 mL, 7.21 mmol) is added to a stirred solution of 2-[5-chloro-2-(2-piperidin-4-ylethylamino)-pyrimidin-4-yl]-benzo[b]thiophene-4-carboxylic acid cyclopropylamide (0.600 g, 1.32 mmol) in CH$_3$OH (10 mL) and dichloromethane (10 mL) at room temperature. The resultant mixture is stirred for 30 minutes. The mixture is concentrated and the residue is dissolved in CH$_3$OH (10 mL) and dichloromethane (10 mL). After cooling to 0° C., the solution is treated with sodium cyanoborohydride (0.250 g, 3.95 mmol) and acetic acid (0.030 mL) and stirred for 1 hour. The residue is concentrated and purified (silica gel chromatography, eluting with 2 M NH$_3$/CH$_3$OH in dichloromethane: 0 to 7%), to give the free base as a yellow solid. The free base is dissolved in CH$_3$OH (10 mL) and dichloromethane (10 mL) and the solution is treated with concentrated HCl solution (1 mL) and the yellow solution is concentrated to give the title compound as a yellow solid (0.500 g, 70% yield). ES+(m/z) 470 ($^{35}$Cl) and 472 ($^{37}$Cl) [M(free base)+H].

EXAMPLE 89

2-{5-Chloro-2-[2-(1-ethylpiperidin-4-yl)-ethylamino]-pyrimidin-4-yl}-benzo[b]thiophene-4-carboxylic acid cyclopropylamide di-hydrochloride To a stirred solution of 2-[5-chloro-2-(2-piperidin-4-ylethylamino)-pyrimidin-4-yl]-benzo[b]thiophene-4-carboxylic acid cyclopropylamide (0.250 g, 0.548 mmol) in DMF (10 mL) at room temperature are added iodoethane (0.170 g, 1.10 mmol) and diisopropylethylamine (0.140 g, 1.10 mmol). The resultant mixture is stirred for 2 hours, concentrated, and purified (silica gel chromatography, eluting with 2 M NH$_3$/CH$_3$OH in dichloromethane: 0-7%), to give the free base as a yellow solid. The free base is dissolved in CH$_3$OH (10 mL) and dichloromethane (10 mL) and treated with concentrated HCl solution (0.6 mL). The yellow solution is concentrated to give the title compound as a yellow solid (0.180 g, 58% yield). ES+(m/z) 484 ($^{35}$Cl) and 486 ($^{37}$Cl) [M(free base)+H].

EXAMPLE 90

2-{5-Chloro-2-[3-(1-ethylpiperidin-4-yl)-propylamino]-pyrimidin-4-yl}-benzo[b]thiophene-4-carboxylic acid cyclopropylamide di-hydrochloride Using the method of 2-{5-chloro-2-[2-(1-ethylpiperidin-4-yl)-ethylamino]-pyrimidin-4-yl}-benzo[b]thiophene-4-carboxylic acid cyclopropylamide di-hydrochloride, the title compound may be prepared as the di-hydrochloride acid salt from 2-[5-chloro-2-(3-piperidin-4-yl-propylamino)-pyrimidin-4-yl]-benzo[b]thiophene-4-carboxylic acid cyclopropylamide and iodoethane. ES+(m/z) 498 ($^{35}$Cl) and 500 ($^{37}$Cl) [M(free base)+H].

Using the method of 2-{5-chloro-2-[2-(1-ethylpiperidin-4-yl)-ethylamino]-pyrimidin-4-yl}-benzo[b]thiophene-4-carboxylic acid cyclopropylamide di-hydrochloride, the following compounds are synthesized from 2-[5-chloro-2-(3-piperidin-4-yl-propylamino)-pyrimidin-4-yl]-benzo[b]thiophene-4-carboxylic acid cyclopropylamide and alkyl halides and isolated as the di-hydrochloride salts.

| Ex. | Compound | MS (ES+) m/z [M(free base) + H] |
|---|---|---|
| 91 | 2-(5-Chloro-2-{3-[1-(2-fluoroethyl)-piperidin-4-yl]-propylamino}-pyrimidin-4-yl)-benzo[b]thiophene-4-carboxylic acid cyclopropylamide di-hydrochloride | 516 ($^{35}$Cl), 518 ($^{37}$Cl) |
| 92 | 2-{2-[3-(1-Allylpiperidin-4-yl)-propylamino]-5-chloropyrimidin-4-yl}-benzo[b]thiophene-4-carboxylic acid cyclopropylamide di-hydrochloride | 510 ($^{35}$Cl), 512 ($^{37}$Cl) |
| 93 | 2-(5-Chloro-2-{3-[1-(2-methoxyethyl)-piperidin-4-yl]-propylamino}-pyrimidin-4-yl)-benzo[b]thiophene-4-carboxylic acid cyclopropylamide di-hydrochloride | 528 ($^{35}$Cl), 530 ($^{37}$Cl) |
| 94 | 2-(5-Chloro-2-{3-[1-(3-fluoropropyl)-piperidin-4-yl]-propylamino}-pyrimidin-4-yl)-benzo[b]thiophene-4-carboxylic acid cyclopropylamide di-hydrochloride | 530 ($^{35}$Cl), 532 ($^{37}$Cl) |
| 95 | 2-{5-Chloro-2-[3-(1-cyclopropylmethylpiperidin-4-yl)-propylamino]-pyrimidin-4-yl}-benzo[b]thiophene-4-carboxylic acid cyclopropylamide di-hydrochloride | 524 ($^{35}$Cl), 526 ($^{37}$Cl) |
| 96 | 2-{5-Chloro-2-[3-(1-cyclopentylpiperidin-4-yl)-propylamino]-pyrimidin-4-yl}-benzo[b]thiophene-4-carboxylic acid cyclopropylamide di-hydrochloride | 538 ($^{35}$Cl), 540 ($^{37}$Cl) |

EXAMPLE 97

2-{5-Chloro-2-[3-(1-cyclopropylpiperidin-4-yl)-propylamino]-pyrimidin-4-yl}-benzo[b]thiophene-4-carboxylic acid cyclopropylamide di-hydrochloride Acetic acid (130 mg, 2.12 mmol), 3 Å molecular sieves (300 mg) and [(1-ethoxycyclopropyl)oxy]trimethylsilane (220 mg, 1.27 mmol) are added to a stirred solution of 2-[5-chloro-2-(3-piperidin-4-ylpropylamino)-pyrimidin-4-yl]-benzo[b]thiophene-4-carboxylic acid cyclopropylamide (100 mg, 0.213 mmol) in anhydrous methanol (4 mL), followed by the addition of sodium cyanoborohydride (60 mg, 0.96 mmol). The reaction is heated to reflux overnight. The mixture is cooled to room temperature and filtered. The filtrate is concentrated and purified (silica gel chromatography, eluting with 2 M NH$_3$/CH$_3$OH in dichloromethane: 0-6%), to give the free base as a yellow solid. The free base is dissolved in CH$_3$OH (10 mL) and dichloromethane (10 mL) and a small stream of anhydrous HCl gas is bubbled through the stirred solution for 1 minute. The yellow solution is concentrated to give the title compound as a yellow solid (40 mg, 33% yield). ES+(m/z) 510 ($^{35}$Cl) and 512 ($^{37}$Cl) [M(free base)+H].

EXAMPLE 98

2-{5-Chloro-2-[3-(1-formylpiperidin-4-yl)-propylamino]-pyrimidin-4-yl}-benzo[b]thiophene-4-carboxylic acid cyclopropylamide Cyanomethyl formate (10 mg, 0.11 mmol) is added to a stirred suspension of 2-[5-chloro-2-(3-piperidin-4-yl-propylamino)-pyrimidin-4-yl]-benzo[b]thiophene-4-carboxylic acid cyclopropylamide (50 mg, 0.11 mmol) in DMF (1 mL) and stirred for 18 hours to form a thick suspension. The mixture is diluted with ethyl acetate (1 mL) then filtered to give the title compound as a solid (41 mg). ES+(m/z) 498 ($^{35}$Cl) and 500 ($^{37}$Cl) [M+H].

EXAMPLE 99

4-{3-[5-Chloro-4-(4-cyclopropylcarbamoylbenzo[b]thiophen-2-yl)-pyrimidin-2-ylamino]-propyl}-piperidine-1-carboxylic acid amide Trimethylsilyl isocyanate (26 mg, 0.22 mmol) is added to a stirred suspension of 2-[5-chloro-2-(3-piperidin-4-yl-propylamino)-pyrimidin-4-yl]-benzo[b]thiophene-4-carboxylic acid cyclopropylamide (50 mg, 0.11 mmol) in DMF (1 mL) and stirred for 2 hours. The mixture is diluted with ethyl acetate (1 mL) then filtered to give the title compound as a yellow solid (43 mg). ES+(m/z) 513 ($^{35}$Cl) and 515 ($^{37}$Cl) [M+H].

EXAMPLE 100

2-{5-Chloro-2-[3-(4-formylpiperazin-1-yl)-propylamino]-pyrimidin-4-yl}-benzo[b]thiophene-4-carboxylic acid cyclopropylamide Using the method of 2-{5-chloro-2-[3-(1-formylpiperidin-4-yl)-propylamino]-pyrimidin-4-yl}-benzo[b]thiophene-4-carboxylic acid cyclopropylamide, the title compound is obtained as a solid (88% yield). ES+(m/z) 499 ($^{35}$Cl) and 501 ($^{37}$Cl) [M+H].

EXAMPLE 101

4-{3-[5-Chloro-4-(4-cyclopropylcarbamoyl-benzo[b]thiophen-2-yl)-pyrimidin-2-ylamino]-propyl}-piperazine-1-carboxylic acid methylamide di-hydrochloride Methyl isocyanate (10 mg, 0.22 mmol) is added to a stirred solution of 2-[5-chloro-2-(3-piperazin-1-ylpropylamino)-pyrimidin-4-yl]-benzo[b]thiophene-4-carboxylic acid cyclopropylamide (0.10 g, 0.21 mmol) in DMF (1 mL). The mixture is stirred for 2 hours and the crude product is chromatographed on silica gel, eluting with 2 M NH$_3$/CH$_3$OH in dichloromethane: 0-6%, to give the free base as a solid. The free base is dissolved in CH$_3$OH (10 mL) and dichloromethane (10 mL) and a small stream of anhydrous HCl gas is bubbled through the stirred solution for 1 minute. The yellow solution is concentrated to give the title compound as a yellow solid (80 mg, 62% yield). ES+(m/z) 528 ($^{35}$Cl) and 530 ($^{37}$Cl) [M(free base)+H].

EXAMPLE 102

Racemic 2-[5-Chloro-2-(3-piperidin-3-yl-propylamino)-pyrimidin-4-yl]-benzo[b]thiophene-4-carboxylic acid cyclopropylamide di-hydrochloride Using the method of 2-[5-chloro-2-(2-piperidin-4-yl-ethylamino)-pyrimidin-4-yl]-benzo[b]thiophene-4-carboxylic acid cyclopropylamide di-hydrochloride, the title compound is synthesized as a di-hydrochloride salt from 2-(2,5-dichloropyrimidin-4-yl)-benzo[b]thiophene-4-carboxylic acid cyclopropylamide and racemic 3-(3-aminopropyl)-piperidine-1-carboxylic acid tert-butyl ester. ES+(m/z) 470 ($^{35}$Cl) and 472 ($^{37}$Cl) [M(free base)+H].

EXAMPLE 103

Racemic 2-{5-Chloro-2-[3-(1-methylpiperidin-3-yl)-propylamino]-pyrimidin-4-yl}-benzo[b]thiophene-4-carboxylic acid cyclopropylamide di-hydrochloride Using the method of 2-{5-chloro-2-[2-(1-methylpiperidin-4-yl)-ethylamino]-pyrimidin-4-yl}-benzo[b]thiophene-4-carboxylic acid cyclopropylamide di-hydrochloride, the title compound is synthesized as the di-hydrochloride salt from racemic 2-{5-chloro-2-[3-(1-methylpiperidin-3-yl)-propylamino]-pyrimidin-4-yl}-benzo[b]thiophene-4-carboxylic acid cyclopropylamide. ES+(m/z) 484 ($^{35}$Cl) and 486 ($^{37}$Cl) [M(free base)+H].

EXAMPLE 104

2-{5-Chloro-2-[3-(2,6-cis-dimethyl-piperazin-1-yl)-propylamino]-pyrimidin-4-yl}-benzo[b]thiophene-4-carboxylic acid cyclopropylamide (Diisopropylethylamine (0.40 g, 3.1 mmol) and 3-(4-benzhydryl-2,6-cis-dimethylpiperazin-1-yl)-propylamine (1.02 g, 3.08 mmol) are added to a stirred suspension of 2-(2,5-dichloropyrimidin-4-yl)-benzo[b]thiophene-4-carboxylic acid cyclopropylamide (0.450 g, 1.23 mmol) in anhydrous 1,4-dioxane (10 mL). The resultant mixture is heated at 95° C. for 12 hours. After concentration and subsequent chromatography on silica gel, eluting with 2 M NH$_3$/CH$_3$OH in dichloromethane: 0-6%, the desired intermediate is obtained as a solid which is then treated with TFA (4 mL) in dichloromethane (4 mL) for 20 hours. After concentration and subsequent chromatography on silica gel, eluting with 2 M NH$_3$/CH$_3$OH in dichloromethane: 0-16%, the title compound is obtained as a yellow solid. ES+(m/z) 499 ($^{35}$Cl) and 501 ($^{37}$Cl) [M+H].

EXAMPLE 105

2-{5-Chloro-2-[3-(2,4,6-trimethylpiperazin-1-yl)-propylamino]-pyrimidin-4-yl}-benzo[b]thiophene-4-carboxylic acid cyclopropylamide tri-hydrochloride Using the method of 2-{5-chloro-2-[2-(1-methylpiperidin-4-yl)-ethylamino]-pyrimidin-4-yl}-benzo[b]thiophene-4-carboxylic acid cyclopropylamide di-hydrochloride, the title compound is synthesized from 2-{5-chloro-2-[3-(2,6-cis-dimethylpiperazin-1-yl)-propylamino]-pyrimidin-4-yl}-benzo[b]thiophene-4-carboxylic acid cyclopropylamide as a yellow solid. ES+(m/z) 513 ($^{35}$Cl) and 515 ($^{37}$Cl) [M(free base)+H].

EXAMPLE 106

2-{5-Bromo-2-[3-(4-methyl-[1,4]diazepan-1-yl)-propylamino]-pyrimidin-4-yl}-benzo[b]thiophene-4-carboxylic acid cyclopropylamide tri-hydrochloride Using the method of 2-{5-chloro-2-[3-(4-methylpiperazin-1-yl)-propylamino]-pyrimidin-4-yl}-benzo[b]thiophene-4-carboxylic acid cyclopropylamide tri-hydrochloride, the title compound is synthesized as a yellow solid from 2-(5-bromo-2-chloropyrimidin-4-yl)-benzo[b]thiophene-4-carboxylic acid cyclopropylamide and 3-(4-methyl-[1,4]diazepan-1-yl)-propylamine. ES+(m/z) 543 ($^{79}$Br) and 545 ($^{81}$Br) [M(free base)+H].

Using the method of 2-{5-chloro-2-[3-(4-methylpiperazin-1-yl)-propylamino]-pyrimidin-4-yl}-benzo[b]thiophene-4-carboxylic acid, cyclopropylamide tri-hydrochloride, the following compounds are synthesized from 2-(5-bromo-2-chloropyrimidin-4-yl)-benzo[b]thiophene-4-carboxylic acid cyclopropylamide and the corresponding amines and isolated as the hydrochloride salt.

| Ex. | Compound | MS (ES+) m/z [M(free base) + H] |
|---|---|---|
| 107 | 2-{5-Bromo-2-[2-(4-methylpiperazin-1-yl)-ethylamino]-pyrimidin-4-yl}-benzo[b]thiophene-4-carboxylic acid cyclopropylamide tri-hydrochloride | 515 ($^{79}$Br), 517 ($^{81}$Br) |
| 108 | 2-{5-Bromo-2-[2-(4-ethylpiperazin-1-yl)-ethylamino]-pyrimidin-4-yl}-benzo[b]thiophene-4-carboxylic acid cyclopropylamide tri-hydrochloride | 529 ($^{79}$Br), 531 ($^{81}$Br) |
| 109 | 2-{5-Bromo-2-[3-((3R,5S)-3,5-dimethylpiperazin-1-yl)-propylamino]-pyrimidin-4-yl}-benzo[b]thiophene-4-carboxylic acid cyclopropylamide tri-hydrochloride | 543 ($^{79}$Br), 545 ($^{81}$Br) |
| 110 | 2-{5-Bromo-2-[3-((3R,5S)-3,4,5-trimethylpiperazin-1-yl)-propylamino]-pyrimidin-4-yl}-benzo[b]thiophene-4-carboxylic acid cyclopropylamide tri-hydrochloride | 557 ($^{79}$Br), 559 ($^{81}$Br) |
| 111 | 2-{5-Bromo-2-[3-(4-isopropylpiperazin-1-yl)-propylamino]-pyrimidin-4-yl}-benzo[b]thiophene-4-carboxylic acid cyclopropylamide tri-hydrochloride | 557 ($^{79}$Br), 559 ($^{81}$Br) |

EXAMPLE 112

2-[5-Bromo-2-(2-piperazin-1-ylethylamino)-pyrimidin-4-yl]-benzo[b]thiophene-4-carboxylic acid cyclopropylamide tri-hydrochloride Using the synthetic method of 2-[5-chloro-2-(2-piperidin-4-ylethylamino)-pyrimidin-4-yl]-benzo[b]thiophene-4-carboxylic acid cyclopropylamide di-hydrochloride, the title compound is synthesized from 2-(5-bromo-2-chloropyrimidin-4-yl)-benzo[b]thiophene-4-carboxylic acid cyclopropylamide and 4-(2-aminoethyl)-piperazine-1-carboxylic acid tert-butyl ester and isolated as a yellow solid (67% yield). ES+(m/z) 501 ($^{79}$Br) and 503 ($^{81}$Br) [M(free base)+H].

EXAMPLE 113

2-[5-Bromo-2-(3-piperazin-1-yl-propylamino)-pyrimidin-4-yl]-benzo[b]thiophene-4-carboxylic acid cyclopropylamide tri-hydrochloride Using the synthetic method of 2-[5-chloro-2-(2-piperidin-4-yl-ethylamino)-pyrimidin-4-yl]-benzo[b]thiophene-4-carboxylic acid cyclopropylamide di-hydrochloride, the title compound is synthesized from 2-(5-bromo-2-chloropyrimidin-4-yl)-benzo[b]thiophene-4-carboxylic acid cyclopropylamide and 4-(3-aminopropyl)-piperazine-1-carboxylic acid tert-butyl ester and isolated as a yellow solid (59% yield). ES+(m/z) 515 ($^{79}$Br) and 517 ($^{81}$Br) [M(free base)+H].

EXAMPLE 114

2-[5-Bromo-2-(2-piperidin-4-ylethylamino)-pyrimidin-4-yl]-benzo[b]thiophene-4-carboxylic acid cyclopropylamide 4-(2-Aminoethyl)-piperidine-1-carboxylic acid tert-butyl ester (1.41 g, 6.18 mmol) is added to a stirred suspension of 2-(5-bromo-2-chloropyrimidin-4-yl)-benzo[b]thiophene-4-carboxylic acid cyclopropylamide (0.75 g, 2.1 mmol) and diisopropylethylamine (0.80 g, 6.2 mmol) in anhydrous 1,4-dioxane (15 mL) at room temperature under nitrogen. The resultant mixture is heated in an oil bath at 90° C. for 12 hours. At room temperature the mixture is concentrated and chromatographed on silica gel, eluting with 2 M NH$_3$/CH$_3$OH in dichloromethane: 1-10%, to give 4-{2-[5-bromo-4-(4-cyclopropylcarbamoyl-benzo[b]thiophen-2-yl)-pyrimidin-2-ylamino]-ethyl}-piperidine-1-carboxylic acid tert-butyl ester as a solid.

Triethylsilane (0.7 mL) and TFA (4 mL) are added successively to a stirred suspension of the above product in dichloromethane (10 mL). The resultant yellow solution is stirred for 2 hours. After concentration to dryness, the crude product is dissolved in MeOH (20 mL) and dichloromethane (10 mL) and the solution is treated in portions with 2 N LiOH (7.4 mL) to form a suspension. Organic solvents are evaporated under vacuum at room temperature. The aqueous suspension is filtered, washed with water and dried to give the title compound as a yellow solid (0.869 g, 83% yield). ES+(m/z) 500 ($^{79}$Br) and 502 ($^{81}$Br) [M+H].

Using the method of 2-{5-chloro-2-[2-(1-methylpiperidin-4-yl)-ethylamino]-pyrimidin-4-yl}-benzo[b]thiophene-4-carboxylic acid cyclopropylamide di-hydrochloride, the following compounds are synthesized from 2-[5-bromo-2-(2-piperidin-4-yl-ethylamino)-pyrimidin-4-yl]-benzo[b]thiophene-4-carboxylic acid cyclopropylamide and the corresponding amines and isolated as the free base or hydrochloride salt.

| Ex. | Compound | MS (ES+) m/z [M(free base) + H] |
|---|---|---|
| 115 | 2-{5-Bromo-2-[2-(1-methylpiperidin-4-yl)-ethylamino]-pyrimidin-4-yl}-benzo[b]thiophene-4-carboxylic acid cyclopropylamide di-hydrochloride | 514 ($^{79}$Br), 516 ($^{81}$Br) |
| 116 | 2-{5-Bromo-2-[2-(1-ethylpiperidin-4-yl)-ethylamino]-pyrimidin-4-yl}-benzo[b]thiophene-4-carboxylic acid cyclopropylamide di-hydrochloride | 528 ($^{79}$Br), 530 ($^{81}$Br) |
| 117 | 2-(5-Bromo-2-{2-[1-(2-fluoroethyl)-piperidin-4-yl]-ethylamino}-pyrimidin-4-yl)-benzo[b]thiophene-4-carboxylic acid cyclopropylamide di-hydrochloride | 546 ($^{79}$Br), 548 ($^{81}$Br) |
| 118 | 2-[5-Bromo-2-(3-piperidin-4-yl-propylamino)-pyrimidin-4-yl]-benzo[b]thiophene-4-carboxylic acid cyclopropylamide | 514 ($^{79}$Br), 516 ($^{81}$Br) |
| 119 | 2-{5-Bromo-2-[3-(1-methylpiperidin-4-yl)-propylamino]-pyrimidin-4-yl}-benzo[b]thiophene-4-carboxylic acid cyclopropylamide di-hydrochloride | 528 ($^{79}$Br), 530 ($^{81}$Br) |
| 120 | 2-{5-Bromo-2-[3-(1-ethylpiperidin-4-yl)-propylamino]-pyrimidin-4-yl}-benzo[b]thiophene-4-carboxylic acid cyclopropylamide di-hydrochloride | 542 ($^{79}$Br), 544 ($^{81}$Br) |

EXAMPLE 121

2-[5-Fluoro-2-(3-piperazin-1-yl-propylamino)-pyrimidin-4-yl]-benzo[b]thiophene-4-carboxylic acid cyclopropylamide tri-hydrochloride (4-(3-Aminopropyl)-piperazine-1-carboxylic acid tert-butyl ester (0.542 g, 2.23 mmol) is added to a stirred suspension of 2-(2-chloro-5-fluoropyrimidin-4-yl)-benzo[b]thiophene-4-carboxylic acid cyclopropylamide (0.388 g, 1.12 mmol) and diisopropylethylamine (0.585 mL, 3.36 mmol) in anhydrous 1,4-dioxane (10 mL) at room temperature under nitrogen. The resultant mixture is heated in an oil bath at 95° C. for 24 hours. At room temperature, the mixture is concentrated and chromatographed on silica gel, eluting with 2 M NH$_3$/CH$_3$OH in dichloromethane: 0-7%, to give 4-{3-[4-(4-cyclopropylcarbamoyl-benzo[b]thiophen-2-yl)-5-fluoropyrimidin-2-ylamino]-propyl}-piperazine-1-carboxylic acid tert-butyl ester as a yellow solid (452 mg). The product is dissolved in CH$_3$OH (80 mL) and dichloromethane (20 mL) and a small stream of anhydrous HCl gas is bubbled through the stirred solution for 3 minutes. The warm solution is capped with a glass stopper and stirred at room temperature overnight. After concentration, the title compound is obtained as a yellow solid (441 mg). ES+(m/z) 455 [M(free base)+H].

EXAMPLE 122

2-[5-Fluoro-2-(3-piperidin-4-ylpropylamino)-pyrimidin-4-yl]-benzo[b]thiophene-4-carboxylic acid cyclopropylamide 4-(3-Aminopropyl)-piperidine-1-carboxylic acid tert-butyl ester (0.557 g, 2.30 mmol) is added to a stirred suspension of 2-(2-chloro-5-fluoropyrimidin-4-yl)-benzo[b]thiophene-4-carboxylic acid cyclopropylamide (0.400 g, 1.15 mmol) and diisopropylethylamine (0.60 mL, 3.5 mmol) in anhydrous 1,4-dioxane (8 mL) at room temperature under nitrogen. The resultant mixture is heated in an oil bath at 95° C. for 34 hours. At room temperature the mixture is concentrated and chromatographed on silica gel, eluting with CH$_3$OH in dichloromethane: 0-2%, to give 4-{3-[4-(4-cyclopropylcarbamoyl-benzo[b]thiophen-2-yl)-5-fluoropyrimidin-2-ylamino]-propyl}-piperidine-1-carboxylic acid tert-butyl ester (0.512 g) as a solid.

Triethylsilane (0.7 mL) and TFA (4 mL) are added successively to a stirred suspension of the above product in dichloromethane (20 mL). The resultant yellow solution is stirred for 3 hours. After concentration and subsequent silica gel chromatography, eluting with 2N NH$_3$/CH$_3$OH in dichloromethane: 0-24%, the fractions containing the product are collected and concentrated to give a solid. The solid is dissolved in MeOH (40 mL) and the solution is treated in portions with 2 N LiOH (16 mL) to form a suspension. Methanol is evaporated off under vacuum at room temperature. Water (40 mL) is added to the thick suspension before it is filtered and dried to give the title compound as a yellow solid (0.400 g, 76% yield). ES+(m/z) 454 [M+H].

EXAMPLE 123

2-{5-Fluoro-2-[3-(1-methylpiperidin-4-yl)-propylamino]-pyrimidin-4-yl}-benzo[b]thiophene-4-carboxylic acid cyclopropylamide di-hydrochloride Aqueous formaldehyde (37%, 0.310 mL, 4.17 mmol) is added to a stirred solution of 2-[5-fluoro-2-(3-piperidin-4-ylpropylamino)-pyrimidin-4-yl]-benzo[b]thiophene-4-carboxylic acid cyclopropylamide (0.315 g, 0.694 mmol) in CH$_3$OH (20 mL) and dichloromethane (20 mL) at room temperature to form a suspension. The resultant mixture is allowed to stir for 3 hours. The mixture is diluted with CH$_3$OH (10 mL) and dichloromethane (10 mL), cooled to 0° C. and treated with powdered sodium borohydride (0.131 g, 3.47 mmol). The mixture is stirred for another 1 hour and then allowed to warm up slowly to room temperature where it is stirred for another 3 hours. After concentration and subsequent chromatography on silica gel, eluting with 2 M NH$_3$/CH$_3$OH in dichloromethane: 0-8%, the free base (0.300 g) is obtained as a yellow solid. The free base is dissolved in CH$_3$OH (20 mL) and dichloromethane (20 mL) and the solution is treated with concentrated HCl solution (0.5 mL) and the yellow solution is concentrated to give the title compound as a yellow solid (0.350 g, yield 92%). ES+(m/z) 468 [M(free base)+H].

EXAMPLE 124

2-{2-[3-(3-R-Isopropylpyrrolidin-1-yl)-propylamino]-5-methyl-pyrimidin-4-yl}-benzo[b]thiophene-4-carboxylic acid cyclopropylamide tri-hydrochloride

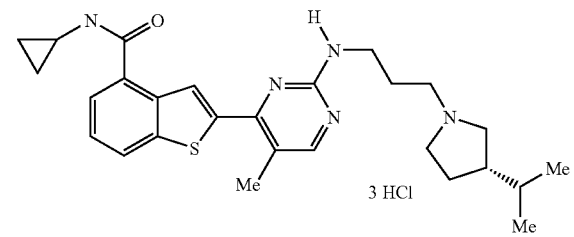

Using the method of 2-{5-chloro-2-[3-(4-methylpiperazin-1-yl)-propylamino]-pyrimidin-4-yl}-benzo[b]thiophene-4-carboxylic acid cyclopropylamide tri-hydrochloride, the title compound is synthesized from 2-(2-chloro-5-methylpyrimidin-4-yl)-benzo[b]thiophene-4-carboxylic acid cyclopropylamide and R-[1-(3-aminopropyl)-pyrrolidin-3-yl]-dimethyl-amine as a yellow solid. ES+(m/z) 479 [M(free base)+H].

EXAMPLE 125

2-{2-[3-(2,6-Dimethylpiperazin-1-yl)-propylamino]-5-methylpyrimidin-4-yl}-benzo[b]thiophene-4-carboxylic acid cyclopropylamide Using the method of 2-{5-chloro-2-[3-(2,6-cis-dimethylpiperazin-1-yl)-propylamino]-pyrimidin-4-yl}-benzo[b]thiophene-4-carboxylic acid cyclopropylamide, the title compound is synthesized from 2-(2-chloro-5-methylpyrimidin-4-yl)-benzo[b]thiophene-4-carboxylic acid cyclopropylamide and 3-(4-benzhydryl-2,6-cis-dimethylpiperazin-1-yl)-propylamine as a yellow solid. ES+(m/z) 479 [M+H].

EXAMPLE 126

2-[5-Methyl-2-(2-piperidin-4-ylethylamino)-pyrimidin-4-yl]-benzo[b]thiophene-4-carboxylic acid cyclopropylamide 4-(2-Aminoethyl)-piperidine-1-carboxylic acid tert-butyl ester (1.22 g, 5.35 mmol) is added to a stirred suspension of 2-(2-chloro-5-methylpyrimidin-4-yl)-benzo[b]thiophene-4-carboxylic acid cyclopropylamide (0.736 g, 2.14 mmol) and diisopropylethylamine (1.12 mL, 6.42 mmol) in anhydrous 1,4-dioxane (8 mL) at room temperature under nitrogen. The resultant mixture is heated in an oil bath at 97° C. for 48 hours. At room temperature the mixture is concentrated and chromatographed on silica gel, eluting with CH$_3$OH in dichloromethane: 0-4%, to give 4-{2-[4-(4-cyclopropylcarbamoyl-benzo[b]thiophen-2-yl)-5-methyl-pyrimidin-2-ylamino]-ethyl}-piperidine-1-carboxylic acid tert-butyl ester as a solid.

The above product is suspended in anhydrous dichloromethane (20 mL) with stirring, treated successively with triethylsilane (1.71 mL, 10.7 mmol) and trifluoacetic acid (5 mL). The resultant yellow solution is allowed to stir for 1 hour. After concentration and chromatographic purification on silica gel, eluting with 6% CH$_3$OH in dichloromethane, then 2M NH$_3$/CH$_3$OH in dichloromethane: 4-12%, the fractions containing product are collected and concentrated to give a yellow solid. The solid is suspended in CH$_3$OH (30 mL) with stirring and the light suspension is treated portionwise with 0.5 N LiOH (30 mL) to form a thick suspension. The suspension is slowly rotated on a rotary evaporator at 45° C. for 20 minutes under atmospheric pressure, then the methanol is evaporated off in vacuo. At room temperature the suspension is filtered and the yellow solid is washed with water before it is dried under vacuum at 80° C. to give the title compound as a yellow solid (712 mg, 76% yield). ES+(m/z) 436 [M+H].

EXAMPLE 127

2-{5-Methyl-2-[2-(1-methylpiperidin-4-yl)-ethylamino]-pyrimidin-4-yl}-benzo[b]thiophene-4-carboxylic acid cyclopropylamide di-hydrochloride Aqueous formaldehyde (37.4% or 13.5 M, 0.60 mL, 8.04 mmol) is added to a stirred solution of 2-[5-methyl-2-(2-piperidin-4-yl-ethylamino)-pyrimidin-4-yl]-benzo[b]thiophene-4-carboxylic acid cyclopropylamide (700 mg, 1.61 mmol) in CH$_3$OH (15 mL) and dichloromethane (15 mL) at room temperature to form a light suspension and the mixture is allowed to stir for 90 minutes. The mixture is cooled to −5° C. before it is treated with powdered sodium borohydride (304 mg, 8.04 mmol). The mixture is stirred at −5 to 0° C. for 60 minutes, then allowed to slowly warm up to room temperature to form a clear solution. After concentration, the crude product is subject to silica gel chromatography, eluting with 2M NH$_3$/CH$_3$OH in dichloromethane: 4-15%, to give the free base as a yellowish solid. The free base is dissolved in CH$_3$OH (20 mL) and dichloromethane (20 mL) and treated with 12N HCl (1.3 mL) to form a yellow solution. After concentrated and vacuum drying at 80° C., the title compound is obtained as a yellow solid (745 mg, 89% yield). ES+(m/z) 450 [M(free base)+H].

EXAMPLE 128

2-[5-Methyl-2-(3-piperidin-4-ylpropylamino)-pyrimidin-4-yl]-benzo[b]thiophene-4-carboxylic acid cyclopropylamide Using the method of 2-[5-methyl-2-(2-piperidin-4-ylethylamino)-pyrimidin-4-yl]-benzo[b]thiophene-4-carboxylic acid cyclopropylamide, the title compound is synthesized from 2-(2-chloro-5-methylpyrimidin-4-yl)-benzo[b]thiophene-4-carboxylic acid cyclopropylamide and 4-(3-aminopropyl)-piperidine-1-carboxylic acid tert-butyl ester and isolated as a yellow solid. ES+(m/z) 450 [M+H].

EXAMPLE 129

2-{5-Methyl-2-[3-(1-methylpiperidin-4-yl)-propylamino]-pyrimidin-4-yl}-benzo[b]thiophene-4-carboxylic acid cyclopropylamide di-hydrochloride Using the method of 2-{5-methyl-2-[2-(1-methylpiperidin-4-yl)-ethylamino]-pyrimidin-4-yl}-benzo[b]thiophene-4-carboxylic acid cyclopropylamide di-hydrochloride, the title compound is synthesized from 2-[5-methyl-2-(3-piperidin-4-yl-propylamino)-pyrimidin-4-yl]-benzo[b]thiophene-4-carboxylic acid cyclopropylamide and isolated as a yellow solid. ES+(m/z) 464 [M(free base)+H].

EXAMPLE 130

2-(2-{3-[1-(2-Fluoroethyl)-piperidin-4-yl]-propylamino}-5-methyl-pyrimidin-4-yl)-benzo[b]thiophene-4-carboxylic acid cyclopropylamide di-hydrochloride Using the method of 2-{5-chloro-2-[2-(1-ethylpiperidin-4-yl)-ethylamino]-pyrimidin-4-yl}-benzo[b]thiophene-4-carboxylic acid cyclopropylamide di-hydrochloride, the title compound is synthesized from 2-[5-methyl-2-(3-piperidin-4-yl-propylamino)-pyrimidin-4-yl]-benzo[b]thiophene-4-carboxylic acid cyclopropylamide and 1-bromo-2-fluoroethane and isolated as a yellow solid. ES+(m/z) 496 [M(free base)+H].

EXAMPLE 131

2-{2-[3-(1-Cyclopropyl-piperidin-4-yl)-propylamino]-5-methylpyrimidin-4-yl}-benzo[b]thiophene-4-carboxylic acid cyclopropylamide di-hydrochloride Using the method of 2-{5-chloro-2-[3-(1-cyclopropylpiperidin-4-yl)-propylamino]-pyrimidin-4-yl}-benzo[b]thiophene-4-carboxylic acid cyclopropylamide di-hydrochloride, the title compound is synthesized from 2-[5-methyl-2-(3-piperidin-4-ylpropylamino)-pyrimidin-4-yl]-benzo[b]thiophene-4-carboxylic acid cyclopropylamide and isolated as a yellow solid. ES+(m/z) 490 [M(free base)+H].

EXAMPLE 132

2-{2-[3-(1-Methylpiperidin-4-yl)-propylamino]-pyrimidin-4-yl}-benzo[b]thiophene-4-carboxylic acid cyclopropylamide di-hydrochloride Using the method of 2-{5-methyl-2-[2-(1-methylpiperidin-4-yl)-ethylamino]-pyrimidin-4-yl}-benzo[b]thiophene-4-carboxylic acid cyclopropylamide di-hydrochloride, the title compound is synthesized from 2-[2-(3-piperidin-4-ylpropylamino)-pyrimidin-4-yl]-benzo[b]thiophene-4-carboxylic acid cyclopropylamide and isolated as a yellow solid. ES+(m/z) 450 [M(free base)+H].

EXAMPLE 133

2-{5-Chloro-2-[3-(4-methylpiperazin-1-yl)-propylamino]-pyrimidin-4-yl}-benzo[b]thiophene-4-carboxylic acid methoxyamide tri-hydrochloride Using the method of 2-{5-chloro-2-[3-(4-methylpiperazin-1-yl)-propylamino]-pyrimidin-4-yl}-benzo[b]thiophene-4-carboxylic acid cyclopropylamide tri-hydrochloride, the title compound is synthesized from 2-(2,5-dichloropyrimidin-4-yl)-benzo[b]thiophene-4-carboxylic acid and isolated as a yellow solid. ES+(m/z) 475 ($^{35}$Cl) and 477 ($^{37}$Cl) [M(free base)+H].

EXAMPLE 134

2-[5-Chloro-2-(3-piperazin-1-yl-propylamino)-pyrimidin-4-yl]-benzo[b]thiophene-4-carboxylic acid methylamide tri-hydrochloride Using the method of 2-[5-fluoro-2-(3-piperidin-4-ylpropylamino)-pyrimidin-4-yl]-benzo[b]thiophene-4-carboxylic acid cyclopropylamide to form the free base. The hydrochloride salt is formed using the method of 2-{5-fluoro-2-[3-(1-methylpiperidin-4-yl)-propylamino]-pyrimidin-4-yl}-benzo[b]thiophene-4-carboxylic acid cyclopropylamide di-hydrochloride. The title compound is synthesized from 2-(2,5-dichloropyrimidin-4-yl)-benzo[b]thiophene-4-carboxylic acid methylamide and isolated as a yellow solid. ES+(m/z) 445 ($^{35}$Cl) and 447 ($^{37}$Cl) [M(free base)+H].

EXAMPLE 135

2-{5-Chloro-2-[3-(4-ethylpiperazin-1-yl)-propylamino]-pyrimidin-4-yl}-benzo[b]thiophene-4-carboxylic acid methylamide tri-hydrochloride Using the method of 2-{5-chloro-2-[3-(4-methylpiperazin-1-yl)-propylamino]-pyrimidin-4-yl}-benzo[b]thiophene-4-carboxylic acid cyclopropylamide tri-hydrochloride, the title compound is synthesized from 2-(2,5-dichloropyrimidin-4-yl)-benzo[b]thiophene-4-carboxylic acid methylamide and 3-(4-ethylpiperazin-1-yl)-propylamine and isolated as a yellow solid. ES+(m/z) 473 ($^{35}$Cl) and 475 ($^{37}$Cl) [M(free base)+H].

EXAMPLE 136

2-{5-Chloro-2-[2-(1-methyl-piperidin-4-yl)-ethylamino]-pyrimidin-4-yl}-benzo[b]thiophene-4-carboxylic acid methylamide di-hydrochloride Using the methods of 2-[5-fluoro-2-(3-piperidin-4-ylpropylamino)-pyrimidin-4-yl]-benzo[b]thiophene-4-carboxylic acid cyclopropylamide and 2-{5-fluoro-2-[3-(1-methylpiperidin-4-yl)-propylamino]-pyrimidin-4-yl}-benzo[b]thiophene-4-carboxylic acid cyclopropylamide di-hydrochloride, the title compound is synthesized from 2-(2,5-dichloropyrimidin-4-yl)-benzo[b]thiophene-4-carboxylic acid methylamide and isolated as a yellow solid. ES+(m/z) 444 ($^{35}$Cl) and 446 ($^{37}$Cl) [M(free base)+H].

EXAMPLE 137

2-{5-Chloro-2-[3-(1-methyl-piperidin-4-yl)-propylamino]-pyrimidin-4-yl}-benzo[b]thiophene-4-carboxylic acid methylamide di-hydrochloride Using the methods of 2-[5-fluoro-2-(3-piperidin-4-ylpropylamino)-pyrimidin-4-yl]-benzo[b]thiophene-4-carboxylic acid cyclopropylamide and 2-{5-fluoro-2-[3-(1-methylpiperidin-4-yl)-propylamino]-pyrimidin-4-yl}-benzo[b]thiophene-4-carboxylic acid cyclopropylamide di-hydrochloride, the title compound is synthesized from 2-(2,5-dichloropyrimidin-4-yl)-benzo[b]thiophene-4-carboxylic acid methylamide and isolated as a yellow solid. ES+(m/z) 458 ($^{35}$Cl) and 460 ($^{37}$Cl) [M(free base)+H].

EXAMPLE 138

2-[5-Bromo-2-(2-piperidin-4-yl-ethylamino)-pyrimidin-4-yl]-benzo[b]thiophene-4-carboxylic acid methylamide Using the method of 2-[5-fluoro-2-(3-piperidin-4-ylpropylamino)-pyrimidin-4-yl]-benzo[b]thiophene-4-carboxylic acid cyclopropylamide, the title compound is synthesized from 2-(5-bromo-2-chloropyrimidin-4-yl)-benzo[b]thiophene-4-carboxylic acid methylamide and isolated as a yellow solid. ES+(m/z) 474 ($^{79}$Br) and 476 ($^{81}$Br) [M+H].

EXAMPLE 139

2-{5-Bromo-2-[2-(1-methylpiperidin-4-yl)-ethylamino]-pyrimidin-4-yl}-benzo[b]thiophene-4-carboxylic acid methylamide di-hydrochloride Using the method of 2-{5-fluoro-2-[3-(1-methylpiperidin-4-yl)-propylamino]-pyrimidin-4-yl}-benzo[b]thiophene-4-carboxylic acid cyclopropylamide di-hydrochloride, the title compound is synthesized from 2-[5-bromo-2-(2-piperidin-4-yl-ethylamino)-pyrimidin-4-yl]-benzo[b]thiophene-4-carboxylic acid methylamide and isolated as a yellow solid. ES+(m/z) 488 ($^{79}$Br) and 490 ($^{81}$Br) [M(free base)+H].

EXAMPLE 140

2-{5-Bromo-2-[2-(1-cyclopropylpiperidin-4-yl)-ethylamino]-pyrimidin-4-yl}-benzo[b]thiophene-4-carboxylic acid methylamide di-hydrochloride Using the method of 2-{5-chloro-2-[3-(1-cyclopropylpiperidin-4-yl)-propylamino]-pyrimidin-4-yl}-benzo[b]thiophene-4-carboxylic acid cyclopropylamide di-hydrochloride, the title compound is synthesized from 2-[5-bromo-2-(2-piperidin-4-yl-ethylamino)-pyrimidin-4-yl]-benzo[b]thiophene-4-carboxylic acid methylamide and isolated as a yellow solid. ES+(m/z) 514 ($^{79}$Br) and 516 ($^{81}$Br) [M(free base)+H].

EXAMPLE 141

2-[5-Bromo-2-(3-piperidin-4-ylpropylamino)-pyrimidin-4-yl]-benzo[b]thiophene-4-carboxylic acid methylamide Using the method of 2-[5-fluoro-2-(3-piperidin-4-ylpropylamino)-pyrimidin-4-yl]-benzo[b]thiophene-4-carboxylic acid cyclopropylamide, the title compound is synthesized from 2-(5-bromo-2-chloropyrimidin-4-yl)-benzo[b]thiophene-4-carboxylic acid methylamide and isolated as a yellow solid. ES+(m/z) 488 ($^{79}$Br) and 490 ($^{81}$Br) [M+H].

EXAMPLE 142

2-{5-Bromo-2-[3-(1-methylpiperidin-4-yl)-propylamino]-pyrimidin-4-yl}-benzo[b]thiophene-4-carboxylic acid methylamide di-hydrochloride Using the method of 2-{5-fluoro-2-[3-(1-methylpiperidin-4-yl)-propylamino]-pyrimidin-4-yl}-benzo[b]thiophene-4-carboxylic acid cyclopropylamide di-hydrochloride, the title compound is synthesized from 2-[5-bromo-2-(3-piperidin-4-yl-propylamino)-pyrimidin-4-yl]-benzo[b]thiophene-4-carboxylic acid methylamide and isolated as a yellow solid. ES+(m/z) 502 ($^{79}$Br) and 504 ($^{81}$Br) [M(free base)+H].

EXAMPLE 143

2-[5-Methyl-2-(3-piperidin-4-ylpropylamino)-pyrimidin-4-yl]-benzo[b]thiophene-4-carboxylic acid methylamide Using the method of 2-[5-fluoro-2-(3-piperidin-4-ylpropylamino)-pyrimidin-4-yl]-benzo[b]thiophene-4-carboxylic acid cyclopropylamide, the title compound is synthesized from 2-(2-chloro-5-methylpyrimidin-4-yl)-benzo[b]thiophene-4-carboxylic acid methylamide and isolated as a yellow solid. ES+(m/z) 424 [M+H].

EXAMPLE 144

2-{5-Methyl-2-[3-(1-methylpiperidin-4-yl)-propylamino]-pyrimidin-4-yl}-benzo[b]thiophene-4-carboxylic acid methylamide di-hydrochloride Using the method of 2-{5-fluoro-2-[3-(1-methylpiperidin-4-yl)-propylamino]-pyrimidin-4-yl}-benzo[b]thiophene-4-carboxylic acid cyclopropylamide di-hydrochloride, the title compound is synthesized from 2-[5-methyl-2-(3-piperidin-4-yl-propylamino)-pyrimidin-4-yl]-benzo[b]thiophene-4-carboxylic acid methylamide and isolated as a yellow solid. ES+(m/z) 438 [M(free base)+H].

EXAMPLE 145

2-{5-Bromo-2-[3-(4-methylpiperazin-1-yl)-propylamino]-pyrimidin-4-yl}-benzo[b]thiophene-4-carboxylic acid methylamide tri-hydrochloride Using the method of 2-{5-chloro-2-[3-(4-methylpiperazin-1-yl)-propylamino]-pyrimidin-4-yl}-benzo[b]thiophene-4-carboxylic acid cyclopropylamide tri-hydrochloride, the title compound is synthesized from 2-(5-bromo-2-chloro-pyrimidin-4-yl)-benzo[b]thiophene-4-carboxylic acid methylamide and isolated as a yellow solid. ES+(m/z) 503 ($^{79}$Br) and 505 ($^{81}$Br) [M(free base)+H].

EXAMPLE 146

2-{5-Bromo-2-[3-(4-methylpiperazin-1-yl)-propylamino]-pyrimidin-4-yl}-benzo[b]thiophene-4-carboxylic acid methylamide tri-hydrochloride Using the method of 2-{5-chloro-2-[3-(4-methylpiperazin-1-yl)-propylamino]-pyrimidin-4-yl}-benzo[b]thiophene-4-carboxylic acid cyclopropylamide tri-hydrochloride, the title compound is synthesized from 2-(5-bromo-2-chloro-pyrimidin-4-yl)-benzo[b]thiophene-4-carboxylic acid methylamide and isolated as a yellow solid. ES+(m/z) 517 ($^{79}$Br) and 519 ($^{81}$Br) [M(free base)+H].

EXAMPLE 147

2-{5-Bromo-2-[2-(2,2,6,6-tetramethylpiperidin-4-ylidene)-ethylamino]-pyrimidin-4-yl}-benzo[b]thiophene-4-carboxylic acid cyclopropylamide di-hydrochloride

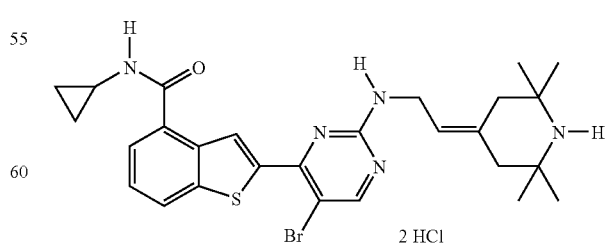

Using the method of 2-{5-chloro-2-[3-(4-methylpiperazin-1-yl)-propylamino]-pyrimidin-4-yl}-benzo[b]thiophene-4-carboxylic acid cyclopropylamide tri-hydrochloride, the title compound is synthesized from 2-(5-bromo-2-chloropyrimidin-4-yl)-benzo[b]thiophene-4-carboxylic acid cyclopropylamide and 2-(2,2,6,6-tetramethylpiperidin-4-ylidene)-ethylamine and isolated as a yellow solid. ES+(m/z) 554 ($^{79}$Br) and 556 ($^{81}$Br) [M(free base)+H].

EXAMPLE 148

2-{5-Chloro-2-[2-(2,2,6,6-tetramethylpiperidin-4-ylidene)-ethylamino]-pyrimidin-4-yl}-benzo[b]thiophene-4-carboxylic acid cyclopropylamide di-hydrochloride Using the method of 2-{5-chloro-2-[3-(4-methylpiperazin-1-yl)-propylamino]-pyrimidin-4-yl}-benzo[b]thiophene-4-carboxylic acid cyclopropylamide tri-hydrochloride, the title compound is synthesized from 2-(2,5-dichloropyrimidin-4-yl)-benzo[b]thiophene-4-carboxylic acid cyclopropylamide and 2-(2,2,6,6-tetramethyl-piperidin-4-ylidene)-ethylamine and isolated as a yellow solid. ES+(m/z) 510 ($^{35}$Cl) and 512 ($^{37}$Cl) [M(free base)+H].

EXAMPLE 149

2-{5-Bromo-2-[2-(4-methylpiperidin-4-yl)-ethylamino]-pyrimidin-4-yl}-benzo[b]thiophene-4-carboxylic acid cyclopropylamide di-hydrochloride A stirred mixture of 2-(5-bromo-2-chloropyrimidin-4-yl)-benzo[b]thiophene-4-carboxylic acid cyclopropylamide (400 mg, 0.979 mmol), 4-(2-aminoethyl)-4-methyl-piperidine-1-carboxylic acid tert-butyl ester (474 mg, 1.96 mmol) and diisopropylethylamine (253 mg, 1.96 mmol) in 1,4-dioxane (10 mL) is heated at 90° C. under nitrogen for 18 hours. At room temperature the mixture is concentrated and the crude product is chromatographed on silica gel, eluting with 3% 2 M NH$_3$/MeOH in dichloromethane, to give 602 mg of 4-{2-[5-bromo-4-(4-cyclopropylcarbamoylbenzo[b]thiophen-2-yl)-pyrimidin-2-ylamino]-ethyl}-4-methylpiperidine-1-carboxylic acid tert-butyl ester. It is then subject to deprotection by dissolving the material (132 mg, 0.220 mmol) in MeOH (10 mL) and dichloromethane (5 mL) and bubbling anhydrous HCl gas for 5 minutes. The hot, yellow solution is allowed to sit at room temperature for 1.5 hours, then concentrated to give the title compound as a yellow solid (126 mg, 100% yield). ES+(m/z) 514 ($^{79}$Br) and 516 ($^{81}$Br) [M(free base)+H].

The following compounds are prepared essentially as described for 2-{5-bromo-2-[2-(4-methylpiperidin-4-yl)-ethylamino]-pyrimidin-4-yl}-benzo[b]thiophene-4-carboxylic acid cyclopropylamide di-hydrochloride and isolated as the di-hydrochloride salt.

| Ex. | Compound | MS (ES+) m/z [M(free base) + H] |
|---|---|---|
| 150 | 2-{5-Chloro-2-[2-(4-methylpiperidin-4-yl)-ethylamino]-pyrimidin-4-yl}-benzo[b]thiophene-4-carboxylic acid methylamide di-hydrochloride | 444 ($^{35}$Cl), 446 ($^{37}$Cl) |
| 151 | 2-{5-Chloro-2-[2-(4-methylpiperidin-4-yl)-ethylamino]-pyrimidin-4-yl}-benzo[b]thiophene-4-carboxylic acid cyclopropylamide di-hydrochloride | 470 ($^{35}$Cl), 472 ($^{37}$Cl) |
| 152 | 2-{5-Methyl-2-[2-(4-methylpiperidin-4-yl)-ethylamino]-pyrimidin-4-yl}-benzo[b]thiophene-4-carboxylic acid cyclopropylamide di-hydrochloride | 450 |
| 153 | 2-{5-Chloro-2-[2-(1,4-dimethylpiperidin-4-yl)-ethylamino]-pyrimidin-4-yl}-benzo[b]thiophene-4-carboxylic acid cyclopropylamide di-hydrochloride | 484 ($^{35}$Cl), 486 ($^{37}$Cl) |
| 154 | 2-{5-Chloro-2-[2-(1,4-dimethylpiperidin-4-yl)-ethylamino]-pyrimidin-4-yl}-benzo[b]thiophene-4-carboxylic acid methylamide di-hydrochloride | 458 ($^{35}$Cl), 460 ($^{37}$Cl) |
| 155 | 2-{2-[2-(1,4-Dimethylpiperidin-4-yl)-ethylamino]-5-methylpyrimidin-4-yl}-benzo[b]thiophene-4-carboxylic acid cyclopropylamide di-hydrochloride | 464 |
| 156 | 2-{5-Chloro-2-[3-(4-methylpiperidin-4-yl)-propylamino]-pyrimidin-4-yl}-benzo[b]thiophene-4-carboxylic acid cyclopropylamide di-hydrochloride | 484 ($^{35}$Cl), 486 ($^{37}$Cl) |
| 157 | 2-{5-Chloro-2-[3-(1,4-dimethylpiperidin-4-yl)-propylamino]-pyrimidin-4-yl}-benzo[b]thiophene-4-carboxylic acid cyclopropylamide di-hydrochloride | 498 ($^{35}$Cl), 500 ($^{37}$Cl) |
| 158 | Racemic 2-{5-Chloro-2-[3-hydroxy-3-(4-methylpiperidin-4-yl)-propylamino]-pyrimidin-4-yl}-benzo[b]thiophene-4-carboxylic acid cyclopropylamide di-hydrochloride | 450 ($^{35}$Cl), 452 ($^{37}$Cl) |
| 159 | 2-{5-Methyl-2-[3-(4-methylpiperidin-4-yl)-propylamino]-pyrimidin-4-yl}-benzo[b]thiophene-4-carboxylic acid cyclopropylamide di-hydrochloride | 464 |
| 160 | 2-{2-[3-(1,4-Dimethylpipendin-4-yl)-propylamino]-5-methylpyrimidin-4-yl}-benzo[b]thiophene-4-carboxylic acid cyclopropylamide di-hydrochloride | 478 |
| 161 | Racemic 2-{5-Chloro-2-[3-(1,4-dimethylpiperidin-4-yl)-3-hydroxypropylamino]-pyrimidin-4-yl}-benzo[b]thiophene-4-carboxylic acid cyclopropylamide di-hydrochloride | 514 ($^{35}$Cl), 516 ($^{37}$Cl) |

EXAMPLE 162

2-{5-Bromo-2-[2-(2,2,6,6-tetramethylpiperidin-4-yl)-ethylamino]-pyrimidin-4-yl}-benzo[b]thiophene-4-carboxylic acid cyclopropylamide di-hydrochloride

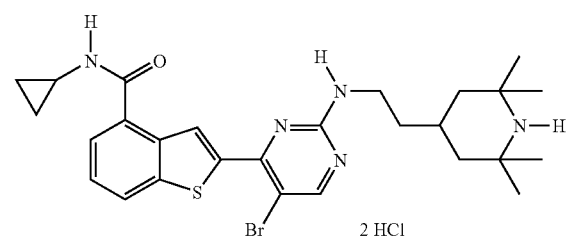

Using the method of 2-{5-chloro-2-[3-(4-methylpiperazin-1-yl)-propylamino]-pyrimidin-4-yl}-benzo[b]thiophene-4-carboxylic acid cyclopropylamide tri-hydrochloride, the title compound is synthesized from 2-(5-bromo-2-chloropyrimidin-4-yl)-benzo[b]thiophene-4-carboxylic acid cyclopropylamide and 2-(2,2,6,6-tetramethyl-piperidin-4-yl)-ethylamine and isolated as a yellow solid. ES+(m/z) 556 ($^{79}$Br) and 558 ($^{81}$Br) [M(free base)+H].

EXAMPLE 163

2-{5-Bromo-2-[2-(1,4-dimethylpiperidin-4-yl)-ethylamino]-pyrimidin-4-yl}-benzo[b]thiophene-4-carboxylic acid cyclopropylamide di-hydrochloride To 2-{5-bromo-2-[2-(4-methylpiperidin-4-yl)-ethylamino]-pyrimidin-4-yl}-benzo[b]thiophene-4-carboxylic acid cyclopropylamide dihydrochloric acid (0.200 g, 0.34 mmol) dissolved in 3:1 MeOH:dichloromethane (8 mL) is added 37.4% aqueous formaldehyde (0.076 mL, 1.02 mmol). After 1 hour, the reaction mixture is cooled in an ice bath and sodium borohydride is added in portions over two minutes. The reaction proceeds for 1 hour in an ice bath and 1 hour at room temperature. By TLC an intermediate is present and an additional equivalent of sodium borohydride is added at 0° C. After 30 minutes the entire reaction mixture is loaded onto a silica gel column and chromatographed, eluting with 3-7% (2 M NH$_3$ in MeOH) in dichloromethane to give 116 mg, 64% yield, of the methylated product. It is converted to the titled compound by treating with concentrated HCl solution and isolated as a yellow solid. ES+(m/z) 528 ($^{79}$Br) and 530 ($^{81}$Br) [M(free base)+H].

EXAMPLE 164

2-{5-Methyl-2-[3-(4-methylpiperazin-1-yl)-propylamino]-pyrimidin-4-yl}-benzo[b]thiophene-6-carboxylic acid methylamide tri-hydrochloride A mixture of 2-{5-methyl-2-[3-(4-methylpiperazin-1-yl)-propylamino]-pyrimidin-4-yl}-benzo[b]thiophene-6-carboxylic acid (209 mg, 0.420 mmol), 2.0 M methylamine in THF (0.80 mL, 1.6 mmol), diisopropylethylamine (0.42 mL, 2.4 mmol), (benzotriazol-1-yloxy)tris(dimethylamino)phosphonium hexafluorophosphate (314 mg, 0.710 mmol), and lithium chloride (222 mg, 5.23 mmol) is stirred in DMF (5 mL) at 25° C. for 20 hours. The solvent is removed and the residue is subjected to chromatography on silica gel, eluting with 2.0 M NH$_3$/MeOH/dichloromethane 0-10%, to give the desired methylamide as a yellow solid (80 mg, 43% yield). The free base is dissolved in methanol (2 mL) and dichloromethane (2 mL), HCl/diethyl ether solution (3 mL, 1.0 M) is added and the mixture is stirred for 10 minutes. The yellow solid is filtered, washed with diethyl ether, and dried under vacuum at 50° C. for 6 hours to give the title compound as a yellow solid (94 mg, 100% yield). ES+(m/z) 439 [M(free base)+H].

EXAMPLE 165

2-{5-Methyl-2-[3-(4-methylpiperazin-1-yl)-propylamino]-pyrimidin-4-yl}-benzo[b]thiophene-6-carboxylic acid pyridine-3-ylamide tetra-hydrochloride A mixture of 2-{5-methyl-2-[3-(4-methylpiperazin-1-yl)-propylamino]-pyrimidin-4-yl}-benzo[b]thiophene-6-carboxylic acid (250 mg, 0.500 mmol), 3-aminopyridine (147 mg, 1.56 mmol), diisopropylethylamine (0.27 mL), (benzotriazol-1-yloxy)tris(dimethylamino)phosphonium hexafluorophosphate (278 mg, 0.630 mmol), and lithium chloride (226 mg, 5.34 mmol) is stirred in DMF (5 mL) at 25° C. for 20 hours. The solvent is removed and the residue is subjected to chromatography on silica gel, eluting with 2.0 M NH$_3$/MeOH in dichloromethane 0-10%, to give a solid. The resulting solid is dissolved in methylene chloride (2 mL) and diethyl ether is added until a precipitate forms. After filtration and drying, the free base is obtained as a solid (61 mg, 24% yield). It is dissolved in methanol (1.5 mL) and dichloromethane (1.5 mL), HCl/diethyl ether solution (3 mL, 1.0 M) is added and the mixture is stirred for 10 minutes. The resulting precipitate is filtered, washed with diethyl ether, and dried under vacuum at 50° C. for 3 hours to give the title compound as a brown solid (35 mg, 11% yield). ES+(m/z) 502 [M(free base)+H].

EXAMPLE 166

2-[5-Methyl-2-(3-piperazin-1-ylpropylamino)-pyrimidin-4-yl]-benzo[b]thiophene-6-carboxylic acid methylamide tri-hydrochloride A mixture of 2-(2-chloro-5-methylpyrimidin-4-yl)-benzo[b]thiophene-6-carboxylic acid methylamide (263 mg, 0.830 mmol), 4-(3-aminopropyl)-piperazine-1-carboxylic acid tert-butyl ester (358 mg, 1.47 mmol) and diisopropylethylamine (0.44 mL) in 1,4-dioxane (10 mL) is heated at 95° C. for 20 hours. The solvent is removed after cooling and the residue is subjected to chromatography on silica gel, eluting with 2.0 M NH$_3$/MeOH in dichloromethane 0-10%, to give 4-{3-[5-methyl-4-(6-methylcarbamoyl-benzo[b]thiophen-2-yl)-pyrimidin-2-ylamino]-propyl}-piperazine-1-carboxylic acid tert-butyl ester (191 mg, 44% yield). The intermediate is dissolved in THF (8 mL) and 5 N hydrochloric acid (5 mL) is added. The solution is heated at 70° C. for 4.5 hours and then cooled before evaporating the solvent. Methanol is added to the residue and the mixture is sonicated for 30 minutes. The solid is filtered and washed with diethyl ether, then dried in a vacuum oven at 50° C. for 18 hours to give the title compound (129 mg, 66% yield). ES+(m/z) 425 [M(free base)+H].

The following compounds are prepared essentially as described for 2-[5-methyl-2-(3-piperazin-1-ylpropylamino)-pyrimidin-4-yl]-benzo[b]thiophene-6-carboxylic acid methylamide tri-hydrochloride and isolated as the di or tri-hydrochloride salt.

| Ex. | Compound | MS (ES+) m/z [M(free base) + H] |
|---|---|---|
| 167 | 2-{5-Chloro-2-[3-(4-methylpiperazin-1-yl)-propylamino]-pyrimidin-4-yl}-benzo[b]thiophene-6-carboxylic acid thiazol-2-ylamide tri-hydrochloride | 528 ($^{35}$Cl), 530 ($^{37}$Cl) |
| 168 | 2-[5-Chloro-2-(3-piperazin-1-yl-propylamino)-pyrimidin-4-yl]-benzo[b]thiophene-6-carboxylic acid dimethylamide tri-hydrochloride | 459 ($^{35}$Cl), 461 ($^{37}$Cl) |
| 169 | 2-{5-Chloro-2-[3-(4-methylpiperazin-1-yl)-propylamino]-pyrimidin-4-yl}-benzo[b]thiophene-6-carboxylic acid dimethylamide tri-hydrochloride | 473 ($^{35}$Cl), 475 ($^{37}$Cl) |
| 170 | 2-[5-Chloro-2-(3-piperazin-1-ylpropylamino)-pyrimidin-4-yl]-benzo[b]thiophene-6-carboxylic acid methylamide tri-hydrochloride | 445 ($^{35}$Cl), 447 ($^{37}$Cl) |
| 171 | 2-{5-Chloro-2-[3-(4-methylpiperazin-1-yl)-propylamino]-pyrimidin-4-yl}-benzo[b]thiophene-6-carboxylic acid methylamide tri-hydrochloride | 459 ($^{35}$Cl), 461 ($^{37}$Cl) |
| 172 | 2-[5-Methyl-2-(3-piperidin-4-ylpropylamino)-pyrimidin-4-yl]-benzo[b]thiophene-6-carboxylic acid methylamide di-hydrochloride | 424 |
| 173 | 2-{5-Methyl-2-[3-(1-methylpiperidin-4-yl)-propylamino]-pyrimidin-4-yl}-benzo[b]thiophene-6-carboxylic acid methylamide di-hydrochloride | 438 |
| 174 | 2-(2-{3-[1-(2-Fluoroethyl)-piperidin-4-yl]-propylamino}-5-methylpyrimidin-4-yl)-benzo[b]thiophene-6-carboxylic acid methylamide di-hydrochloride | 470 |
| 175 | 2-{5-Chloro-2-[3-(1-methylpiperidin-4-yl)-propylamino]-pyrimidin-4-yl}-benzo[b]thiophene-6-carboxylic acid methylamide di-hydrochloride | 458 ($^{35}$Cl), 460 ($^{37}$Cl) |
| 176 | (2-{5-Methyl-2-[2-(1-methylpiperidin-4-yl)-ethylamino]-pyrimidin-4-yl}-benzo[b]thiophen-6-yl)-morpholin-4-yl-methanone di-hydrochloride | 480 |
| 177 | N-(2-{2-[3-(4-Methylpiperazin-1-yl)-propylamino]-pyrimidin-4-yl}-benzo[b]thiophen-6-ylmethyl)-methanesulfonamide tri-hydrochloride | 475 |
| 178 | N-(2-{5-Methyl-2-[3-(4-methylpiperazin-1-yl)-propylamino]-pyrimidin-4-yl}-benzo[b]thiophen-6-ylmethyl)-methanesulfonamide tri-hydrochloride | 489 |
| 179 | C,C,C-Trifluoro-N-(2-{5-methyl-2-[3-(4-methylpiperazin-1-yl)-propylamino]-pyrimidin-4-yl}-benzo[b]thiophen-6-ylmethyl)-methanesulfonamide tri-hydrochloride | 543 |

EXAMPLE 180

{2-[5-Methyl-2-(2-piperidin-4-ylethylamino)-pyrimidin-4-yl]-benzo[b]thiophen-6-yl}-morpholin-4-ylmethanone Using the method of 2-[5-bromo-2-(2-piperidin-4-ylethylamino)-pyrimidin-4-yl]-benzo[b]thiophene-4-carboxylic acid cyclopropylamide, the title compound is synthesized from [2-(2-chloro5-methylpyrimidin-4-yl)-benzo[b]thiophen-6-yl]-morpholin-4-yl-methanone and 4-(2-aminoethyl)-piperidine-1-carboxylic acid tert-butyl ester and isolated as a yellow solid. ES+(m/z) 466 [M+H].

EXAMPLE 181

N-(2-{5-Chloro-2-[3-(4-methylpiperazin-1-yl)-propylamino]-pyrimidin-4-yl}-benzo[b]thiophen-6-ylmethyl)-methanesulfonamide tri-trifluoroacetate Into a vial is added [4-(6-aminomethyl-benzo[b]thiophen-2-yl)-5-chloropyrimidin-2-yl]-[3-(4-methylpiperazin-1-yl)-propyl]-amine (22.6 mg, 0.0524 mmol) in dichloromethane (1 mL), diisopropylethylamine (7.5 mg, 0.0578 mmol) in dichloromethane (0.5 mL) and methanesulfonyl chloride (8.24 mg, 0.0578 mmol) in dichloromethane (0.5 mL). The mixture is placed in an orbital shaker overnight. The mixture is concentrated under reduced pressure and subjected to reverse phase purification, eluting with 10-60% 0.1% TFA in CH$_3$CN/0.1% TFA in water on a C18 Symmetry column, to give the title compound as a yellow solid (24.8 mg, 56% yield). ES+(m/z) 509 ($^{35}$Cl) and 511 ($^{37}$Cl) [M(free base)+H].

Using the method of N-(2-{5-chloro-2-[3-(4-methylpiperazin-1-yl)-propylamino]-pyrimidin-4-yl}-benzo[b]thiophen-6-ylmethyl)-methanesulfonamide tri-trifluoroacetate, the following compounds are synthesized and isolated as the tri-trifluoroacetate salt.

| Ex. | Compound | MS (ES+) m/z [M(free base) + H] |
|---|---|---|
| 182 | N-(2-{5-Chloro-2-[3-(4-methylpiperazin-1-yl)-propylamino]-pyrimidin-4-yl}-benzo[b]thiophen-6-ylmethyl)-C-phenyl-methanesulfonamide tri-trifluoroacetate | 585 ($^{35}$Cl), 587 ($^{37}$Cl) |
| 183 | 2,2,2-Trifluoroethanesulfonic acid (2-{5-chloro-2-[3-(4-methylpiperazin-1-yl)-propylamino]-pyrimidin-4-yl}-benzo[b]thiophen-6-ylmethyl)-amide tri-trifluoroacetate | 577 ($^{35}$Cl), 579 ($^{37}$Cl) |
| 184 | Propane-1-sulfonic acid (2-{5-chloro-2-[3-(4-methylpiperazin-1-yl)-propylamino]-pyrimidin-4-yl}-benzo[b]thiophen-6-ylmethyl)-amide trifluoroacetate | 537 ($^{35}$Cl), 539 ($^{37}$Cl) |
| 185 | Cyclopropanesulfonic acid (2-{5-chloro-2-[3-(4-methylpiperazin-1-yl)-propylamino]-pyrimidin-4-yl}-benzo[b]thiophen-6-ylmethyl)-amide tri-trifluoroacetate | 535 ($^{35}$Cl), 537 ($^{37}$Cl) |

EXAMPLE 186

N-(2-{5-Chloro-2-[3-(4-methylpiperazin-1-yl)-propylamino]-pyrimidin-4-yl}-benzo[b]thiophen-6-ylmethyl)-methanesulfonamide tri-hydrochloride Into a solution of [4-(6-aminomethylbenzo[b]thiophen-2-yl)-5-chloropyrimidin-2-yl]-[3-(4-methylpiperazin-1-yl)-propyl]-amine (175 mg, 0.406 mmol) in dichloromethane (5 mL) is added diisopropylamine (115 mg, 0.893 mmol) followed by methanesulfonyl chloride (93.0 mg, 0.812 mmol) in dichloromethane (8 mL). The mixture is placed in a shaker block for 3 days. After concentration and reverse phase purification, eluting with 10-60% 0.1% TFA in CH$_3$CN/0.1% TFA in water using a C18 Symmetry column, the title compound is obtained as a yellow solid of the TFA salt (236 mg, 68% yield). The TFA salt is dissolved in MeOH (20 mL) and Silicycle carbonate on silica gel (2.5 g, ca 6 eq) is added and the mixture is shaken. After 3 hours, the mixture is filtered and concentrated under reduced pressure to yield the free base as a white solid (140 mg). The free base is dissolved in MeOH/THF (1:1, 100 mL) and 4 N HCl in 1,4-dioxane (1.1 mL) is added. After stirring for 5 minutes the mixture is concentrated under reduced pressure to yield the title compound as a yellow solid (144 mg, 57% yield). ES+(m/z) 509 ($^{35}$Cl) and 511 ($^{37}$Cl) [M(free base)+H].

EXAMPLE 187

Cyclopropanesulfonic acid (2-{5-chloro-2-[3-(4-methylpiperazin-1-yl)-propylamino]-pyrimidin-4-yl}-benzo[b]thiophen-6-ylmethyl)-amide tri-hydrochloride Into a solution of [4-(6-aminomethylbenzo[b]thiophen-2-yl)-5-chloropyrimidin-2-yl]-[3-(4-methylpiperazin-1-yl)-propyl]-amine (175 mg, 0.406 mmol) in dichloromethane (5 mL) is added diisopropylamine (115 mg, 0.893 mmol) followed by cyclopropanesulfonyl chloride (114 mg, 0.812 mmol) in dichloromethane (8 mL). The mixture is placed in a shaker block and shaken for 3 days. After concentration and reverse phase purification, eluting with 10-60% 0.1% TFA in CH$_3$CN/0.1% TFA in water using a C18 Symmetry column, the title compound is obtained as a yellow solid of the TFA salt. The TFA salt is dissolved in MeOH (25 mL) and Silicycle carbonate on silica gel (3.1 g, ca 7 eq) is added and the mixture is shaken. After 3 hours, the mixture is filtered and concentrated under reduced pressure to yield the free base as a white solid (192 mg). The free base is dissolved in MeOH/THF (1:1, 100 mL) and 4N HCl in 1,4-dioxane (1.1 mL) is added. After stirring for 5 minutes the mixture is concentrated under reduced pressure to yield the title compound as a yellow solid (203 mg, 78% yield). ES+(m/z) 535 ($^{35}$Cl) and 537 ($^{37}$Cl) [M(free base)+H].

EXAMPLE 188

1-(2-{5-Chloro-2-[3-(4-methylpiperazin-1-yl)-propylamino]-pyrimidin-4-yl}-benzo[b]thiophen-6-ylmethyl)-3-propylurea tri-trifluoroacetate Into a vial is added [4-(6-aminomethylbenzo[b]thiophen-2-yl)-5-chloropyrimidin-2-yl]-[3-(4-methylpiperazin-1-yl)-propyl]-amine (22.6 mg, 0.0524 mmol) in dichloromethane (1 mL) and propylisocyanate (4.92 mg, 0.0578 mmol) in dichloromethane (0.5 mL). The mixture is placed in an orbital shaker overnight. The mixture is concentrated under reduced pressure and subjected to reverse phase purification, eluting with 10-60% 0.1% TFA in CH$_3$CN/0.1% TFA in water using a C18 Symmetry column, to give the title compound as a yellow solid (35.4 mg, 79% yield). ES+(m/z) 516 ($^{35}$Cl) and 518 ($^{37}$Cl) [M(free base)+H].

Using the method of 1-(2-{5-chloro-2-[3-(4-methylpiperazin-1-yl)-propylamino]-pyrimidin-4-yl}-benzo[b]thiophen-6-ylmethyl)-3-propylurea tri-trifluoroacetate, the following compounds are synthesized and isolated as the tri-trifluoroacetate salt.

| Ex. | Compound | MS (ES+) m/z [M(free base) + H] |
|---|---|---|
| 189 | 1-(2-{5-Chloro-2-[3-(4-methylpiperazin-1-yl)-propylamino]-pyrimidin-4-yl}-benzo[b]thiophen-6-ylmethyl)-3-cyclohexylurea tri-trifluoroacetate | 556 ($^{35}$Cl), 558 ($^{37}$Cl) |
| 190 | 1-Benzyl-3-(2-{5-chloro-2-[3-(4-methylpiperazin-1-yl)-propylamino]-pyrimidin-4-yl}-benzo[b]thiophen-6-ylmethyl)-urea tri-trifluoroacetate | 564 ($^{35}$Cl), 566 ($^{37}$Cl) |
| 191 | 1-(2-{5-Chloro-2-[3-(4-methyl-piperazin-1-yl)-propylamino]-pyrimidin-4-yl}-benzo[b]thiophen-6-ylmethyl)-3-(4-methylbenzyl)-urea tri-trifluoroacetate | 578 ($^{35}$Cl), 580 ($^{37}$Cl) |
| 192 | 1-(2-{5-Chloro-2-[3-(4-methylpiperazin-1-yl)-propylamino]-pyrimidin-4-yl}-benzo[b]thiophen-6-ylmethyl)-3-(4-fluorobenzyl)-urea tri-trifluoroacetate | 582 ($^{35}$Cl), 584 ($^{37}$Cl) |
| 193 | 1-(2-{5-Chloro-2-[3-(4-methylpiperazin-1-yl)-propylamino]-pyrimidin-4-yl}-benzo[b]thiophen-6-ylmethyl)-3-(4-methoxybenzyl)-urea tri-trifluoroacetate | 594 ($^{35}$Cl), 596 ($^{37}$Cl) |

EXAMPLE 194

[4-(6-Bromobenzo[b]thiophen-2-yl)-5-chloropyrimidin-2-yl]-[3-(4-methylpiperazin-1-yl)-propyl]-amine tri-hydrochloride Using the method of [4-(benzo[b]thiophen-2-yl)-pyrimidin-2-yl]-[3-(4-methylpiperazin-1-yl)-propyl]-amine, the title compound is synthesized from 4-(6-bromobenzo[b]thiophen-2-yl)-2,5-dichloropyrimidine and isolated as a light orange solid. ES+(m/z) 480 ($^{35}$Cl, $^{79}$Br), 482 ([$^{37}$Cl, $^{79}$Br] and [$^{35}$Cl, $^{81}$Br]) and 484 ($^{37}$Cl, $^{81}$Br) [M(free base)+H].

EXAMPLE 195

1-(2-{5-Chloro-2-[3-(4-methylpiperazin-1-yl)-propylamino]-pyrimidin-4-yl}-benzo[b]thiophen-6-yl)-pyrrolidin-2-one A microwave tube is charged with [4-(6-bromobenzo[b]thiophen-2-yl)-5-chloropyrimidin-2-yl]-[3-(4-methylpiperazin-1-yl)-propyl]-amine (0.045 g, 0.094 mmol), 1.5 equivalent of 2-pyrrolidinone (0.012 g, 0.14 mmol), 4 mol % of palladium acetate (0.010 g, 0.0040 mmol), 8 mol % of Xantphos (0.050 g, 0.0080 mmol), 1.5 equivalent of cesium carbonate (0.049 g, 0.15 mmol) and acetonitrile (2 mL). The reaction is sealed and heated under microwave condition at 150° C. for 15 minutes, cooled down, filtered and then evaporated to furnish a red oil. The crude material is subjected to reverse phase purification, eluting with 20-95% $CH_3CN$/0.01 N $NH_4HCO_3$ in water, using a C18 Xterra column, to provide the title compound as a pale yellow solid (0.012 g, 23% yield). ES+(m/z) 485 ($^{35}Cl$) and 487 ($^{37}Cl$) [M+H].

Using the method of 1-(2-{5-chloro-2-[3-(4-methylpiperazin-1-yl)-propylamino]-pyrimidin-4-yl}-benzo[b]thiophen-6-yl)-pyrrolidin-2-one, the following compounds are synthesized and isolated as the free base.

| Ex. | Compound | MS (ES+) m/z [M + H] |
|---|---|---|
| 196 | Cyclopropanecarboxylic acid (2-{5-chloro-2-[3-(4-methylpiperazin-1-yl)-propylamino]-pyrimidin-4-yl}-benzo[b]thiophen-6-yl)-amide | 485 ($^{35}Cl$), 487 ($^{37}Cl$) |
| 197 | Piperidine-4-carboxylic acid (2-{5-chloro-2-[3-(4-methylpiperazin-1-yl)-propylamino]-pyrimidin-4-yl}-benzo[b]thiophen-6-yl)-amide | 528 ($^{35}Cl$), 530 ($^{37}Cl$) |

EXAMPLE 198

2-(1H-Indol-3-yl)-N-(2-{2-[3-(4-methylpiperazin-1-yl)-propylamino]-pyrimidin-4-yl}-benzo[b]thiophen-6-yl)-acetamide

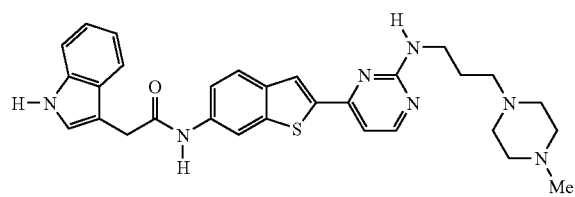

A microwave tube is charged with [4-(6-bromobenzo[b]thiophen-2-yl)-pyrimidin-2-yl]-[3-(4-methylpiperazin-1-yl)-propyl]-amine (0.070 g, 0.16 mmol), 1.5 equivalent of 2-(1H-indol-3-yl)acetamide (0.041 g, 0.24 mmol), 4 mol % of tris(dibenzylideneacetone)dipalladium(0) (5.8 mg, 0.0063 mmol), 8 mol % of Xantphos (7.3 mg, 0.013 mmol), 1.5 equivalent of cesium carbonate (77 mg, 0.24 mmol) and acetonitrile (2 mL). The reaction is sealed and heated under microwave condition at 150° C. for 5 minutes, cooled down, filtered and then evaporated to furnish a red oil. This material is subjected to reverse phase purification, eluting with 20-95% $CH_3CN$/0.01 M $NH_4HCO_3$ in water using a C18 Xterra column, to provide the title compound as a pale yellow solid (23 mg, 26% yield). ES+(m/z) 540 [M+H].

Using the method of 2-(1H-indol-3-yl)-N-(2-{2-[3-(4-methylpiperazin-1-yl)-propylamino]-pyrimidin-4-yl}-benzo[b]thiophen-6-yl)-acetamide, the following compounds are synthesized and isolated as the free base.

| Ex. | Compound | MS (ES+) m/z [M + H] |
|---|---|---|
| 199 | (R,S)-1-(2-{2-[3-(4-Methylpiperazin-1-yl)-propylamino]-pyrimidin-4-yl}-benzo[b]thiophen-6-yl)-5-oxopyrrolidine-2-carboxylic acid ethyl ester | 523 |
| 200 | 2-[4-(2-Hydroxy-3-isopropylaminopropoxy)-phenyl]-N-(2-{2-[3-(4-methylpiperazin-1-yl)-propylamino]-pyrimidin-4-yl}-benzo[b]thiophen-6-yl)-acetamide | 632 |

EXAMPLE 201

{5-Chloro-4-[6-(pyridin-2-ylamino)-benzo[b]thiophen-2-yl]pyrimidin-2-yl}-[3-(4-methylpiperazin-1-yl)-propyl]-amine A microwave tube is charged with [4-(6-bromobenzo[b]thiophen-2-yl)-5-chloropyrimidin-2-yl]-[3-(4-methylpiperazin-1-yl)-propyl]-amine (45 mg, 0.094 mmol), 2.5 equivalent of pyridin-2-amine (28 mg, 0.30 mmol), 2 mol % of tris(dibenzylideneacetone)dipalladium(0) (1.7 mg, 0.0020 mmol), 6 mol % of Xantphos (3.5 mg, 0.0060 mmol), 2.5 equivalent of cesium carbonate (77 mg, 0.24 mmol) and acetonitrile (2 mL). The reaction is sealed and heated under microwave condition at 150° C. for 15 minutes, cooled down, filtered and then evaporated to furnish a red oil. The crude material is subjected to reverse phase purification, eluting with 10-70% $CH_3CN$/0.01 M $NH_4HCO_3$ in water using a C18 Xterra column, to give the title compound as a pale yellow solid (15 mg, 33% yield). ES+(m/z) 494 ($^{35}Cl$) and 496 ($^{37}Cl$) [M+H].

EXAMPLE 202

N-Methyl-3-(2-{2-[3-(4-methylpiperazin-1-yl)-propylamino]-pyrimidin-4-yl}-benzo[b]thiophen-6-yl)-benzamide A microwave tube is charged with [4-(6-bromobenzo[b]thiophen-2-yl)-pyrimidin-2-yl]-[3-(4-methylpiperazin-1-yl)-propyl]-amine (41 mg, 0.092 mmol), 1.6 equivalent of 3-(methylcarbamoyl)phenylboronic acid (27 mg, 0.15 mmol), 5 mol % of tetrakis(triphenylphosphine)palladium(0) (5.0 mg, 0.0046 mmol), 1.2 equivalent of $NaHCO_3$ (10 mg, 0.11 mmol) and 2:1 DMSO/$H_2O$ solution (3 mL). The reaction is sealed and heated under microwave condition at 170° C. for 20 minutes, cooled down, filtered through SCX column and washed several time with dichloromethane/MeOH (1:1). The product is then released with 0.1 M $NH_3$ solution in MeOH, collected and evaporated to give a brown oil. The oil is subjected to reverse phase purification, eluting with 5-95% $CH_3CN$/0.01 N $NH_4HCO_3$ in water using a C18 Xterra column, to give the title compound as a pale yellow solid (10 mg, 40% yield). ES+(m/z) 501 [M+H].

EXAMPLE 203

2-{5-Methyl-2-[3-(4-methylpiperazin-1-yl)-propylamino]-pyrimidin-4-yl}-benzo[b]thiophene-6-carboxylic acid (3-fluorophenyl)-amide To a suspension of polymer-bound tetrafluorophenol (3.5 g, 4.5 mmol) in dry DMF (35 mL) is added 2-{5-methyl-2-[3-(4-methylpiperazin-1-yl)-propylamino]-pyrimidin-4-yl}-benzo[b]thiophene-6-carboxylic acid (3.38 g, 6.67 mmol) and diisopropylethylamine (2.4 mL, 14 mmol), followed by 4-(N,N-dimethylamino)pyridine (0.331 g, 2.71 mmol) in dry dichloromethane (75 mL). The reaction is shaken for 10 minutes. This is followed by addition of N,N-diisopropylcarbodiimide (0.173 mL, 1.12 mmol) in dry dichloromethane (35 mL) and the resulting mixture is mixed on a Quest 210 for 3 hours at room temperature. The suspension is then filtered and the resin is washed with DMF (3×3 mL), dichloromethane (3×3 mL), isopropanol (3×3 mL) and dry DMF (2×3 mL) and dried to afford polymer-bound active ester. To the polymer-bound active ester (0.100 g, 0.129 mmol) is added a solution of 3-fluoroaniline (15 mg, 0.13 mmol) in dry DMF (2.5 mL) and the mixture is stirred at room temperature for 3 hours. The solution is filtered, and the resin collected. The resin is washed with DMF (3×3 mL). The combined filtrate is concentrated to afford the desired amide, which is subjected to reverse phase purification eluting with 10-70% $CH_3CN$/0.01 N $NH_4HCO_3$ in water using a C18 Xterra column, to provide the title compound as a pale yellow solid (9.5 mg, 10% yield). ES+(m/z) 519 [M+H].

Using the method of 2-{5-methyl-2-[3-(4-methylpiperazin-1-yl)-propylamino]-pyrimidin-4-yl}-benzo[b]thiophene-6-carboxylic acid (3-fluorophenyl)-amide, the following compounds are synthesized and isolated as the free base.

| Ex. | Compound | MS (ES+) m/z [M + H] |
|---|---|---|
| 204 | 2-{5-Methyl-2-[3-(4-methylpiperazin-1-yl)-propylamino]-pyrimidin-4-yl}-benzo[b]thiophene-6-carboxylic acid (2-hydroxy-2-phenylethyl)-amide | 545 |
| 205 | 2-{5-Methyl-2-[3-(4-methylpiperazin-1-yl)-propylamino]-pyrimidin-4-yl}-benzo[b]thiophene-6-carboxylic acid [2-(1H-imidazol-4-yl)-ethyl]-amide | 519 |
| 206 | 2-{5-Methyl-2-[3-(4-methylpiperazin-1-yl)-propylamino]-pyrimidin-4-yl}-benzo[b]thiophene-6-carboxylic acid (6-chloropyridin-3-ylmethyl)-amide | 550 ($^{35}$Cl), 552 ($^{37}$Cl) |

Using the method of 2-{5-methyl-2-[3-(4-methylpiperazin-1-yl)-propylamino]-pyrimidin-4-yl}-benzo[b]thiophene-6-carboxylic acid (3-fluorophenyl)-amide, the following compounds are synthesized from 2-{5-chloro-2-[3-(4-methylpiperazin-1-yl)-propylamino]-pyrimidin-4-yl}-benzo[b]thiophene-6-carboxylic acid and isolated as the free base.

| Ex. | Compound | MS (ES+) m/z [M + H] |
|---|---|---|
| 207 | 2-{5-Chloro-2-[3-(4-methylpiperazin-1-yl)-propylamino]-pyrimidin-4-yl}-benzo[b]thiophene-6-carboxylic acid pyridin-3-ylamide | 522 ($^{35}$Cl), 524 ($^{37}$Cl) |
| 208 | 2-{5-Chloro-2-[3-(4-methylpiperazin-1-yl)-propylamino]-pyrimidin-4-yl}-benzo[b]thiophene-6-carboxylic acid (2-hydroxy-2-phenylethyl)-amide | 565 ($^{35}$Cl), 567 ($^{37}$Cl) |
| 209 | 2-{5-Chloro-2-[3-(4-methylpiperazin-1-yl)-propylamino]-pyrimidin-4-yl}-benzo[b]thiophene-6-carboxylic acid (furan-2-ylmethyl)-amide | 525 ($^{35}$Cl), 527 ($^{37}$Cl) |
| 210 | 2-{5-Chloro-2-[3-(4-methylpiperazin-1-yl)-propylamino]-pyrimidin-4-yl}-benzo[b]thiophene-6-carboxylic acid [2-(1H-imidazol-4-yl)-ethyl]-amide | 539 ($^{35}$Cl), 541 ($^{37}$Cl) |
| 211 | 2-{5-Chloro-2-[3-(4-methylpiperazin-1-yl)-propylamino]-pyrimidin-4-yl}-benzo[b]thiophene-6-carboxylic acid (6-chloropyridin-3-ylmethyl)-amide | 570 ($^{35}$Cl, $^{35}$Cl), 572 ($^{35}$Cl, $^{37}$Cl), 574 ($^{37}$Cl, $^{37}$Cl) |

EXAMPLE 212

N-(2-{5-methyl-2-[3-(4-methylpiperazin-1-yl)-propylamino]-pyrimidin-4-yl}-benzo[b]thiophen-6-yl)-methanesulfonamide tri-hydrochloride 4-(6-Aminobenzo[b]thiophen-2-yl)-5-methylpyrimidin-2-yl]-[3-(4-methylpiperazin-1-yl)-propyl]-amine (160 mg, 0.400 mmol) is placed in pyridine (5 mL) and methanesulfonyl chloride (300 µL) is added. The reaction is refluxed for one hour. After cooling, saturated sodium carbonate solution (1 mL) is added and the solvent is removed. The residue is purified by reverse phase chromatography (Kromasil column, eluting with 95% (0.03% HCl/H$_2$O)/5% CH$_3$CN to 100% CH$_3$CN. The resulting product is dried in a vacuum oven at 50° C. for 20 hours to give the title compound as a brown solid (33.8 mg, 18% yield). ES+(m/z) 475 [M(free base)+H].

EXAMPLE 213

1-Methylpiperidine-4-carboxylic acid {3-[5-chloro-4-(4-cyclopropylcarbamoyl-benzo[b]thiophen-2-yl)-pyrimidin-2-ylamino]-propyl}-amide A stirred suspension of piperidine-4-carboxylic acid {3-[5-chloro-4-(4-cyclopropylcarbamoylbenzo[b]thiophen-2-yl)-pyrimidin-2-ylamino]-propyl}-amide (231 mg, 0.450 mmol) in 1,2-dichloroethane (3 mL) and methanol (3 mL) is treated at room temperature with aqueous 37% formaldehyde (0.200 mL, 3.02 mmol) in the presence of sodium triacetoxyborohydride (165 mg, 0.779 mmol) for 24 hours. The mixture is then concentrated under reduced pressure, and subjected to chromatographic purification on silica gel, eluting with 2 M NH$_3$/MeOH in dichloromethane: 8-15%, to provide the title compound (40 mg, 17% yield). ES+(m/z) 527 ($^{35}$Cl) and 529 ($^{37}$Cl) [M+H].

EXAMPLE 214

(S)-Pyrrolidine-3-carboxylic acid {3-[5-chloro-4-(4-cyclopropylcarbamoyl-benzo[b]thiophen-2-yl)-pyrimidin-2-ylamino]-propyl}-amide

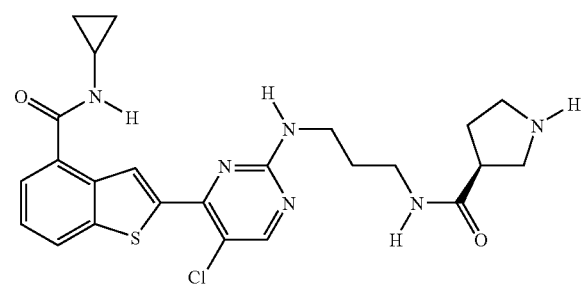

A stirred suspension of 2-[2-(3-aminopropylamino)-5-chloropyrimidin-4-yl]-benzo[b]thiophene-4-carboxylic acid cyclopropylamide (500 mg, 1.24 mmol) in dichloromethane (30 mL) is treated at room temperature with (S)-pyrrolidine-1,3-dicarboxylic acid 1-tert-butyl ester (333 mg, 1.55 mmol), N,N-diisopropylethylamine (0.220 mL, 1.26 mmol), 1-(3-diethylaminopropyl)-3-ethylcarbodiimide hydrochloride (240 mg, 1.25 mmol) and 1-hydroxybenzotriazole (171 mg, 1.21 mmol) for 24 hours. The mixture is then diluted with dichloromethane (30 mL), filtered, washed with water (30 mL) and diethyl ether (30 mL), and dried to provide (S)-3-{3-[5-chloro-4-(4-cyclopropylcarbamoyl-benzo[b]thiophen-2-yl)-pyrimidin-2-ylamino]-propylcarbamoyl}-pyrrolidine-1-carboxylic acid tert-butyl ester (670 mg, 90%). A stirred mixture of this intermediate (665 mg, 1.11 mmol) in dichloromethane (25 mL) is treated at room temperature with TFA (2.5 mL) for 72 hours. The mixture is then concentrated under reduced pressure and subjected to chromatographic purification on silica gel, eluting with 2 M NH$_3$/MeOH in dichloromethane: 16-40%, to provide the title compound (474 mg, 82% yield). ES+(m/z) 499 ($^{35}$Cl) and 501 ($^{37}$Cl) [M+H].

EXAMPLE 215

(S)-Pyrrolidine-2-carboxylic acid {3-[5-chloro-4-(4-cyclopropylcarbamoylbenzo[b]thiophen-2-yl)-pyrimidin-2-ylamino]-propyl}-amide

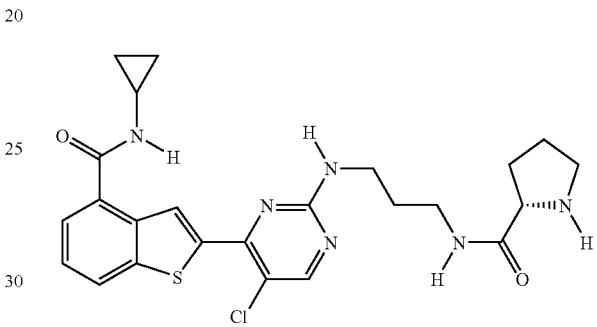

Using the method of (S)-pyrrolidine-3-carboxylic acid {3-[5-chloro-4-(4-cyclopropylcarbamoyl-benzo[b]thiophen-2-yl)-pyrimidin-2-ylamino]-propyl}-amide, the title compound is synthesized and isolated as the free base. ES+(m/z) 499 ($^{35}$Cl) and 501 ($^{37}$Cl) [M+H].

Using the method of 1-methylpiperidine-4-carboxylic acid-3-[5-chloro-4-(4-cyclopropylcarbamoylbenzo[b]thiophen-2-yl)-pyrimidin-2-ylamino]-propyl-amide, the following compounds are synthesized and isolated as the free base.

| Ex. | Compound | MS (ES+) m/z [M + H] |
|---|---|---|
| 216 | (S)-1-Methylpyrrolidine-3-carboxylic acid {3-[5-chloro-4-(4-cyclopropylcarbamoyl-benzo[b]thiophen-2-yl)-pyrimidin-2-ylamino]-propyl}-amide | 513 ($^{35}$Cl), 515 ($^{37}$Cl) |
| 217 | (S)-1-Methylpyrrolidine-2-carboxylic acid {3-[5-chloro-4-(4-cyclopropylcarbamoyl-benzo[b]thiophen-2-yl)-pyrimidin-2-ylamino]-propyl}-amide | 513 ($^{35}$Cl), 515 ($^{37}$Cl) |

EXAMPLE 218

2-{5-Chloro-2-[3-(4-methylpiperazin-1-yl)-propylamino]-pyrimidin-4-yl}-7-methoxybenzo[b]thiophene-4-carboxylic acid cyclopropylamide Diisopropylethylamine (1.10 mL, 5.78 mmol) and 1-(3-aminopropyl)-4-methylpiperazine (545 mg, 3.47 mmol) are added to a stirred suspension of 2-(2,5-dichloropyrimidin-4-yl)-7-methoxybenzo[b]thiophene-4-carboxylic acid cyclopropylamide (1.14 g, 2.89 mmol) in dry 1,4-dioxane (25 mL) at room temperature. The resultant mixture is heated in an oil bath at 97° C. for 2 days. At room temperature the mixture is filtered off and the solid is washed with MeOH to give the title compound as a solid (600 mg, 33% yield). The filtrate is concentrated and the residue is purified by HLB cartridge eluting with $NH_4HCO_3$ (pH=8) in $CH_3CN$ 1:0 to 0:1, and then by Stratta® column, eluting with dichloromethane in MeOH 12:1 to 4:1, to give an additional 339 mg of the title compound as a yellow solid. ES+(m/z) 515 ($^{35}Cl$) and 517 ($^{37}Cl$) [M+H].

EXAMPLE 219

2-{5-Chloro-2-[3-(4-methylpiperazin-1-yl)-propylamino]-pyrimidin-4-yl}-7-hydroxybenzo[b]thiophene-4-carboxylic acid cyclopropylamide To a solution of 2-{5-chloro-2-[3-(4-methylpiperazin-1-yl)-propylamino]-pyrimidin-4-yl}-7-methoxybenzo[b]thiophene-4-carboxylic acid cyclopropylamide (500 mg, 0.970 mmol) and ethanethiol (0.718 mL, 9.71 mmol) in dry DMF (10 mL) is added in one portion sodium hydride (388 mg, 9.71 mmol) at 0° C. The mixture is stirred for 5 minutes and heated to 110° C. in a preheated oil bath for 10 minutes. The mixture is cooled to room temperature and a solution of HCl (12%, 3.5 mL) is added. The mixture is diluted with water (100 mL) and concentrated. The residue is diluted with MeOH and filtered off. The filtrate is purified on silica gel, eluting with dichloromethane in MeOH 90:10 to 60:40, to give the title compound as a yellow solid (116 mg, 24% yield). ES+(m/z) 501 ($^{35}Cl$) and 503 ($^{37}Cl$) [M+H].

EXAMPLE 220

2-{5-Chloro-2-[3-(4-methylpiperazin-1-yl)-propylamino]-pyrimidin-4-yl}-benzo[b]thiophene-6-sulfonic acid amide To a suspension of [5-chloro-4-(6-triisopropylsilanylsulfanylbenzo[b]thiophen-2-yl)-pyrimidin-2-yl]-[3-(4-methylpiperazin-1-yl)-propyl]-amine (463 mg, 0.784 mmol) in acetonitrile (4 mL) is added potassium nitrate (198 mg, 1.96 mmol) followed by the dropwise addition of sulfuryl chloride (0.157 mL, 1.96 mmol). The mixture is stirred at room temperature for 1.5 hours. After filtration, the solid is suspended in acetone (5 mL) and a solution of ammonium hydroxide (0.926 mL, 15.7 mmol) is added dropwise at 0° C. After stirring at 0° C. for 1 hour, water (40 mL) is added and the mixture is extracted with EtOAc (3×50 mL). The organic layers are concentrated and the crude product is purified on silica gel, eluting with dichloromethane in MeOH 10:0 to 6:4. The solid obtained is washed with MeOH to give the title compound as a yellow solid (26 mg, 7% yield). ES+(m/z) 481 ($^{35}Cl$) and 483 ($^{37}Cl$) [M+H].

EXAMPLE 221

2-{5-[3-(4-Aminopiperazin-1-yl)-propylamino]-2-methylphenyl}-benzo[b]thiophene-6-sulfonic acid amide To a stirred suspension of 2-{5-methyl-2-[3-(4-methylpiperazin-1-yl)-propylamino]-pyrimidin-4-yl}-benzo[b]thiophene-6-sulfonic acid benzhydrylamide (315 mg, 0.502 mmol) in a solution of HCl (37%, 11.5 mL, 138 mmol) is heated at 80° C. for 21 hours. The mixture is cooled to room temperature and washed with dichloromethane (3×10 mL). The aqueous phase is concentrated and the crude product is purified by HPLC to give the title compound as a yellow solid (142 mg, 61% yield). ES+(m/z) 461 [M+H].

EXAMPLE 222

[5-Chloro-4-(6-methylsulfanyl)-benzo[b]thiophen-2-yl)-pyrimidin-2-yl]-[3-(4-methyl-piperazin-1-yl)-propyl]-amine A stirred mixture of 2,5-dichloro-4-(6-methylsulfanyl-benzo[b]thiophen-2-yl)-pyrimidine (0.14 g, 0.39 mmol), 1-(3-aminopropyl)-4-methylpiperazine (0.12 g, 0.78 mmol) and triethylamine (0.16 mL, 1.2 mmol) in n-butanol (2 mL) in a sealed tube is heated at 120° C. for 30 minutes. At room temperature the mixture is concentrated, the residue is purified by chromatography on silica gel, eluting with 2 M $NH_3$/MeOH in dichloromethane: 0-3%, to give the title product as a light yellow solid (0.11 g, 58% yield). ES+(m/z) 448 ($^{35}Cl$) and 450 ($^{37}Cl$) [M+H].

EXAMPLE 223

Racemic 2-[5-Chloro-2-(2-pyrrolidin-3-yl-ethylamino)-pyrimidin-4-yl]-benzo[b]thiophene-4-carboxylic acid cyclopropylamide A mixture of 2-(2,5-dichloropyrimidin-4-yl)-benzo[b]thiophene-4-carboxylic acid cyclopropylamide (0.10 g, 0.27 mmol), racemic 3-(2-aminoethyl)-pyrrolidine-1-carboxylic acid benzyl ester (0.14 g, 0.55 mmol) and triethylamine (0.11 mL, 0.81 mmol) in 1,4-dioxane (1.5 mL) in a sealed reaction vessel is stirred at 90° C. overnight. The reaction is cooled to room temperature and partitioned between ethyl acetate and saturated aqueous sodium bicarbonate solution, the organic layer is separated, dried over $Na_2SO_4$, filtered and concentrated. The crude solid is washed with ethyl acetate, dried under vacuum to provide 3-{2-[5-chloro-4-(4-cyclopropylcarbamoyl-benzo[b]thiophen-2-yl)-pyrimidin-2-ylamino]-ethyl}-pyrrolidine-1-carboxylic acid benzyl ester as a white solid (90 mg, 56% yield). A stirred solution of this intermediate (16 mg, 0.028 mmol) in TFA (0.5 mL) and water (0.1 mL) is heated in a sealed tube at 100° C. for 20 minutes. At room temperature the mixture is concentrated and the residue is dissolved in methanol, passed through a SCX column, washed with methanol and 2 M $NH_3$/methanol to give the crude product. It is further passed through a short pad of silica gel to afford the title compound as a solid (11 mg, 90% yield). ES+(m/z) 442 ($^{35}Cl$) and 444 ($^{37}Cl$) [M+H].

Using the method of 2-[2-(3-piperazin-1-ylpropylamino)-pyrimidin-4-yl]-benzo[b]thiophene-4-carboxylic acid cyclopropylamide tri-hydrochloride, the following compounds are synthesized and isolated as the HCl salt.

| Ex. | Compound | MS (ES+) m/z [M(free base) + H] |
|---|---|---|
| 224 | (4-Benzo[b]thiophen-2-yl-5-chloropyrimidin-2-yl)-(2-piperidin-4-yl-ethyl)-amine di-hydrochloride | 373 ($^{35}Cl$), 375 ($^{37}Cl$) |
| 225 | (4-Benzo[b]thiophen-2-yl-5-chloropyrimidin-2-yl)-(3-piperazin-1-ylpropyl)-amine tri-hydrochloride | 388 ($^{35}Cl$), 390 ($^{37}Cl$) |

EXAMPLE 226

(4-Benzo[b]thiophen-2-yl-5-bromopyrimidin-2-yl)-[2-(4-methylpiperazin-1-yl)-ethyl]-amine tri-hydrochloride Using the method of [4-(benzo[b]thiophen-2-yl)-pyrimidin-2-yl]-[3-(4-methylpiperazin-1-yl)-propyl]-amine tri-hydrochloride, the title compound is synthesized from 4-benzo[b]thiophen-2-yl-5-bromo-2-chloropyrimidine and isolated as a yellow solid. ES+(m/z) 432 ($^{79}$Br) and 434 ($^{81}$Br) [M(free base)+H].

EXAMPLE 227

2-[5-Chloro-2-(3-piperazin-1-yl-propylamino)-pyrimidin-4-yl]-benzo[b]thiophene-4-carboxylic acid amide tri-hydrochloride 4-(3-Aminopropyl)-piperidine-1-carboxylic acid tert-butyl ester (0.818 g, 3.36 mmol) is added to a stirred suspension of 2-(2,5-dichloropyrimidin-4-yl)-benzo[b]thiophene-4-carboxylic acid amide (0.436 g, 1.34 mmol) and diisopropylethylamine (0.70 mL, 4.0 mmol) in anhydrous 1,4-dioxane (8 mL) and dimethylacetamide (2 mL) at room temperature under nitrogen. The resultant mixture is heated in an oil bath at 95° C. for 7 hours. At room temperature the mixture is concentrated and chromatographed on silica gel, eluting with CH$_3$OH in dichloromethane: 0-6%, to give 4-{3-[4-(4-carbamoyl-benzo[b]thiophen-2-yl)-5-chloro-pyrimidin-2-ylamino]-propyl}-piperazine-1-carboxylic acid tert-butyl ester (0.403 g) as a solid.

This solid is dissolved in dichloromethane (40 mL) and MeOH (120 mL) with stirring, then a small stream of HCl gas is bubbled through the solution for 3 minutes. The flask is capped with a glass stopper and the yellow solution is allowed to stir for 16 hours. After concentration, the title compound is obtained as a yellow solid (0.402 g, 56% yield). ES+(m/z) 431 ($^{35}$Cl) and 433 ($^{37}$Cl) [M+H].

EXAMPLE 228

2-[5-Chloro-2-(2-piperidin-4-ylethylamino)-pyrimidin-4-yl]-benzo[b]thiophene-4-carboxylic acid amide A stirred mixture of 2-(2,5-dichloropyrimidin-4-yl)-benzo[b]thiophene-4-carboxylic acid amide (305 mg, 0.941 mmol), 4-(2-aminoethyl)-piperidine-1-carboxylic acid tert-butyl ester (430 mg, 1.88 mmol) and diisopropylethylamine (0.492 mL, 2.82 mmol) in 1,4-dioxane (6 mL) is heated at 97° C. under a nitrogen atmosphere for 7 hours. At room temperature the mixture is concentrated in vacuo to give a crude solid and it is subjected to a subsequent deprotection reaction. The solid is suspended in dichloromethane (12 mL), followed by the successive addition of triethylsilane (0.9 mL) and TFA (4 mL). The resultant yellow solution is stirred for 2 hours. After concentration and subsequent chromatography on silica gel, eluting with 2.0 M NH$_3$/MeOH in dichloromethane 3-10%, the fractions containing the desired product are collected and concentrated to give a solid. The solid is dissolved in MeOH (20 mL) and dichloromethane (20 mL) with stirring and the solution is treated in portions with 0.5 N LiOH (14 mL) to form a suspension. Methanol and dichloromethane are concentrated at 45° C. to give a yellow suspension. After filtration and drying the title compound is obtained as a yellow solid (0.200 g, 51% yield). ES+(m/z) 416 ($^{35}$Cl) and 418 ($^{37}$Cl) [M+H].

EXAMPLE 229

2-{5-Chloro-2-[2-(1-methylpiperidin-4-yl)-ethylamino]-pyrimidin-4-yl}-benzo[b]thiophene-4-carboxylic acid amide di-hydrochloride Aqueous formaldehyde (37.4% or 13.5 M, 0.134 mL, 1.80 mmol) is added to a stirred solution of 2-[5-chloro-2-(2-piperidin-4-ylethylamino)-pyrimidin-4-yl]-benzo[b]thiophene-4-carboxylic acid amide (150 mg, 0.361 mmol) in CH$_3$OH (15 mL) and dichloromethane (15 mL) at room temperature to form a light suspension. The mixture is allowed to stir for 90 minutes. The mixture is cooled to 0° C. before it is treated with powdered sodium borohydride (68.1 mg, 1.80 mmol). The mixture is stirred at 0° C. for 1 hour, then allowed to slowly warm up to room temperature to form a clear solution. After concentration, the crude product is subject to chromatographic purification on silica gel, eluting with 2 M NH$_3$/CH$_3$OH in dichloromethane 4-12%, to give the desired methylated product as a yellowish solid. The free base is dissolved in CH$_3$OH (20 mL) and dichloromethane (20 mL) then treated with 12 N HCl (0.30 mL) to form a yellow solution. After concentration and vacuum drying at 60° C., the title compound is obtained as a yellow solid (174 mg, 95% yield). ES+(m/z) 430 ($^{35}$Cl) and 432 ($^{37}$Cl) [M(free base)+H].

EXAMPLE 230

2-[5-Methyl-2-(3-piperidin-4-ylpropylamino)-pyrimidin-4-yl]-benzo[b]thiophene-4-carboxylic acid amide (A). Preparation of 2-(2-chloro-5-methylpyrimidin-4-yl)-benzo[b]thiophene-4-carboxylic acid [bis-(4-methoxyphenyl)-methyl]-amide Diisopropylethylamine (1.80 mL, 10.3 mmol) is added to a stirred suspension of 2-(2-chloro-5-methylpyrimidin-4-yl)-benzo[b]thiophene-4-carboxylic acid (3.00 g, 9.84 mmol) in anhydrous dichloromethane (100 mL) at 0° C. under nitrogen to form a solution, then followed by the successive addition of C,C-bis-(4-methoxyphenyl)-methylamine (2.51 g, 10.3 mmol) and powdered 1H-benzotriazol-1-yloxytris(dimethylamino)phosphonium hexafluorophosphate (4.56 g, 10.3 mmol). The resultant mixture is allowed to stir at 0° C. for 1 hour, then at room temperature for 3 hours. Diethyl ether (50 mL) is added in small portions to the mixture, the mixture is stirred for another 10 minutes before filtration. After vacuum drying at 35° C., the crude title compound (5.19 g) is obtained as a tan solid. It is used without further purification.

(B). Preparation of 2-[5-methyl-2-(3-piperidin-4-ylpropylamino)-pyrimidin-4-yl]-benzo[b]thiophene-4-carboxylic acid amide A stirred mixture of 2-(2-chloro-5-methylpyrimidin-4-yl)-benzo[b]thiophene-4-carboxylic acid [bis-(4-methoxyphenyl)-methyl]-amide (1.14 g, 2.15 mmol), 4-(3-aminopropyl)-piperidine-1-carboxylic acid tert-butyl ester (1.04 g, 4.30 mmol) and diisopropylethylamine (1.12 mL, 6.45 mmol) in 1,4-dioxane (10 mL) is heated at 97° C. under a nitrogen atmosphere for 3 days. After concentration and subsequent chromatography on silica gel, eluting with MeOH in dichloromethane 0-2%, the desired product is obtained as a solid. The solid is suspended in dichloromethane (20 mL), followed by the successive addition of triethylsilane (1.5 mL) and TFA (5 mL). The resultant yellow solution is stirred for 2 hours. After concentration the solid is dissolved with stirring in MeOH (30 mL) and dichloromethane (30 mL) and the solution is treated in portions with 1.0 N LiOH (15 mL) to form a suspension. The suspension is concentrated at 45° C. under atmospheric pressure for 30 minutes, then methanol and dichloromethane are evaporated off in vacuo. The suspension is filtered and the yellow solid is dried under vacuum at 45° C. to provide the title compound (0.890 g, 100% yield). ES+(m/z) 410 [M+H].

EXAMPLE 231

2-{5-Methyl-2-[3-(1-methylpiperidin-4-yl)-propylamino]-pyrimidin-4-yl}-benzo[b]thiophene-4-carboxylic acid amide di-hydrochloride Using the method of 2-{5-chloro-2-[2-(1-methylpiperidin-4-yl)-ethylamino]-pyrimidin-4-yl}-benzo[b]thiophene-4-carboxylic acid amide di-hydrochloride, the title compound is synthesized from 2-[5-methyl-2-(3-piperidin-4-ylpropylamino)-pyrimidin-4-yl]-benzo[b]thiophene-4-carboxylic acid amide and isolated as a yellow solid. ES+(m/z) 424 [M(free base)+H].

EXAMPLE 232

2-{5-Bromo-2-[3-(4-methylpiperazin-1-yl)-propylamino]-pyrimidin-4-yl}-benzo[b]thiophene-4-carboxylic acid amide tri-hydrochloride A stirred mixture of 2-(5-bromo-2-chloropyrimidin-4-yl)-benzo[b]thiophene-4-carboxylic acid [bis-(4-methoxyphenyl)-methyl]-amide (1.02 g, 1.71 mmol), 3-(4-methyl-piperazin-1-yl)-propylamine (0.809 g, 5.14 mmol) in 1,4-dioxane (10 mL) is heated at 97° C. under nitrogen atmosphere for 7 hours. After concentration and subsequent chromatography on silica gel, eluting with 2 M $NH_3$/MeOH in dichloromethane 0-8%, the intermediate is obtained as a solid (1.05 g). Then the solid (380 mg, 0.531 mmol) is suspended in dichloromethane (20 mL), followed by the successive addition of triethylsilane (0.51 mL) and TFA (4 mL), the resultant yellow solution is stirred for 7 hours. After concentration and subsequent chromatography on silica gel, eluting with 2 M $NH_3$/MeOH in dichloromethane 0-12%, the fractions containing the desired product are collected and concentrated to give a solid. The solid is dissolved with stirring in MeOH (40 mL) and dichloromethane (40 mL) and the solution is treated with 0.5 N LiOH (8 mL) to form a suspension. After evaporation of methanol and dichloromethane, the aqueous suspension is filtered to give the free base of the title compound as a yellow solid. The solid is dissolved in MeOH (40 mL) and dichloromethane (40 mL), treated with 12 N HCl (1.0 mL) then concentrated to provide the title compound (317 mg, 99% yield). ES+(m/z) 489 ($^{79}$Br) and 491 ($^{81}$Br) [M(free base)+H].

EXAMPLE 233

(R)-2-{5-Chloro-2-[3-(2-methylpiperazin-1-yl)-propylamino]-pyrimidin-4-yl}-benzo[b]thiophene-4-carboxylic acid methylamide A stirred mixture of 2-(2,5-dichloropyrimidin-4-yl)-benzo[b]thiophene-4-carboxylic acid methylamide (0.30 g, 0.89 mmol), (R)-4-(3-aminopropyl)-3-methylpiperazine-1-carboxylic acid tert-butyl ester (0.57 g, 2.2 mmol) and diisopropylethylamine (0.29 g, 2.2 mmol) in 1,4-dioxane (5 mL) is heated at 90° C. under a nitrogen atmosphere for 14 hours. After concentration and subsequent chromatography on silica gel, eluting with 2 M $NH_3$/MeOH in dichloromethane 0-8%, the intermediate is obtained as a solid. The solid is suspended in dichloromethane (3 mL), followed by the successive addition of triethylsilane (0.50 mL) and TFA (3 mL). The resultant yellow solution is stirred for 7 hours. After concentration a wet solid is obtained. The solid is treated with 2 N LiOH, with sonication, until pH reaches 12. The mixture is filtered, the solid is dried before it is subject to chromatography on silica gel, eluting with 2 M $NH_3$/MeOH in dichloromethane 0-20%, to give the title compound as a yellow solid (190 mg, 46% yield). ES+(m/z) 459 ($^{35}$Cl) and 461 ($^{37}$Cl) [M+H].

Using the method of (R)-2-{5-chloro-2-[3-(2-methylpiperazin-1-yl)-propylamino]-pyrimidin-4-yl}-benzo[b]thiophene-4-carboxylic acid methylamide, the following compounds are synthesized from the corresponding 2-(2-chloropyrimidin-4-yl)-benzo[b]thiophene-4-carboxylic acid amide and (R)-4-(3-aminopropyl)-3-methylpiperazine-1-carboxylic acid tert-butyl ester and isolated either as the free base or hydrochloride acid salt by treating the free base with 12 N HCl (10 equivalents) as described using the method of 2-{5-chloro-2-[2-(1-methylpiperidin-4-yl)-ethylamino]-pyrimidin-4-yl}-benzo[b]thiophene-4-carboxylic acid amide di-hydrochloride.

| Ex. | Compound | MS (ES+) m/z [M(free base) + H] |
|---|---|---|
| 234 | (R)-2-{5-Methyl-2-[3-(2-methyl-piperazin-1-yl)-propylamino]-pyrimidin-4-yl}-benzo[b]thiophene-4-carboxylic acid methylamide | 439 |
| 235 | (R)-2-{2-[3-(2-Methyl-piperazin-1-yl)-propylamino]-pyrimidin-4-yl}-benzo[b]thiophene-4-carboxylic acid cyclopropylamide | 451 |
| 236 | (R)-2-{5-Chloro-2-[3-(2-methyl-piperazin-1-yl)-propylamino]-pyrimidin-4-yl}-benzo[b]thiophene-4-carboxylic acid cyclopropylamide tri-hydrochloride | 485 ($^{35}$Cl), 487 ($^{37}$Cl) |
| 237 | (R)-2-{5-Methyl-2-[3-(2-methyl-piperazin-1-yl)-propylamino]-pyrimidin-4-yl}-benzo[b]thiophene-4-carboxylic acid cyclopropylamide tri-hydrochloride | 465 |

EXAMPLE 238

(R)-2-{5-Chloro-2-[3-(2,4-dimethyl-piperazin-1-yl)-propylamino]-pyrimidin-4-yl}-benzo[b]thiophene-4-carboxylic acid methylamide tri-hydrochloride Using the method of 2-{5-chloro-2-[2-(1-methylpiperidin-4-yl)-ethylamino]-pyrimidin-4-yl}-benzo[b]thiophene-4-carboxylic acid amide di-hydrochloride, the title compound is synthesized from (R)-2-{5-chloro-2-[3-(2-methylpiperazin-1-yl)-propylamino]-pyrimidin-4-yl}-benzo[b]

thiophene-4-carboxylic acid methylamide and isolated as a yellow solid. ES+(m/z) 473 ($^{35}$Cl) and 475 ($^{37}$Cl) [M+H].

Using the method of 2-{5-chloro-2-[2-(1-methylpiperidin-4-yl)-ethylamino]-pyrimidin-4-yl}-benzo[b]thiophene-4-carboxylic acid amide di-hydrochloride, the following compounds are synthesized from the corresponding (R)-2-{2-[3-(2-methylpiperazin-1-yl)-propylamino]-pyrimidin-4-yl}-benzo[b]thiophene-4-carboxylic acid amide and isolated as a yellow solid.

| Ex. | Compound | MS (ES+) m/z [M(free base) + H] |
|---|---|---|
| 239 | (R)-2-{2-[3-(2,4-Dimethylpiperazin-1-yl)-propylamino]-5-methylpyrimidin-4-yl}-benzo[b]thiophene-4-carboxylic acid methylamide tri-hydrochloride | 453 |
| 240 | (R)-2-{2-[3-(2,4-Dimethylpiperazin-1-yl)-propylamino]-pyrimidin-4-yl}-benzo[b]thiophene-4-carboxylic acid cyclopropylamide tri-hydrochloride | 465 |
| 241 | (R)-2-{5-Chloro-2-[3-(2,4-dimethylpiperazin-1-yl)-propylamino]-pyrimidin-4-yl}-benzo[b]thiophene-4-carboxylic acid cyclopropylamide tri-hydrochloride | 499 ($^{35}$Cl), 501 ($^{37}$Cl) |
| 242 | (R)-2-{2-[3-(2,4-Dimethylpiperazin-1-yl)-propylamino]-5-methylpyrimidin-4-yl}-benzo[b]thiophene-4-carboxylic acid cyclopropylamide tri-hydrochloride | 479 |

EXAMPLE 243

(R)-2-{5-Chloro-2-[2-(2-methylpiperazin-1-yl)-ethylamino]-pyrimidin-4-yl}-benzo[b]thiophene-4-carboxylic acid cyclopropylamide Using the method of (R)-2-{5-chloro-2-[3-(2-methylpiperazin-1-yl)-propylamino]-pyrimidin-4-yl}-benzo[b]thiophene-4-carboxylic acid methylamide, the title compound is synthesized from 2-(2,5-dichloropyrimidin-4-yl)-benzo[b]thiophene-4-carboxylic acid cyclopropylamide and (R)-4-(2-aminoethyl)-3-methylpiperazine-1-carboxylic acid tert-butyl ester and isolated as a yellow solid. ES+(m/z) 471 ($^{35}$Cl) and 473 ($^{37}$Cl) [M+H].

EXAMPLE 244

(R)-2-{5-Methyl-2-[2-(2-methylpiperazin-1-yl)-ethylamino]-pyrimidin-4-yl}-benzo[b]thiophene-4-carboxylic acid cyclopropylamide Using the method of (R)-2-{5-chloro-2-[2-(2-methylpiperazin-1-yl)-ethylamino]-pyrimidin-4-yl}-benzo[b]thiophene-4-carboxylic acid cyclopropylamide, the title compound is synthesized from 2-(2-chloro-5-methylpyrimidin-4-yl)-benzo[b]thiophene-4-carboxylic acid cyclopropylamide and (R)-4-(2-aminoethyl)-3-methylpiperazine-1-carboxylic acid tert-butyl ester and isolated as a yellow solid. ES+(m/z) 451 [M+H].

EXAMPLE 245

(R)-2-{5-Chloro-2-[2-(2,4-dimethylpiperazin-1-yl)-ethylamino]-pyrimidin-4-yl}-benzo[b]thiophene-4-carboxylic acid cyclopropylamide tri-hydrochloride Using the method of 2-{5-chloro-2-[2-(1-methylpiperidin-4-yl)-ethylamino]-pyrimidin-4-yl}-benzo[b]thiophene-4-carboxylic acid amide di-hydrochloride, the title compound is synthesized from (R)-2-{5-chloro-2-[2-(2-methyl-piperazin-1-yl)-ethylamino]-pyrimidin-4-yl}-benzo[b]thiophene-4-carboxylic acid cyclopropylamide and isolated as a yellow solid. ES+(m/z) 485 ($^{35}$Cl) and 487 ($^{37}$Cl) [M(free base)+H].

EXAMPLE 246

(R)-2-{2-[2-(2,4-Dimethylpiperazin-1-yl)-ethylamino]-5-methylpyrimidin-4-yl}-benzo[b]thiophene-4-carboxylic acid cyclopropylamide tri-hydrochloride Using the method of 2-{5-chloro-2-[2-(1-methylpiperidin-4-yl)-ethylamino]-pyrimidin-4-yl}-benzo[b]thiophene-4-carboxylic acid amide di-hydrochloride, the title compound is synthesized from (R)-2-{5-methyl-2-[2-(2-methylpiperazin-1-yl)-ethylamino]-pyrimidin-4-yl}-benzo[b]thiophene-4-carboxylic acid cyclopropylamide and isolated as a yellow solid. ES+(m/z) 465 [M(free base)+H].

EXAMPLE 247

(S)-2-{5-Chloro-2-[3-(2-methylpiperazin-1-yl)-propylamino]-pyrimidin-4-yl}-benzo[b]thiophene-4-carboxylic acid cyclopropylamide tri-hydrochloride Using the method of (R)-2-{5-chloro-2-[3-(2-methylpiperazin-1-yl)-propylamino]-pyrimidin-4-yl}-benzo[b]thiophene-4-carboxylic acid methylamide, free base of the title compound is synthesized from 2-(2,5-dichloropyrimidin-4-yl)-benzo[b]thiophene-4-carboxylic acid cyclopropylamide and (S)-4-(3-aminopropyl)-3-methylpiperazine-1-carboxylic acid tert-butyl ester. After treating the free base with 12 N HCl (10 equivalents) as described in 2-{5-chloro-2-[2-(1-methylpiperidin-4-yl)-ethylamino]-pyrimidin-4-yl}-benzo[b]thiophene-4-carboxylic acid amide di-hydrochloride, the title compound is isolated as a yellow solid. ES+(m/z) 485 ($^{35}$Cl) and 487 ($^{37}$Cl) [M(free base)+H].

EXAMPLE 248

(S)-2-{5-Methyl-2-[3-(2-methylpiperazin-1-yl)-propylamino]-pyrimidin-4-yl}-benzo[b]thiophene-4-carboxylic acid methylamide Using the method of (R)-2-{5-chloro-2-[3-(2-methylpiperazin-1-yl)-propylamino]-pyrimidin-4-yl}-benzo[b]thiophene-4-carboxylic acid methylamide, the title compound is synthesized from 2-(2-chloro-5-methylpyrimidin-4-yl)-benzo[b]thiophene-4-carboxylic acid methylamide and (S)-4-(3-aminopropyl)-3-methylpiperazine-1-carboxylic acid tert-butyl ester and isolated as a yellow solid. ES+(m/z) 439 [M+H].

EXAMPLE 249

(S)-2-{5-Methyl-2-[3-(2-methylpiperazin-1-yl)-propylamino]-pyrimidin-4-yl}-benzo[b]thiophene-4-carboxylic acid cyclopropylamide Using the method of (R)-2-{5-chloro-2-[3-(2-methylpiperazin-1-yl)-propylamino]-pyrimidin-4-yl}-benzo[b]thiophene-4-carboxylic acid methylamide, the title compound is synthesized from 2-(2-chloro-5-methyl-pyrimidin-4-yl)-benzo[b]thiophene-4-carboxylic acid cyclopropylamide and (S)-4-(3-aminopropyl)-3-methylpiperazine-1-carboxylic acid tert-butyl ester and isolated as a yellow solid. ES+(m/z) 465 [M+H].

EXAMPLE 250

(S)-2-{5-Chloro-2-[3-(2,4-dimethylpiperazin-1-yl)-propylamino]-pyrimidin-4-yl}-benzo[b]thiophene-4-carboxylic acid cyclopropylamide tri-hydrochloride Using the method of 2-{5-chloro-2-[2-(1-methylpiperidin-4-yl)-ethylamino]-pyrimidin-4-yl}-benzo[b]thiophene-4-carboxylic acid amide di-hydrochloride, the title compound is synthesized from (S)-2-{5-chloro-2-[3-(2-methylpiperazin-1-yl)-propylamino]-pyrimidin-4-yl}-benzo[b]thiophene-4-carboxylic acid cyclopropylamide and isolated as a yellow solid. ES+(m/z) 499 ($^{35}$Cl) and 501 ($^{37}$Cl) [M(free base)+H].

EXAMPLE 251

(S)-2-{2-[3-(2,4-Dimethylpiperazin-1-yl)-propylamino]-5-methylpyrimidin-4-yl}-benzo[b]thiophene-4-carboxylic acid cyclopropylamide tri-hydrochloride Using the method of 2-{5-chloro-2-[2-(1-methylpiperidin-4-yl)-ethylamino]-pyrimidin-4-yl}-benzo[b]thiophene-4-carboxylic acid amide di-hydrochloride, the title compound is synthesized from (S)-2{5-methyl-2-[3-(2-methylpiperazin-1-yl)-propylamino]-pyrimidin-4-yl}-benzo[b]thiophene-4-carboxylic acid cyclopropylamide and isolated as a yellow solid. ES+(m/z) 479 [M(free base)+H].

EXAMPLE 252

(S)-2-{5-Methyl-2-[3-(3-methylpiperazin-1-yl)-propylamino]-pyrimidin-4-yl}-benzo[b]thiophene-4-carboxylic acid methylamide Using the method of (R)-2-{5-chloro-2-[3-(2-methylpiperazin-1-yl)-propylamino]-pyrimidin-4-yl}-benzo[b]thiophene-4-carboxylic acid methylamide, the title compound is synthesized from 2-(2-chloro-5-methylpyrimidin-4-yl)-benzo[b]thiophene-4-carboxylic acid methylamide and (S)-4-(3-aminopropyl)-2-methylpiperazine-1-carboxylic acid tert-butyl ester and isolated as a yellow solid. ES+(m/z) 439 [M+H].

Using the method of (R)-2-{5-chloro-2-[3-(2-methylpiperazin-1-yl)-propylamino]-pyrimidin-4-yl}-benzo[b]thiophene-4-carboxylic acid methylamide, the following compounds are synthesized from the corresponding 2-(2-chloropyrimidin-4-yl)-benzo[b]thiophene-4-carboxylic acid amide and (S)-2-methylpiperazine-1-carboxylic acid tert-butyl ester and isolated as a solid.

| Ex. | Compound | MS (ES+) m/z [M + H] |
|---|---|---|
| 253 | 2-{5-Chloro-2-[3-((S)-3-methylpiperazin-1-yl)-propylamino]-pyrimidin-4-yl}-benzo[b]thiophene-4-carboxylic acid methylamide | 459 ($^{35}$Cl), 461 ($^{37}$Cl) |
| 254 | 2-{5-Methyl-2-[3-((S)-3-methylpiperazin-1-yl)-propylamino]-pyrimidin-4-yl}-benzo[b]thiophene-4-carboxylic acid cyclopropylamide | 465 |
| 255 | 2-{5-Chloro-2-[3-((S)-3-methylpiperazin-1-yl)-propylamino]-pyrimidin-4-yl}-benzo[b]thiophene-4-carboxylic acid cyclopropylamide | 485 ($^{35}$Cl), 487 ($^{37}$Cl) |

EXAMPLE 256

(S)-2-{2-[3-(3,4-Dimethylpiperazin-1-yl)-propylamino]-5-methylpyrimidin-4-yl}-benzo[b]thiophene-4-carboxylic acid methylamide tri-hydrochloride Using the method of 2-{5-chloro-2-[2-(1-methylpiperidin-4-yl)-ethylamino]-pyrimidin-4-yl}-benzo[b]thiophene-4-carboxylic acid amide di-hydrochloride, the title compound is synthesized from (S)-2-{5-methyl-2-[3-(3-methylpiperazin-1-yl)-propylamino]-pyrimidin-4-yl}-benzo[b]thiophene-4-carboxylic acid methylamide and isolated as a yellow solid. ES+(m/z) 453 [M(free base)+H].

Using the method of 2-{5-chloro-2-[2-(1-methylpiperidin-4-yl)-ethylamino]-pyrimidin-4-yl}-benzo[b]thiophene-4-carboxylic acid amide di-hydrochloride, the following compounds are synthesized from the corresponding (S)-2-{2-[3-(3-methylpiperazin-1-yl)-propylamino]-pyrimidin-4-yl}-benzo[b]thiophene-4-carboxylic acid amide and isolated as a solid.

| Ex. | Compound | MS (ES+) m/z [M(free base) + H] |
|---|---|---|
| 257 | (S)-2-{5-Chloro-2-[3-(3,4-dimethylpiperazin-1-yl)-propylamino]-pyrimidin-4-yl}-benzo[b]thiophene-4-carboxylic acid methylamide tri-hydrochloride | 473 ($^{35}$Cl), 475 ($^{37}$Cl) |
| 258 | (S)-2-{2-[3-(3,4-Dimethylpiperazin-1-yl)-propylamino]-5-methylpyrimidin-4-yl}-benzo[b]thiophene-4-carboxylic acid cyclopropylamide tri-hydrochloride | 479 |
| 259 | (S)-2-{5-Chloro-2-[3-(3,4-dimethylpiperazin-1-yl)-propylamino]-pyrimidin-4-yl}-benzo[b]thiophene-4-carboxylic acid cyclopropylamide tri-hydrochloride | 499 ($^{35}$Cl), 501 ($^{37}$Cl) |

EXAMPLE 260

2-{5-Chloro-2-[3-(4-ethylpiperidin-4-yl)-propylamino]-pyrimidin-4-yl}-benzo[b]thiophene-4-carboxylic acid cyclopropylamide di-hydrochloride

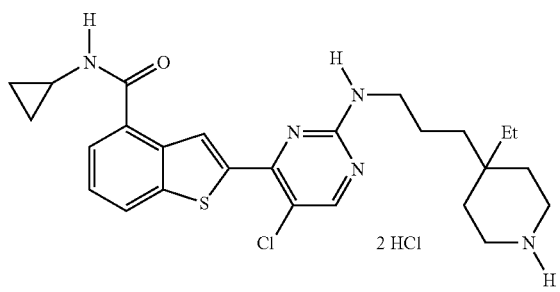

A stirred mixture of 2-(2,5-dichloropyrimidin-4-yl)-benzo[b]thiophene-4-carboxylic acid cyclopropylamide (180 mg, 0.494 mmol), 4-(3-aminopropyl)-4-ethylpiperidine-1-carboxylic acid tert-butyl ester (200 mg, 0.741 mmol) and diisopropylethylamine (128 mg, 0.988 mmol) in 1,4-dioxane (3 mL) is heated at 90° C. under nitrogen for 18 hours. At room temperature the mixture is concentrated and the crude product is chromatographed on silica gel, eluting with 3% 2 M NH$_3$/MeOH in dichloromethane, to give 197 mg of 4-{3-[5-chloro-4-(4-cyclopropylcarbamoylbenzo[b]thiophen-2-yl)-pyrimidin-2-ylamino]-propyl}-4-ethylpiperidine-1-carboxylic acid tert-butyl ester. The intermediate is then subject to deprotection by dissolving the material (197 mg, 0.329 mmol) in MeOH (25 mL) and dichloromethane (12 mL) and bubbling anhydrous hydrogen chloride gas for 5 minutes. The hot, yellow solution is allowed to sit at room temperature for 2 hours, then concentrated to give the title compound as a yellow solid (184 mg, 98% yield). ES+(m/z) 498 ($^{35}$Cl) and 500 ($^{37}$Cl) [M(free base)+H].

EXAMPLE 261

2-{5-Chloro-2-[3-(4-ethylpiperidin-4-yl)-propylamino]-pyrimidin-4-yl}-benzo[b]thiophene-4-carboxylic acid methylamide di-hydrochloride Using the method of 2-{5-chloro-2-[3-(4-ethylpiperidin-4-yl)-propylamino]-pyrimidin-4-yl}-benzo[b]thiophene-4-carboxylic acid cyclopropylamide di-hydrochloride, the title compound is synthesized from 2-(2,5-dichloropyrimidin-4-yl)-benzo[b]thiophene-4-carboxylic acid methylamide and 4-(3-aminopropyl)-4-ethylpiperidine-1-carboxylic acid tert-butyl ester and isolated as a solid. ES+(m/z) 472 ($^{35}$Cl) and 474 ($^{37}$Cl) [M(free base)+H].

EXAMPLE 262

2-{5-Chloro-2-[3-(4-ethyl-1-methylpiperidin-4-yl)-propylamino]-pyrimidin-4-yl}-benzo[b]thiophene-4-carboxylic acid cyclopropylamide di-hydrochloride A stirred solution of 2-{5-chloro-2-[3-(4-ethylpiperidin-4-yl)-propylamino]-pyrimidin-4-yl}-benzo[b]thiophene-4-carboxylic acid cyclopropylamide di-hydrochloride (156 mg, 0.274 mmol) in CH$_3$OH (8 mL) and dichloromethane (8 mL) is treated with 5 N NaOH (0.110 mL) at room temperature, followed by the addition of aqueous formaldehyde (37.4% or 13.5 M, 0.102 mL, 1.37 mmol). The mixture is stirred at room temperature for 90 minutes. The mixture is cooled to 0° C. then treated with powdered sodium borohydride (52 mg, 1.4 mmol). At 0° C. the mixture is stirred for 1 hour before it is allowed to slowly warm up to room temperature over another hour. After concentration, the crude product is subject to chromatographic purification on silica gel, eluting with 2 M NH$_3$/CH$_3$OH in dichloromethane 4-12%, to give the free base as a yellow solid (129 mg, 92% yield). The free base (104 mg, 0.203 mmol) is dissolved in CH$_3$OH (10 mL) and dichloromethane (10 mL) then treated with 12 N HCl (0.20 mL) to form a yellow solution. After concentration and vacuum drying at 60° C., the title compound is obtained as a yellow solid (118 mg, 99% yield). ES+(m/z) 512 ($^{35}$Cl) and 514 ($^{37}$Cl) [M(free base)+H].

EXAMPLE 263

2-{5-Chloro-2-[3-(4-ethyl-1-methylpiperidin-4-yl)-propylamino]-pyrimidin-4-yl}-benzo[b]thiophene-4-carboxylic acid methylamide di-hydrochloride Using the method of 2-{5-chloro-2-[3-(4-ethyl-1-methylpiperidin-4-yl)-propylamino]-pyrimidin-4-yl}-benzo[b]thiophene-4-carboxylic acid cyclopropylamide di-hydrochloride, the title compound is synthesized from 2-{5-chloro-2-[3-(4-ethylpiperidin-4-yl)-propylamino]-pyrimidin-4-yl}-benzo[b]thiophene-4-carboxylic acid methylamide di-hydrochloride and isolated as a yellow solid. ES+(m/z) 486 ($^{35}$Cl) and 488 ($^{37}$Cl) [M(free base)+H].

EXAMPLE 264

Racemic 2-[5-Methyl-2-(3-piperidin-3-ylpropylamino)-pyrimidin-4-yl]-benzo[b]thiophene-4-carboxylic acid cyclopropylamide A stirred mixture of 2-(2-chloro-5-methylpyrimidin-4-yl)-benzo[b]thiophene-4-carboxylic acid cyclopropylamide (0.50 g, 1.5 mmol), racemic 3-(3-aminopropyl)-piperidine-1-carboxylic acid tert-butyl ester (0.88 g, 3.6 mmol) and diisopropylethylamine (0.47 g, 3.6 mmol) in 1,4-dioxane (7 mL) is heated at 90° C. under a nitrogen atmosphere for 48 hours. After concentration and subsequent chromatography on silica gel, eluting with 2 M NH$_3$/MeOH in dichloromethane 1-10%, the intermediate is obtained as a solid. The solid is suspended in dichloromethane (3 mL), followed by the successive addition of triethylsilane (0.50 mL) and TFA (3 mL), the resultant yellow solution is stirred for 16 hours. After concentration a wet solid is obtained. It is treated with 2 N LiOH, with sonication, until pH reaches 12. The mixture is filtered and the solid is dried before it is subjected to chromatography on silica gel, eluting with 2 M NH$_3$/MeOH in dichloromethane 10-20%, to give the title compound as a yellow solid (160 mg, 25% yield). ES+(m/z) 450 [M+H].

EXAMPLE 265

Racemic 2-{5-Methyl-2-[3-(1-methylpiperidin-3-yl)-propylamino]-pyrimidin-4-yl}-benzo[b]thiophene-4-carboxylic acid cyclopropylamide di-hydrochloride Using the method of 2-{5-chloro-2-[2-(1-methylpiperidin-4-yl)-ethylamino]-pyrimidin-4-yl}-benzo[b]thiophene-4-carboxylic acid amide di-hydrochloride, the title compound is synthesized from racemic 2-[5-methyl-2-(3-piperidin-3-- yl-propylamino)-pyrimidin-4-yl]-benzo[b]thiophene-4-carboxylic acid cyclopropylamide and isolated as a yellow solid. ES+(m/z) 464 [M(free base)+H].

EXAMPLE 266

Racemic 2-{5-Chloro-2-[3-(2-isopropylpiperazin-1-yl)-propylamino]-pyrimidin-4-yl}-benzo[b]thiophene-4-carboxylic acid cyclopropylamide Using the method of racemic 2-[5-methyl-2-(3-piperidin-3-ylpropylamino)-pyrimidin-4-yl]-benzo[b]thiophene-4-carboxylic acid cyclopropylamide, the title compound is synthesized from 2-(2,5-dichloropyrimidin-4-yl)-benzo[b]thiophene-4-carboxylic acid cyclopropylamide and racemic 4-(3-aminopropyl)-3-isopropylpiperazine-1-carboxylic acid tert-butyl ester and isolated as a solid. ES+(m/z) 513 ($^{35}$Cl) and 515 ($^{37}$Cl) [M+H].

EXAMPLE 267

Racemic 2-{5-Chloro-2-[3-(2-isopropyl-4-methylpiperazin-1-yl)-propylamino]-pyrimidin-4-yl}-benzo[b]thiophene-4-carboxylic acid cyclopropylamide tri-hydrochloride Using the method of 2-{5-chloro-2-[2-(1-methylpiperidin-4-yl)-ethylamino]-pyrimidin-4-yl}-benzo[b]thiophene-4-carboxylic acid amide di-hydrochloride, the title compound is synthesized from racemic 2-{5-chloro-2-[3-(2-isopropyl-piperazin-1-yl)-propylamino]-pyrimidin-4-yl}-benzo[b]thiophene-4-carboxylic acid cyclopropylamide and isolated as a yellow solid. ES+(m/z) 527 ($^{35}$Cl) and 529 ($^{37}$Cl) [M(free base)+H].

EXAMPLE 268

2-[5-Chloro-2-(2-methylaminoethylamino)-pyrimidin-4-yl]-benzo[b]thiophene-4-carboxylic acid cyclopropylamide di-hydrochloride A stirred mixture of 2-(2,5-dichloropyrimidin-4-yl)-benzo[b]thiophene-4-carboxylic acid cyclopropylamide (406 mg, 1.12 mmol), (2-aminoethyl)-methylcarbamic acid tert-butyl ester (486 mg, 2.79 mmol) and diisopropylethylamine (432 mg, 3.34 mmol) in 1,4-dioxane (4 mL) is heated at 95° C. under nitrogen for 18 hours. At room temperature the mixture is concentrated and the crude product is chromatographed on silica gel, eluting with EtOAc in dichloromethane 0-35%, to give {2-[5-chloro-4-(4-cyclopropylcarbamoyl-benzo[b]thiophen-2-yl)-pyrimidin-2-ylamino]-ethyl}-methylcarbamic acid tert-butyl ester as a foam (418 mg, 75% yield). The intermediate is then subjected to deprotection by dissolving this material (415 mg, 0.827 mmol) in MeOH (12 mL) and bubbling anhydrous HCl gas for 5 minutes. The hot, yellow solution is allowed to sit at room temperature for 2 hours, then concentrated to give the title compound as a yellow solid (352 mg, 90% yield). ES+(m/z) 402 ($^{35}$Cl) and 404 ($^{37}$Cl) [M(free base)+H].

EXAMPLE 269

2-{5-Chloro-2-[3-(4-methylpiperazin-1-yl)-propylamino]-pyrimidin-4-yl}-benzo[b]thiophene-4-carboxylic acid hydrazide A mixture of 2-{5-chloro-2-[3-(4-methylpiperazin-1-yl)-propylamino]-pyrimidin-4-yl}-benzo[b]thiophene-4-carboxylic acid tri-hydrochloride (425 mg, 0.960 mmol), tert-butylcarbazate (398 mg, 3.01 mmol), diisopropylethylamine (0.500 mL, 2.87 mmol), (benzotriazol-1-yloxy)tris(dimethylamino)phosphonium hexafluorophosphate (510 mg, 1.15 mmol), and lithium chloride (498 mg, 11.7 mmol) in DMF (6 mL) is heated at 50° C. for 20 hours. After cooling to room temperature, the solvent is removed and the residue is subjected to chromatography on silica gel, eluting with 2.0 M NH$_3$/MeOH) in dichloromethane 0-10%, to give N'-(2-{5-chloro-2-[3-(4-methylpiperazin-1-yl)-propylamino]-pyrimidin-4-yl}-benzo[b]thiophene-4-carbonyl)-hydrazinecarboxylic acid tert-butyl ester (441 mg, 82% yield).

A stirred solution of this intermediate (441 mg, 0.790 mmol) in THF (8 mL) is treated with 1.0 N HCl (5 mL) then heated at 70° C. The solvent is evaporated and the residue is put through a Varian Megabond SCX column that is pre-eluted with methanol. The product is eluted from the column with 20% (2.0 M NH$_3$/MeOH)/80% EtOAc solution. After concentration, the residue is dissolved in DMSO at 100 mg/mL concentration and injected onto a Xxtera C18 preparative reverse phase column, eluting with 10-50% acetonitrile/water with ammonium bicarbonate at pH=10. The fractions containing product are lyophilized to give the title compound as a solid (13.9 mg, 4% yield). ES+(m/z) 460 ($^{35}$Cl) and 462 ($^{37}$Cl) [M+H].

EXAMPLE 270

2-[5-Methyl-2-(2-piperidin-4-ylethylamino)-pyrimidin-4-yl]-benzo[b]thiophene-6-carboxylic acid methylamide di-hydrochloride A stirred mixture of 2-(2-chloro-5-methylpyrimidin-4-yl)-benzo[b]thiophene-6-carboxylic acid methylamide (400 mg, 1.20 mmol), 4-(2-aminoethyl)-piperidine-1-carboxylic acid tert-butyl ester (688 mg, 3.01 mmol) and diisopropylethylamine (467 mg, 3.61 mmol) in 1,4-dioxane (4 mL) is heated at 95° C. under nitrogen for 3 days. At room temperature the mixture is concentrated and the crude product is chromatographed on silica gel, eluting with EtOAc in dichloromethane 0-35%, to give 4-{2-[5-methyl-4-(6-methylcarbamoyl-benzo[b]thiophen-2-yl)-pyrimidin-2-ylamino]-ethyl}-piperidine-1-carboxylic acid tert-butyl ester as a solid (264 mg, 43% yield). The intermediate is subjected to deprotection by dissolving this material (264 mg, 0.518 mmol) in MeOH (12 mL) and bubbling anhydrous HCl gas for 5 minutes. The hot, yellow solution is allowed to sit at room temperature for 2 hours, then concentrated to give the title compound as a yellow solid (246 mg, 98% yield). ES+(m/z) 410 [M(free base)+H].

EXAMPLE 271

2-[5-Methyl-2-(3-piperidin-4-yl-propylamino)-pyrimidin-4-yl]-benzo[b]thiophene-6-carboxylic acid dimethylamide di-hydrochloride Using the method of 2-[5-methyl-2-(2-piperidin-4-ylethylamino)-pyrimidin-4-yl]-benzo[b]thiophene-6-carboxylic acid methylamide di-hydrochloride, the title compound is synthesized from 2-(2-chloro-5-methylpyrimidin-4-yl)-benzo[b]thiophene-6-carboxylic acid dimethylamide and 4-(3-aminopropyl)-piperidine-1-carboxylic acid tert-butyl ester and isolated as a foam. ES+(m/z) 438 [M(free base)+H].

EXAMPLE 272

2-{5-Methyl-2-[2-(1-methylpiperidin-4-yl)-ethylamino]-pyrimidin-4-yl}-benzo[b]thiophene-6-carboxylic acid methylamide Aqueous formaldehyde (37.4% or 13.5 M, 0.711 mL, 9.60 mmol) is added to a stirred solution of 2-[5-methyl-2-(2-piperidin-4-yl-ethylamino)-pyrimidin-4-yl]-benzo[b]thiophene-6-carboxylic acid methylamide (346 mg, 0.845 mmol) in $CH_3OH$ (10 mL) and dichloromethane (10 mL) at room temperature. The resultant mixture is stirred for 90 minutes. After being cooled to 0° C., the mixture is treated with powdered sodium borohydride (211 mg, 8.00 mmol) and stirred for 60 minutes. The mixture is allowed to stir at room temperature for 3 hours, concentrated and subject to chromatographic purification on silica gel, eluting with 2 M $NH_3$/$CH_3OH$ in dichloromethane 0-8%, to give the title compound as a yellowish foam (280 mg, 78% yield). ES+(m/z) 424 [M+H].

EXAMPLE 273

2-{5-Methyl-2-[3-(1-methylpiperidin-4-yl)-propylamino]-pyrimidin-4-yl}-benzo[b]thiophene-6-carboxylic acid dimethylamide di-hydrochloride Using the method of 2-{5-chloro-2-[3-(4-ethyl-1-methylpiperidin-4-yl)-propylamino]-pyrimidin-4-yl}-benzo[b]thiophene-4-carboxylic acid cyclopropylamide di-hydrochloride, the title compound is synthesized from 2-[5-methyl-2-(3-piperidin-4-yl-propylamino)-pyrimidin-4-yl]-benzo[b]thiophene-6-carboxylic acid dimethylamide di-hydrochloride and isolated as yellow foam. ES+(m/z) 452 [M(free base)+H].

EXAMPLE 274

2-{5-Methyl-2-[2-(1-methylpiperidin-4-yl)-ethylamino]-pyrimidin-4-yl}-benzo[b]thiophene-6-carboxylic acid dimethylamide di-hydrochloride Using the method of 2-{5-chloro-2-[2-(1-methylpiperidin-4-yl)-ethylamino]-pyrimidin-4-yl}-benzo[b]thiophene-4-carboxylic acid amide di-hydrochloride, the title compound is synthesized from crude product 2-[5-methyl-2-(2-piperidin-4-yl-ethylamino)-pyrimidin-4-yl]-benzo[b]thiophene-6-carboxylic acid dimethylamide and isolated as yellow foam (307 mg, 42% yield). ES+(m/z) 438 [M(free base)+H].

EXAMPLE 275

(2-{5-Methyl-2-[3-(1-methylpiperidin-4-yl)-propylamino]-pyrimidin-4-yl}-benzo[b]thiophen-6-yl)-morpholin-4-yl-methanone di-hydrochloride Using the method of 2-{5-methyl-2-[2-(1-methylpiperidin-4-yl)-ethylamino]-pyrimidin-4-yl}-benzo[b]thiophene-6-carboxylic acid dimethylamide di-hydrochloride, the title compound is synthesized from [2-(2-chloro-5-methylpyrimidin-4-yl)-benzo[b]thiophen-6-yl]-morpholin-4-ylmethanone and 4-(3-aminopropyl)-piperidine-1-carboxylic acid tert-butyl ester and isolated as yellow foam. ES+(m/z) 494 [M(free base)+H].

EXAMPLE 276

2-{5-Methyl-2-[3-(4-methylpiperazin-1-yl)-propylamino]-pyrimidin-4-yl}-benzo[b]thiophene-4-carboxylic acid methylamide tri-hydrochloride A stirred mixture of 2-(2-chloro-5-methylpyrimidin-4-yl)-benzo[b]thiophene-4-carboxylic acid methylamide (400 mg, 1.26 mmol) and 3-(4-methylpiperazin-1-yl)-propylamine (594 mg, 3.78 mmol) in 1,4-dioxane (6 mL) is heated at 95° C. under a nitrogen atmosphere for 60 hours. After concentration and subsequent chromatography on silica gel, eluting with 2 M $NH_3$/MeOH in dichloromethane 0-8%, the free base of the title compound is obtained as a solid (325 mg, 59% yield). The free base (300 mg, 0.684 mmol) is dissolved in MeOH (20 mL) and dichloromethane (20 mL) and the solution is bubbled with a small stream of anhydrous HCl gas for 2 minutes. After concentration, the solid is suspended in MeOH (5 mL) and diethyl ether (20 mL), sonicated, filtered and dried at 60° C. under vacuum to give the title compound as a yellow solid (311 mg, 83% yield). ES+(m/z) 439 [M(free base)+H].

EXAMPLE 277

2-{5-Methyl-2-[2-(4-methylpiperazin-1-yl)-ethylamino]-pyrimidin-4-yl}-benzo[b]thiophene-4-carboxylic acid cyclopropylamide tri-hydrochloride Using the method of 2-{5-methyl-2-[3-(4-methylpiperazin-1-yl)-propylamino]-pyrimidin-4-yl}-benzo[b]thiophene-4-carboxylic acid methylamide tri-hydrochloride, the title compound is synthesized from [2-(2-chloro-5-methylpyrimidin-4-yl)-benzo[b]thiophene-4-carboxylic acid cyclopropylamide and 2-(4-methylpiperazin-1-yl)-ethylamine and isolated as a yellow solid. ES+(m/z) 451 [M(free base)+H].

EXAMPLE 278

2-{5-Fluoro-2-[3-(4-methyl-piperazin-1-yl)-propylamino]-pyrimidin-4-yl}-benzo[b]thiophene-4-carboxylic acid cyclopropylamide tri-hydrochloride Using the method of 2-[2-(3-piperazin-1-ylpropylamino)-pyrimidin-4-yl]-benzo[b]thiophene-4-carboxylic acid cyclopropylamide tri-hydrochloride, the title compound is synthesized from 4-bromobenzo[b]thiophene and isolated as a yellow solid. ES+(m/z) 469 [M(free base)+H]. 3-(4-Methylpiperazin-1-yl)-propylamine is used as the nucleophile for the chloride displacement reaction.

EXAMPLE 279

2-{5-Fluoro-2-[2-(1-methyl-piperidin-4-yl)-ethylamino]-pyrimidin-4-yl}-benzo[b]thiophene-4-carboxylic acid cyclopropylamide di-hydrochloride Using the methods of 2-[5-fluoro-2-(3-piperidin-4-ylpropylamino)-pyrimidin-4-yl]-benzo[b]thiophene-4-carboxylic acid cyclopropylamide and 2-{5-fluoro-2-[3-(1-methylpiperidin-4-yl)-propylamino]-pyrimidin-4-yl}-benzo[b]thiophene-4-carboxylic acid cyclopropylamide di-hydrochloride (Example 123), the title compound is synthesized from 4-(2-aminoethyl)-piperidine-1-carboxylic acid tert-butyl ester and 2-(2-chloro-5-fluoropyrimidin-4-yl)-benzo[b]

thiophene-4-carboxylic acid cyclopropylamide and isolated as a yellow solid. ES+(m/z) 454 [M(free base)+H].

Cell Viability Test

RPMI 8226 cells (ATCC #CCL-155; human multiple myeloma cell line) are grown in RPMI 1640 medium (Gibco #11875-093) supplemented with 10% FBS (fetal bovine serum, Gibco #10082-147), 10 mM HEPES (Gibco #15630-080), 1 mM sodium pyruvate (Gibco #11360-070), and 4.5 mg/mL glucose. HCT116 cells (ATCC #CCL-247; human colon cancer cell line) are grown in McCoy's 5A modified medium (Gibco #16600-082) supplemented with 10% FBS (Gibco #10082-147). H460 cells (ATCC #HTB-177; human non-small cell lung cancer line) are grown in RPMI 1640 (Gibco #11875-093) supplemented with 10% FBS (Gibco #10082-147). U87MG cells (ATCC #HTB-14; human glioblastoma cell line) are grown in MEM with Earle's BSS+ glutamine (Gibco #11095-080) supplemented with 10% FBS (Gibco #10091-148), 0.1 mM non-essential amino acids (Gibco #11140-050), and 1 mM sodium pyruvate (Gibco #11360-070). A2780 cells (human ovarian carcinoma) are grown in RPMI 1640 phenol red-free media (Gibco #11835-030) supplemented with 10% FBS (Gibco #10082-147), 2 mM glutamine (Gibco #25030-081), and 10 µg/mL insulin (Sigma 1-0516).

For compound testing, various cancer cells are seeded at 5,000 cells/well in 100 µl corresponding media specified above for each cell line in 96-well plates one day prior to treatment. Cells are treated with test compounds at seven different concentrations in the presence of 1 ng/mL TNFα and 0.5% DMSO for 48 hours (in the case for H460, 0.5 µg/mL cycloheximide (Sigma) was also added to the media). Cell death in each well is determined by the addition of 15 µL of the One Solution Reagent (The CellTiter 96® AQ$_{ueous}$ One Solution Reagent, Promega #G3580). After 1-2 hours of incubation at 37° C., optical densities at 490 nm are measured with a microplate reader (Molecular Devices SpectraMax). Inhibition of cell viability is determined by comparison to the control cells treated in the absence of a test compound.

Example 20 is specifically detailed below.

| Cell Viability Inhibition | Example 20: IC$_{50}$, µM |
|---|---|
| HCT116 | 19.2 |
| H460 | 9.0 |
| RPMI-8226 | 2.2 |
| U87MG | 22.3 |
| A2780 | 11.7 |

IKK-beta Kinase Assay

The kinase activity of purified IKKβ is measured in vitro using a synthetic IKB peptide fragment (-LKKERLLD-DRHDSGLDSMKD-) derived from IKB protein as a substrate. All reactions (30 µL) are started by the addition of the IKKb enzyme (final concentration: 4 nM) and then incubated at room temperature for 90 minutes in the reaction mix containing 20 µM IKB peptide, 10 µM ATP, 5 mM MgCl$_2$, 50 mM Tris-HCl pH 7.5, 3 mM DTT, 4% DMSO, 1 mM Sodium Orthovandate, 0.5 mM β-glycerophosphate, 0.01% Triton X-100, 4 µCi γ-$^{33}$p-ATP/reaction. Reactions are terminated by addition of 30 µL 10% phosphoric acid, and the terminated reaction mix is filtered through a phosphocellulose membrane to remove unused γ-$^{33}$P-ATP. After four washes with 0.5% phosphoric acid, radio-labeled products bound to the filter are counted using a microbeta counter. All exemplified compounds are initially tested at 10 concentrations (20 µM down to 1 nM) using a 1:3 serial dilution scheme on the Beckman Tecan serial diluter. Calculation is done using a software package from IDBS (Activity Base) where an absolute IC$_{50}$ value (non-linear regression) is calculated. Example 20 is specifically detailed below.

| Enzyme Inhibition | Example 20: IC$_{50}$, µM |
|---|---|
| IKKbeta | 0.046 |

The compounds of the present invention are preferable formulated as pharmaceutical compositions administered by a variety of routes. Most preferably, such compositions are for oral administration. Such pharmaceutical compositions and processes for preparing same are well known in the art. See, e.g., REMINGTON: THE SCIENCE AND PRACTICE OF PHARMACY (A. Gennaro, et al., eds., 19$^{th}$ ed., Mack Publishing Co., 1995).

The compounds of Formula I are generally effective over a wide dosage range. For example, dosages per day normally fall within the range of about 0.0001 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

The invention claimed is:
1. A compound of Formula I:

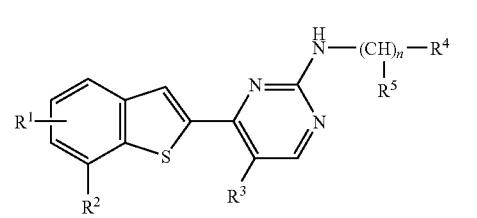

Formula I wherein:
R$^1$ is hydrogen, hydroxy, halo, methylthio, aminosulfonyl, pyrid-2-ylamino, 3-methylaminocarbonylphenyl, —C(O)NR$^8$R$^9$, —(CH$_2$)$_{0-1}$NHSO$_2$R$^{12}$, —CH$_2$NHCONHR$^{13}$, —NHC(O)R$^{14}$, or pyrrolidinonyl optionally substituted with ethyloxycarbonyl;
R$^2$ is hydrogen, hydroxy, halo, cyano, (C$_1$-C$_4$)alkyl, or (C$_1$-C$_4$)alkoxy;
R$^3$ is hydrogen, halo, or methyl;
R$^4$ is (a) —NR$^6$R$^7$ or (b) aminomethylcyclohexyl, piperidinyl, 2,2,6,6-tetramethylpiperidin-4-yl, 2,2,6,6-tetramethylpiperidin-4-ylethenyl, 4-(C$_1$-C$_4$)alkylpiperidin-4-yl, or pyrrolidinyl;
wherein (b) may be optionally substituted with a substituent selected from the group consisting of (C$_2$-C$_4$)alkenyl, $(C_3-C_6)$cycloalkyl, $C(O)R^{10}$, and $(C_1-C_4)$alkyl optionally substituted with halo, $(C_1-C_4)$alkoxy, or $(C_3-C_6)$cycloalkyl;

$R^5$ is hydrogen or hydroxy provided that $R^5$ must be H when n is 1;

$R^6$ is hydrogen or $(C_1-C_4)$alkyl;

$R^7$ is selected from the group consisting of hydrogen, $(C_1-C_4)$alkyl, piperidin-4-yl optionally substituted with $(C_1-C_4)$alkyl, piperidinylcarbonyl optionally substituted with $(C_1-C_4)$alkyl, pyrrolidin-3-yl optionally substituted with $(C_1-C_4)$alkyl, and pyrrolidinylcarbonyl optionally substituted with $(C_1-C_4)$alkyl;

alternatively $R^6$ and $R^7$ along with the nitrogen to which they are attached form a ring selected from the group consisting of piperazinyl, homopiperazinyl, 4-dimethylaminopiperidin-1-yl, 3-dimethylaminopyrrolidin-1-yl, or hexahydro-pyrrolo[3,4-c]pyrrolyl;

wherein the ring may be optionally substituted one time from the group consisting of $(C_2-C_4)$alkenyl, $(C_3-C_6)$cycloalkyl, $C(O)R^{10}$, and one to three $(C_1-C_4)$alkyl substituents optionally substituted with hydroxy;

$R^8$ is hydrogen or $(C_1-C_4)$alkyl;

$R^9$ is hydrogen, $(C_1-C_4)$alkyl, $(C_1-C_4)$alkoxy, $(C_3-C_6)$cycloalkyl, thiazolyl, imidazolyl, pyridyl, phenyl optionally substituted with halo, 2-hydroxy-2-phenyl-ethyl, imidazolylethyl, 6-chloropyrid-3-ylmethyl, or furan-2-yl-$(C_1-C_4$ alkyl);

alternatively $R^8$ and $R^9$ along with the nitrogen to which they are attached form a heterocycle selected from the group consisting of morpholinyl and thiazinyl;

$R^{10}$ is hydrogen, $(C_1-C_4)$alkyl, or $NHR^{11}$;

$R^{11}$ is hydrogen or $(C_1-C_4)$alkyl;

$R^{12}$ is $(C_1-C_4)$alkyl, trifluoro$(C_1-C_4)$alkyl, benzyl, or $(C_3-C_6)$cycloalkyl;

$R^{13}$ is $(C_1-C_4)$alkyl, $(C_3-C_6)$cycloalkyl, or benzyl optionally substituted with $(C_1-C_4)$alkyl, halo, or $(C_1-C_4)$alkoxy;

$R^{14}$ is $(C_3-C_6)$cycloalkyl, piperidinyl, indolylmethyl, or benzyl optionally substituted with 3-dimethylamino-2-hydroxypropoxy;

provided that when $R^4$ is piperidinyl, $R^1$ is —$C(O)NR^8R^9$; and n is 1-7 provided that n is 1 only when $R^4$ is -aminomethylcyclohexyl or 2,2,6,6-tetramethylpiperidin-4-ylethenyl; or a pharmaceutically acceptable salt thereof.

2. A compound of claim 1 wherein $R^1$ is —$C(O)NR^8R^9$ and $R^2$ is hydrogen; or a pharmaceutically acceptable salt thereof.

3. A compound of claim 1 wherein n is 2-3; $R^4$ is —$NR^6R^7$, piperidinyl, or 4-$(C_1-C_4)$alkylpiperidin-4-yl and $R^5$ is hydrogen; or a pharmaceutically acceptable salt thereof.

4. A compound of claim 1 wherein $R^6$ and $R^7$ along with the nitrogen to which they are attached form a piperazinyl optionally substituted with $(C_1-C_4)$alkyl; or a pharmaceutically acceptable salt thereof.

5. A compound of claim 1 wherein $R^8$ is hydrogen or $(C_1-C_4)$alkyl and $R^9$ is $(C_1-C_4)$alkyl or $(C_3-C_6)$cycloalkyl or alternatively $R^8$ and $R^9$ along with the nitrogen to which they are attached form a morpholinyl; or a pharmaceutically acceptable salt thereof.

6. The compound of claim 1 which is 2-{5-Methyl-2-[3-(4-methylpiperazin-1-yl)-propylamino]-pyrimidin-4-yl}-benzo[b]thiophene-4-carboxylic acid methylamide; or a pharmaceutically acceptable salt thereof.

7. A pharmaceutical formulation comprising a compound according to any one of claim 1 or a pharmaceutically acceptable salt thereof, in combination with a pharmaceutically acceptable carrier, diluent or excipient.

8. A method of treating a cancer selected from the group consisting of multiple myeloma, colon cancer, large cell lung cancer, glioblastoma, and ovarian cancer in a mammal comprising administering to a mammal in need of such treatment an effective amount of a compound according to any one of claim 1 or a pharmaceutically acceptable salt thereof.

9. A method of treating inflammatory diseases selected from the group consisting of rheumatoid arthritis and chronic obstructive pulmonary disease, in a mammal comprising administering to a mammal in need of such treatment an effective amount of a compound according to any one of claim 1 or a pharmaceutically acceptable salt thereof.

* * * * *

UNITED STATES PATENT AND TRADEMARK OFFICE
CERTIFICATE OF CORRECTION

PATENT NO. : 7,547,691 B2  Page 1 of 1
APPLICATION NO. : 12/093024
DATED : June 16, 2009
INVENTOR(S) : Karl Robert Dahnke It is certified that error appears in the above-identified patent and that said Letters Patent is hereby corrected as shown below:

1) Column 99, line 28
   Claims, Claim 1:
   Delete "yl-(C1-C4 alkyl);" and
   Insert --yl-(C1-C4)alkyl;--, therefore.

2) Column 100, line 26
   Claims, Claim 7:
   Delete "any one of".

3) Column 100, line 33
   Claims, Claim 8:
   Delete "any one of".

4) Column 100, line 39
   Claims, Claim 9:
   Delete "any one of".

Signed and Sealed this

Thirtieth Day of March, 2010

David J. Kappos
*Director of the United States Patent and Trademark Office*